US011858956B2

(12) United States Patent
Moukha-Chafiq et al.

(10) Patent No.: US 11,858,956 B2
(45) Date of Patent: Jan. 2, 2024

(54) 6-AZA-NUCLEOSIDE PRODRUGS AS ANTIVIRAL AGENTS FOR TREATING VIRUS INFECTIONS

(71) Applicants: Southern Research Institute, Birmingham, AL (US); Oregon Health & Science University, Portland, OR (US); Washington University in St. Louis, St. Louis, MO (US); Board of Regents, The University of Texas System, Austin, TX (US)

(72) Inventors: Omar Moukha-Chafiq, Hoover, AL (US); Ashish Kumar Pathak, Birmingham, AL (US); Shuklendu D. Karyakarte, Birmingham, AL (US); Larry D. Bratton, Birmingham, AL (US); Corinne E. Augelli-Szafran, Homewood, AL (US); Michael Diamond, St. Louis, MO (US); Pei Yong Shi, Galveston, TX (US); Alec Jay Hirsch, Portland, OR (US); Jessica Lee Smith, Beaverton, OR (US); Daniel Streblow, Banks, OR (US); Nicole Haese, Beaverton, OR (US); Baoling Ying, Ballwin, MO (US)

(73) Assignees: Southern Research Institute, Birmingham, AL (US); Oregon Health & Science University, Portland, OR (US); Washington University in St. Louis, St. Louis, LA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/554,979

(22) Filed: Dec. 17, 2021

(65) Prior Publication Data
US 2022/0204545 A1    Jun. 30, 2022

Related U.S. Application Data

(60) Provisional application No. 63/127,693, filed on Dec. 18, 2020.

(51) Int. Cl.
   *C07H 19/12*    (2006.01)
   *A61P 31/14*    (2006.01)
   *A61P 31/16*    (2006.01)

(52) U.S. Cl.
   CPC ............ *C07H 19/12* (2013.01); *A61P 31/14* (2018.01); *A61P 31/16* (2018.01)

(58) Field of Classification Search
   None
   See application file for complete search history.

(56) References Cited

U.S. PATENT DOCUMENTS

2010/0087388 A1    4/2010    Kotra et al.
2020/0101095 A1    4/2020    Traverse et al.

FOREIGN PATENT DOCUMENTS

WO    PCT/US2021/064220    12/2021

OTHER PUBLICATIONS

Pasternak et al., Journal of Biological Chemistry, 1959, vol. 234, pp. 2992-2997. (Year: 1959).*
Gabrielsen et al., Antiviral Chemistry and Chemotherapy, 1994, 5(4), pp. 209-220. (Year: 1994).*
Pubchem Compound Record for CID 154219545—Aug. 14, 2020 (Year: 2020).*
Prystas et al., Collection of Czechoslovak Chemical Communications, 28(11), 1963, pp. 3113-3121. (Year: 1963).*
Tsume, et al. (2014) "The development of orally administrable gemcitabine prodrugs with D-enantiomer amino acid: Enhanced membrane permeability and enzymatic stability," *Eur. J. Pharm. Sci.* 86: 514-523.
Zhang, et al. (2013) "A Carrier-Mediated Prodrug Approach To Improve the Oral Absorption of Antileukemic Drug Decitabine," *Mol. Pharmaceutics* 10: 3195-3202.
Vig, et al. (2013) "Amino acids as promoities in prodrug design and development," *Adv. Drug Deliv. Rev.* 65: 1370-1385.
Hasabelnaby, et al. (2012) "Synthesis, chemical and enzymatic hydrolysis, and aqueous solubility of amino acid ester prodrugs of 3-carboranyl thymidine analogs for boron neutron capture therapy of brain tumors," *Eur. J. Med. Chem.* 55: 325-334.
Song, et al. (2005) "Amino acid ester prodrug of the anticancer agent gemcitabine: Synthesis, bioconversion, metabolic bioevasion and hPEPT1-mediated transport," *Mol. Pharm.* 2: 157-167.
Landowski, et al. (2005) "Targeted delivery to PEPT1-overexpresssing cells: Acidic, basic, and secondary floxuridine amino acid ester prodrugs," *Mol. Cancer Ther.* 4: 659-667.

(Continued)

*Primary Examiner* — Traviss C Mcintosh, III
(74) *Attorney, Agent, or Firm* — Ballard Spahr LLP

(57) ABSTRACT

The present disclosure is concerned with 6-aza-nucleoside prodrugs that are capable of inhibiting a viral infection and methods of treating viral infections such as, for example, human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), and coronavirus disease 2019 (COVID-19), using these compounds. This abstract is intended as a scanning tool for purposes of searching in the particular art and is not intended to be limiting of the present invention.

18 Claims, No Drawings

(56) References Cited

OTHER PUBLICATIONS

Landowski, et al. (2005) "Floxuridine amino acid ester prodrugs: Enhancing Caco-2 permeability and resistance to glycosidic bond metabolism," *Pharm. Res.* 22: 1510-1518.
Sugawara, et al. (2000) "Transport of valganciclovir, a ganciclovir prodrug, via peptide transporters PEPT1 and PEPT2," J. Pharm. Sci. 89: 781-789.
Guo, et al. (1999) "Interactions of a nonpeptidic drug, valacyclovir, with the human intestinal peptide transporter (hPEPT1) expressed in a mammalian cell line," *J. Pharmacol. Exp. Ther.* 289: 448-454.
Balimane, et al. (1998) "Direct evidence for peptide transporter (PepT1)-mediated uptake of a nonpeptide prodrug, valacyclovir," *Biochem. Biophys. Res. Commun.* 250: 246-251.
De Vrueh, et al. (1998) "Transport of L valineacyclovir via the oligopeptide transporter in the human intestinal cell line, Caco-2," *J. Pharmacol. Exp. Ther.* 286: 1166-1170.
U.S. Appl. No. 63/127,693, filed 63/127,693, Omar Moukha-Chafiq.
Pubchem Compound Record for CID 154219545; N-[2-[(2R,3R,4S,5R)-3,4-dihydroxy-5-(hydroxymethyl)oxolan-2-yl]-3-oxo-1,2,4-triazin-5-yl]acetamide (htttps://pubchem.ncbi.nlm.nih.gov/compound/154219545). Created Aug. 14, 2020.
Pubchem Compound Record for CID 15346065; 4'-Amino-2'-fluoro-5'-(o-methoxyanilino)acetanilide (https://pubchem.ncbi.nlm.nih.gov/compound/15346065). Created Feb. 9, 2007.
Pubchem Compound Record for CID 150959 "6-Aza uridine 5'-monophosphate" (https://pubchem.ncbi.nlm.nih.gov/compound/150959). Created Jun. 24, 2005.

* cited by examiner

6-AZA-NUCLEOSIDE PRODRUGS AS ANTIVIRAL AGENTS FOR TREATING VIRUS INFECTIONS

CROSS-REFERENCE TO RELATED APPLICATIONS

This Application claims the benefit of U.S. Application No. 63/127,693, filed on Dec. 18, 2020, the contents of which are hereby incorporated by reference in their entirety.

STATEMENT REGARDING FEDERALLY SPONSORED RESEARCH

This invention was made with government support under grant number 1U19AI109680-01 and 1U19AI142759-01 awarded by the National Institute of Allergy and Infectious Diseases (NIAD) and the National Institutes of Health (NIH). The government has certain rights in the invention.

BACKGROUND

Arthropod borne viruses have developed a complex life cycle adapted to alternate between insect and vertebrate hosts. These arthropod-borne viruses belong mainly to the families Togaviridae, Flaviviridae, and Bunyaviridae. Flavivirus is a genus of the family Flaviviridae. This genus includes such viral infections as West Nile virus (WNV), dengue virus (DENV), Tick-borne Encephalitis virus, yellow fever virus, and zika virus (ZIKV) that may cause encephalitis. Alphavirus is a genus of the family Togaviridae. This genus includes such viral infections as chikungunya virus (CHIKV), Venezuelan Equine Encephalitis virus (VEEZ), Western Equine Encephalitis virus (WEEV), and Eastern Equine Encephalitis virus (EEEV).

Zika virus (ZIKV) is a single stranded RNA virus transmitted to humans primarily via *Aedes aegypti* mosquitos and other mosquitos of the *Stegomyia* subgenus. ZIKV can also be transmitted through sexual intercourse, a blood transfusion, or from a pregnant woman to her fetus. Infection during pregnancy can result in microcephaly and other severe fetal brain defects. Additional problems detected among fetuses and infants infected with ZIKV before birth include as defects of the eye, hearing deficits, and impaired growth. Increased reports of Guillain-Barre syndrome have also been observed in areas affected by Zika. Until recently, only sporadic human ZIKV infections had been reported. Since 2007, ZIKV has expanded from Asia and Africa to include both North and South America.

DENV is a mosquito-borne virus estimated to cause 50-100 million infections each year. DENV infections can result in serious diseases including dengue fever, dengue hemorrhagic fever, and dengue shock syndrome, and may even result in death. This virus is considered by the World Health Organization to be the most important mosquito-borne viral disease worldwide.

West Nile virus (WNV) is the leading cause of mosquito-borne illness in the continental United States. It is most commonly spread to people by the bite of a mosquito. Most human infections are mild, causing fever, headache, and body aches, often accompanied by a skin rash and swollen lymph glands. If the virus crosses the blood-brain barrier, however, it can cause life-threatening conditions that include inflammation of the brain and spinal cord. Despite the severe implications of this disease, there is currently no vaccine or antiviral treatment available for WNV.

Originally isolated in Tanzania, sporadic outbreaks of CHIKV have continued to plague Asia and Africa. In 2007, the first outbreak in Europe was documented with over 200 confirmed cases. To date, CHIKV has been identified in over 40 countries including the United States of America. The symptoms of CHIKV, which include fever, rash, and severe joint pain, are commonly indistinguishable from ZIKV and DENV. While most patients usually recover after days to weeks, some may develop chronic arthritis. Additionally, death related to Chikungunya infection has been reported in older patients or patients with weakened immune systems.

VEEV, which was originally isolated from the brains of dead horses, emerges during epizootic outbreaks to infect horses and humans via bridge vectors such as *Aedes taeniorhynchus*. Epidemics typically occur in northern South America but have extended as far north as Mexico and Texas. During an outbreak in Venezuela and Colombia in 1995, approximately 3000 cases of neurologic disease were reported, resulting in 300 deaths.

WEEV causes asymptomatic or mild infections in humans, with non-specific symptoms such as sudden onset of fever, headache, nausea, vomiting, anorexia, and malaise. In rare cases, WEEV infection may also cause encephalitis or encephalomyelitis. Fifteen to fifty percent of the encephalitis survivors, especially young children, suffer from permanent neurological damage (mental retardation, emotional instability, and spastic paresis). WEEV has a mortality range of three to seven percent.

EEEV is the most severe of the arboviral encephalitides and has a mortality of 50 to 75%. Symptoms of this disease include fever, headache, vomiting, respiratory symptoms, leucocytosis, dizziness, decreasing level of consciousness, tremors, seizures, and focal neurological signs. Death can occur within 3 to 5 days of infection. Those who survive suffer from neurological sequel, including convulsions, paralysis, and mental retardation.

Unlike arthropod borne viruses, which are typically transmitted via vector pests such as ticks and mosquitos, coronaviruses are primarily transmitted through contact with bodily fluid from an infected person (e.g., coughing, sneezing). There are six human types of coronavirus: 229E, OC43, NL63, HKU1, which are often associated with mild upper respiratory tract infections, as well as the virus causing severe acute respiratory syndrome (SARS-CoV), Middle East respiratory syndrome (MERS-CoV), and severe acute respiratory syndrome coronavirus 2 (SARS-CoV-2), each of which are zoonotic but have also caused human disease. Interspecies transmission and the resulting emergent coronaviruses have been important factors in emerging respiratory disease as coronaviruses are known to infect feline, swine, canine, and bat species. Indeed, MERS-CoV, SARS-CoV, and SARS-CoV-2 emerged from animal reservoirs and are now increasingly important respiratory virus threats. To date, nearly 2 million cases of SARS-CoV-2 have been confirmed in humans, resulting in over 74,000 deaths.

The orthomyxoviruses are viruses with negative-sense, segmented RNA genomes and includes the influenza viruses. There are two main types of influenza (flu) virus: Types A and B. The influenza A and B viruses that routinely spread in people (human influenza viruses) are responsible for seasonal flu epidemics each year. The emergence of influenza A viruses from the aquatic avian reservoir occurs intermittently and causes seasonal epidemics and infrequent pandemics. The transmissibility of the virus and the susceptibility of the population are among the factors that determine the extent to which new strains circulate in the general population. Three common subtypes (H1, H2, and H3)

predominate in humans, although occasionally other subtypes are acquired as zoonoses and include subtypes such as H5 and H7. Similarly, two major subtypes of neuraminidases (N1 and N2) commonly circulate in the population while additional subtypes are occasionally introduced in conjunction with novel subtypes of hemagglutinin. Transmission of highly pathogenic avian influenza strains to humans occurs occasionally and recent laboratory confirmed infections with H5N1 and H7N9 strains have been confirmed, are associated with elevated levels of morbidity and mortality, and as such are a significant public health concern. Antiviral therapy of influenza A strains can also give rise to resistant infections that are efficiently transmitted and in some instances can become the predominant phenotype in circulating strains of some viruses. This underscores the need for the development of new antiviral drugs against influenza viruses as well as a therapeutic strategy to reduce the emergence of resistant strains.

Currently, there are no approved treatments for ZIKV, DENV, WNV, CHIKV, VEEV, EEEV, WEEV, MERS-CoV, SARS-CoV, or SARS-CoV-2 and influenza. Despite the widespread distribution and severity of the effects of these viral infections, a treatment has remained elusive. Thus, there remains a need for antiviral agents capable of targeting these viruses and methods of making and using same.

SUMMARY

In accordance with the purpose(s) of the invention, as embodied and broadly described herein, the invention, in one aspect, relates to compositions and methods for use in the prevention and treatment of viral infections due to, for example, an Alphavirus (e.g., Chikungunya virus (CHIKV), Ross River virus, Venezuelan equine encephalitis (VEEV), Eastern equine encephalitis (EEEV), and Western equine encephalitis (WEEV)), a Flavivirus (e.g., dengue virus (DENV), West Nile virus (WNV), zika virus (ZIKV), tick-borne encephalitis virus, and yellow fever virus), Coronavirus (e.g., Middle East Respiratory Syndromes coronavirus (MERS-CoV), Severe Acute Respiratory Syndrome coronavirus (SARS-CoV), and SARS-CoV-2), and a influenza viruses.

Disclosed are compounds having a structure represented by a formula:

wherein $R^1$ is selected from hydrogen, —C(O)$R^{10}$, —C(O)CH($R^{11}$)$NH_2$, —P(O)(O$Ar^1$)NHCH($R^{12}$)$CO_2R^{13}$, and —P(O)(O$R^{14a}$)(O$R^{14b}$); wherein $R^{10}$, when present, is selected from C1-C20 alkyl and C2-C20 alkenyl; wherein $R^{11}$, when present, is an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, $Ar^2$, and —$CH_2Ar^2$; wherein $Ar^2$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein $Ar^1$, when present, is selected from C6-C14 aryl and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

and

;

and wherein $R^{15}$, when present, is selected from hydrogen, —C(O)(C1-C20 alkyl), —C(O)(C3-C6 cycloalkyl), and —C(O)(C2-C20 alkenyl), provided that when $R^2$ is 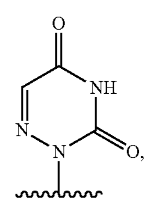 [SMILES: *n1ncc(=O)[nH]c1=O] then $R^1$ is —C(O)CH($R^{11}$)$NH_2$—P(O)(O$Ar^1$)NHCH($R^{12}$)$CO_2R^{13}$, or —P(O)(O$R^{14a}$)(O$R^{14b}$), and provided that when $R^1$ is hydrogen, then $R^{15}$ is —C(O)(C1-C20 alkyl), —C(O)(C3-C6 cycloalkyl), or —C(O)(C2-C20 alkenyl), or a pharmaceutically acceptable salt thereof.

Also disclosed are compound having a structure:

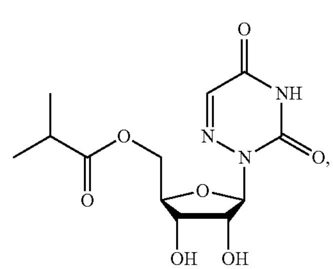

or a pharmaceutically acceptable salt thereof.

Also disclosed are pharmaceutical compositions comprising a therapeutically effective amount of a disclosed compound and a pharmaceutically acceptable carrier.

Also disclosed are methods for treating a viral infection in a subject in need thereof, the method comprising administering to the subject a compound having a structure represented by a formula:

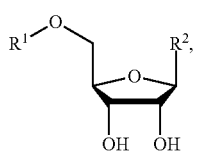

wherein $R^1$ is selected from hydrogen, —C(O)$R^{10}$, —C(O)CH($R^{11}$)NH$_2$, —P(O)(OAr$^1$)NHCH($R^{12}$)CO$_2R^{13}$, and —P(O)(O$R^{14a}$)(O$R^{14b}$); wherein $R^{10}$, when present, is selected from C1-C20 alkyl and C2-C20 alkenyl; wherein $R^{11}$, when present, is a an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

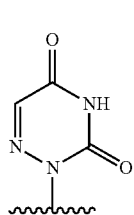 and 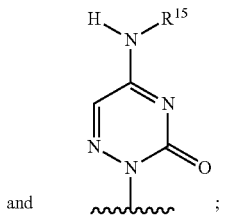;

and
wherein $R^{15}$, when present, is selected from hydrogen, —C(O)(C1-C20 alkyl), —C(O)(C3-C6 cycloalkyl), and —C(O)(C2-C20 alkenyl), provided that when $R^1$ is hydrogen, then $R^2$ is

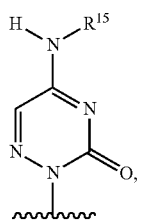

and $R^{15}$ is —C(O)(C1-C20 alkyl), —C(O)(C3-C6 cycloalkyl), or —C(O)(C2-C20 alkenyl), or a pharmaceutically acceptable salt thereof.

Also disclosed are kits comprising a compound having a structure represented by a formula:

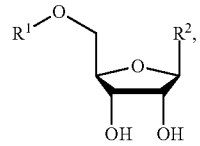

wherein $R^1$ is selected from hydrogen, —C(O)$R^{10}$, —C(O)CH($R^{11}$)NH$_2$, —P(O)(OAr$^1$)NHCH($R^{12}$)CO$_2R^{13}$, and —P(O)(O$R^{14a}$)(O$R^{14b}$); wherein $R^{10}$, when present, is selected from C1-C20 alkyl and C2-C20 alkenyl; wherein $R^{11}$, when present, is a an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

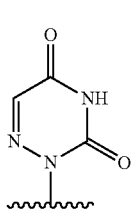 and 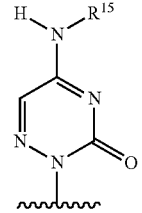;

and
wherein $R^{15}$, when present, is selected from hydrogen, —C(O)(C1-C20 alkyl), —C(O)(C3-C6 cycloalkyl), and —C(O)(C2-C20 alkenyl), provided that when $R^1$ is hydrogen, then $R^2$ is

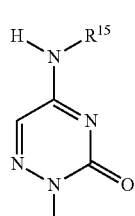

and $R^{15}$ is —C(O)(C1-C20 alkyl), —C(O)(C3-C6 cycloalkyl), or —C(O)(C2-C20 alkenyl), or a pharmaceutically acceptable salt thereof, and one or more of: (a) at least one antiviral agent; (b) at least one immunity booster; (c) instructions for administering the compound in connection with treating a viral infection; (d) instructions for administering the compound in connection with reducing the risk of viral infection; or (e) instructions for treating a viral infection.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

As used herein, "$EC_{50}$" is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$EC_{90}$" is intended to refer to the concentration of a substance (e.g., a compound or a drug) that is required for 90% agonism of a biological process, or component of a process, including a protein, subunit, organelle, ribonucleoprotein, etc. In one aspect, an $EC_{90}$ can refer to the concentration of a substance that is required for 90% agonism in vivo, as further defined elsewhere herein.

As used herein, "$CC_{50}$" is intended to refer to the concentration of a substance (e.g., a compound or a drug) that is required for 50% reduction of cell viability. In one aspect, an $CC_{50}$ can refer to the concentration of a substance that is required for 50% reduction (i.e., cytotoxicity) in vivo, as further defined elsewhere herein.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized n electrons above and below the plane of the molecule, where the a clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O. The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" and "heterocyclyl" as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" and "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH═CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)O$—N(R^\circ)_2$; or $—(C_{1-4}$ straight or branched alkylene)C(O)O$—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; $—O(haloR^\bullet)$, —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)C(O)O$R^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

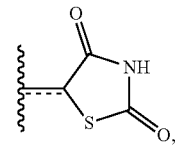

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

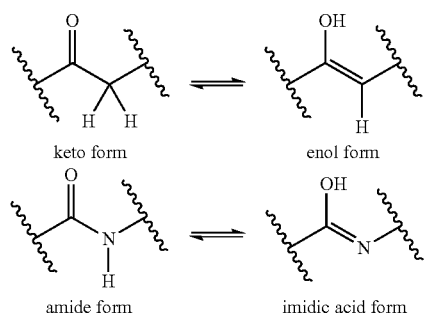

Likewise, amides with an N-hydrogen can exist in an equilibrium of the amide form and the imidic acid form. As another example, pyrazoles can exist in two tautomeric forms, $N^1$-unsubstituted, 3-$A^3$ and $N_1$-unsubstituted, 5-$A^3$ as shown below.

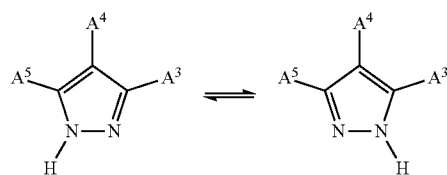

Unless stated to the contrary, the invention includes all such possible tautomers.

It is known that chemical substances form solids that are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

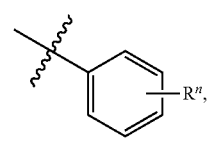

which is understood to be equivalent to a formula:

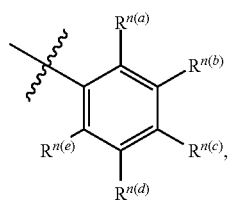

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in treating disorders associated with a viral infection due to, in particular, an Alphavirus (e.g., Chikungunya virus (CHIKV), Ross River virus, Venezuelan equine encephalitis (VEEV), Eastern equine encephalitis (EEEV), and Western equine encephalitis (WEEV)), a Flavivirus (e.g., dengue virus (DENV), West Nile virus (WNV), zika virus (ZIKV), tick-borne encephalitis virus, and yellow fever virus), and a Coronavirus (e.g., Middle East Respiratory Syndromes coronavirus (MERS-CoV), Severe Acute Respiratory Syndrome coronavirus (SARS-CoV), and SARS-CoV-2).

In one aspect, the disclosed compounds exhibit antiviral activity.

In one aspect, the compounds of the invention are useful in inhibiting viral activity in a mammal. In a further aspect, the compounds of the invention are useful in inhibiting viral activity in at least one cell.

In one aspect, the compounds of the invention are useful in the treatment of viral infections, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

wherein $R^1$ is selected from hydrogen, —C(O)$R^{10}$, —C(O)CH($R^{11}$)NH$_2$, —P(O)(OAr$^1$)NHCH($R^{12}$)CO$_2$$R^{13}$, and —P(O)(OR$^{14a}$)(OR$^{14b}$); wherein $R^{10}$, when present, is selected from C1-C20 alkyl and C2-C20 alkenyl; wherein $R^{11}$, when present, is an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

and wherein $R^{15}$, when present, is selected from hydrogen, —C(O)(C1-C20 alkyl), —C(O)(C3-C6 cycloalkyl), and —C(O)(C2-C20 alkenyl), provided that when $R^2$ is

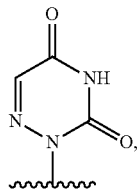

then $R^1$ is —C(O)CH($R^{11}$)NH$_2$, —P(O)(OAr$^1$)NHCH($R^{12}$)CO$_2$R$^{11}$, or —P(O)(OR$^{14a}$)(OR$^{14b}$), and provided that when $R^1$ is hydrogen, then $R^{15}$ is —C(O)(C1-C20 alkyl), —C(O)(C3-C6 cycloalkyl), or —C(O)(C2-C20 alkenyl), or a pharmaceutically acceptable salt thereof.

In one aspect, disclosed are compounds having a structure:

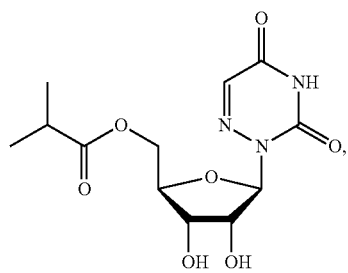

or a pharmaceutically acceptable salt thereof.

In a further aspect, the compound has a structure represented by a formula selected from:

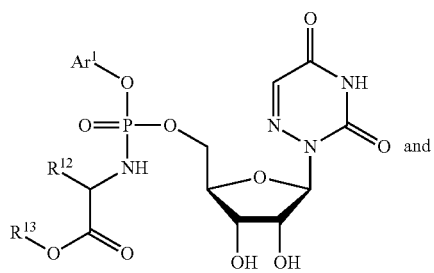

and

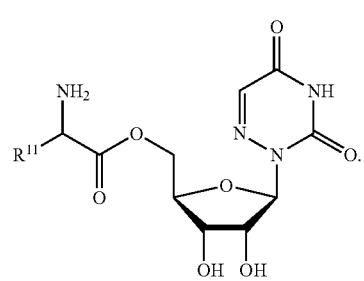

In a further aspect, the compound is selected from:

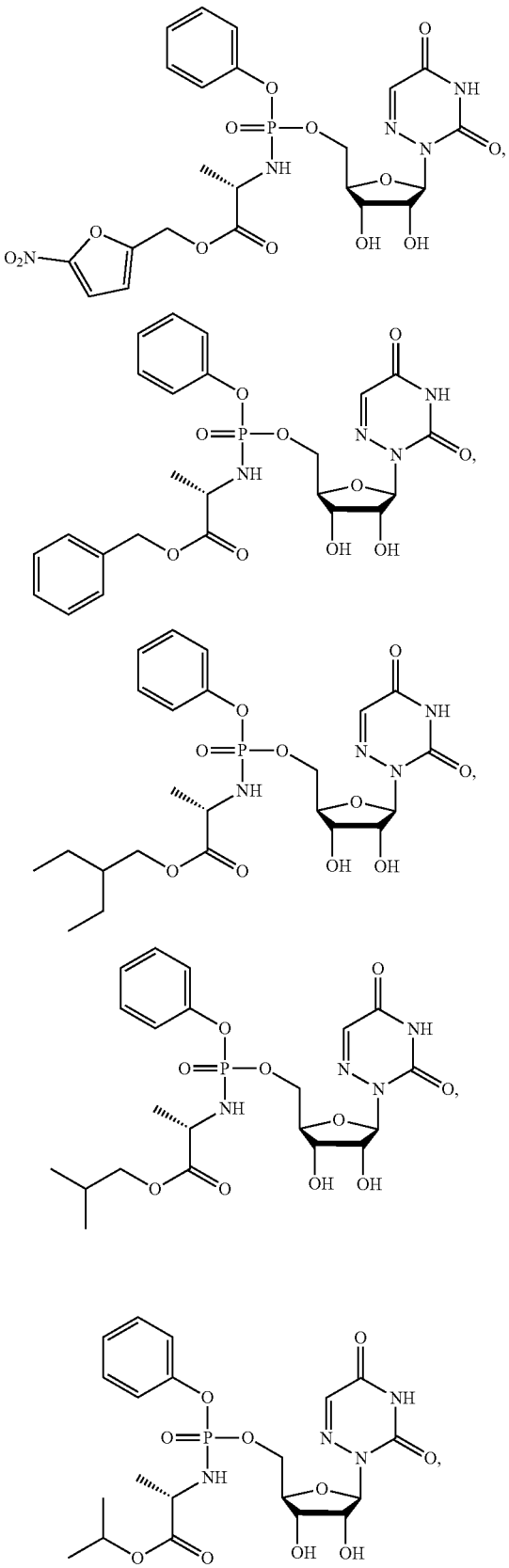

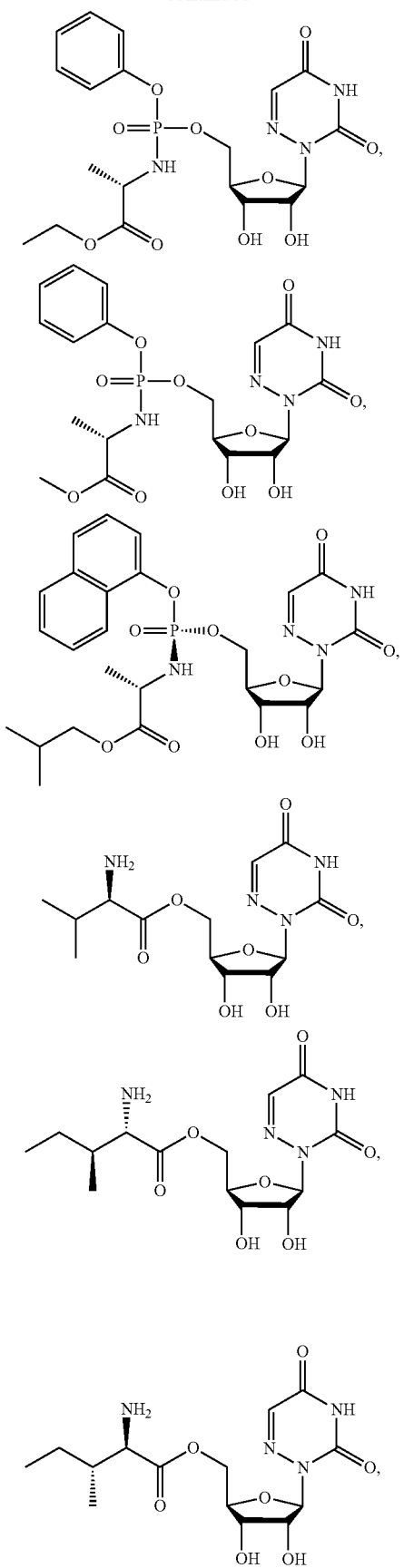
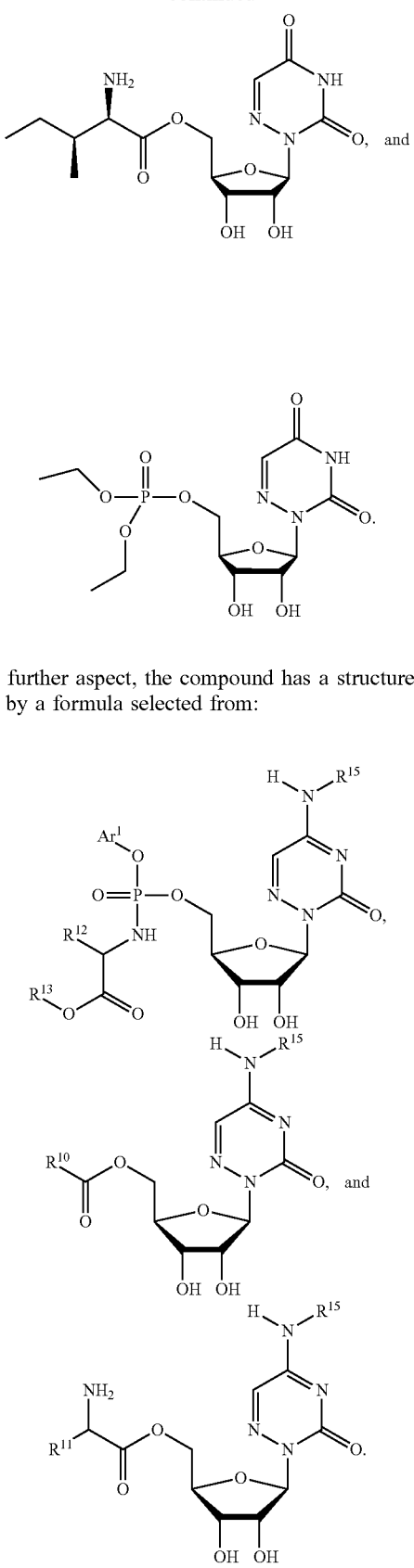
In a further aspect, the compound has a structure represented by a formula selected from:

In a further aspect, the compound has a structure represented by a formula selected from:
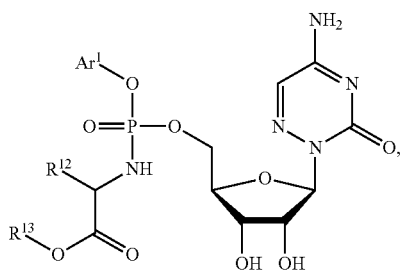
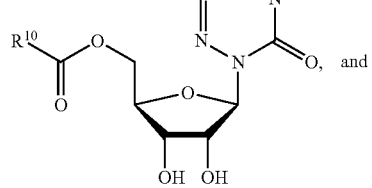
In a further aspect, the compound has a structure represented by a formula:
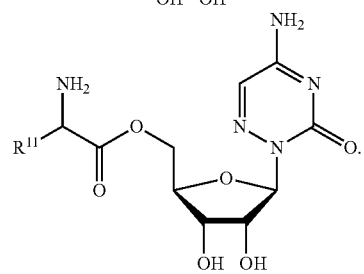
In a further aspect, the compound is selected from:
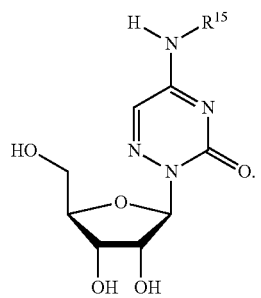
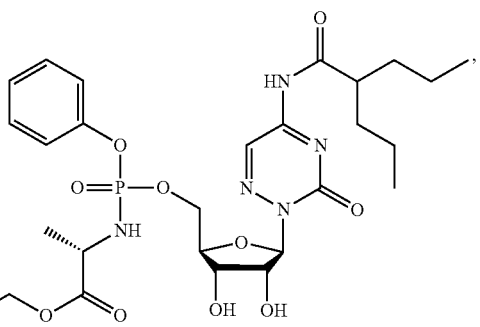
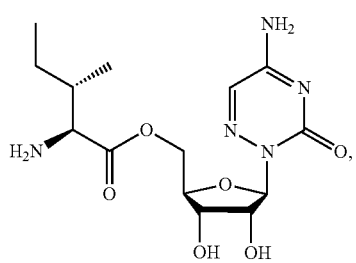
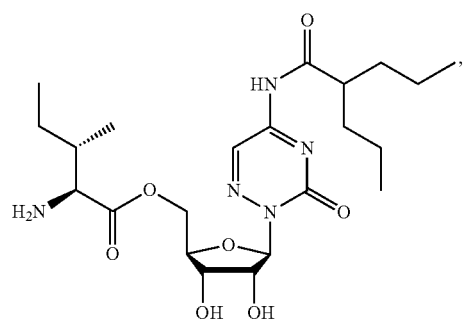
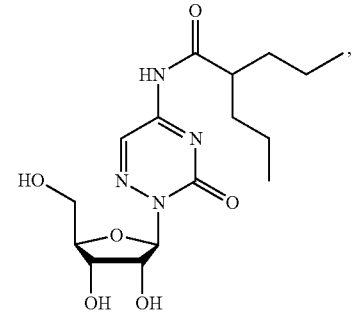
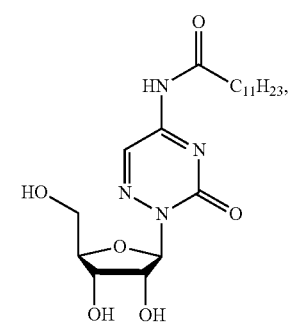

-continued

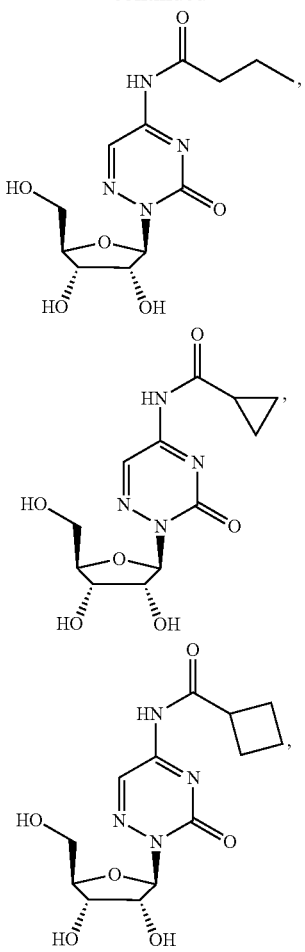

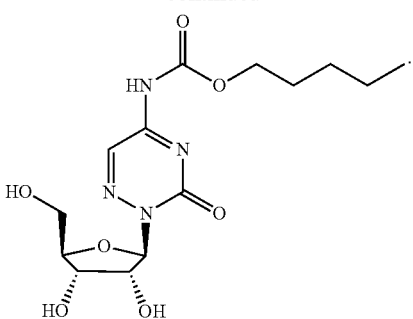

In a further aspect, the compound is:

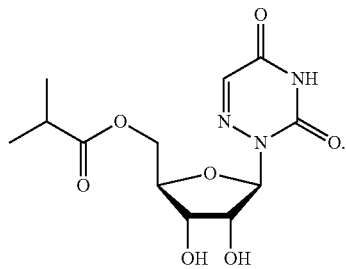

a. R¹ Groups

In one aspect, $R^1$ is selected from hydrogen, —C(O)$R^{10}$, —C(O)CH($R^{11}$)NH$_2$, —P(O)(OAr$^1$)NHCH($R^{12}$)CO$_2$$R^{13}$, and —P(O)(O$R^{14a}$)(O$R^{14b}$). In a further aspect, $R^1$ is selected from hydrogen, —C(O)$R^{10}$, —C(O)CH($R^{11}$)NH$_2$, and —P(O)(OAr$^1$)NHCH($R^{12}$)CO$_2$$R^{13}$. In a still further aspect, $R^1$ is selected from hydrogen, —C(O)$R^{10}$, and —C(O)CH($R^{11}$)NH$_2$. In yet a further aspect, $R^1$ is selected from hydrogen and —C(O)$R^{10}$. In an even further aspect, $R^1$ is hydrogen.

In various aspects, $R^1$ is selected from —C(O)$R^{10}$ and —C(O)CH($R^{11}$)NH$_2$. In a further aspect, $R^1$ is —C(O)$R^{10}$. In a still further aspect, $R^1$ is —C(O)CH($R^{11}$)NH$_2$.

In various aspects, $R^1$ is selected from —P(O)(OAr$^1$)NHCH($R^{12}$)CO$_2$$R^{13}$ and —P(O)(O$R^{14a}$)(O$R^{14b}$). In a further aspect, $R^1$ is —P(O)(OAr$^1$)NHCH($R^{12}$)CO$_2$$R^{13}$. In a still further aspect, $R^1$ is —P(O)(O$R^{14a}$)(O$R^{14b}$).

b. R² Groups

In one aspect, $R^2$ is a structure represented by a formula selected from:

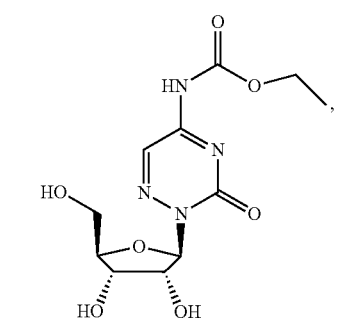

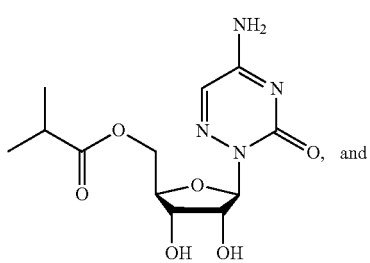

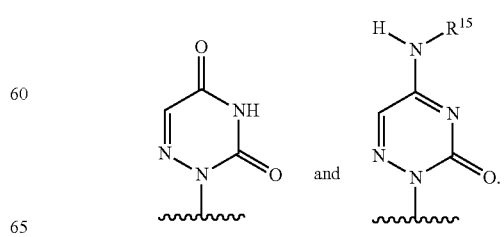

In a further aspect, $R^2$ is a structure represented by a formula:

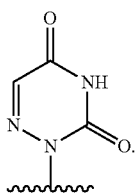 [SMILES: *n1ncc(=O)[nH]c1=O]

In a further aspect, $R^2$ is a structure represented by a formula:

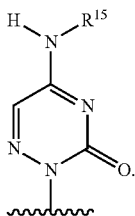

c. $R^{10}$ Groups

In one aspect, $R^{10}$, when present, is selected from C1-C20 alkyl and C2-C20 alkenyl. In a further aspect, $R^{10}$, when present, is selected from C1-C16 alkyl and C2-C16 alkenyl. In a still further aspect, $R^{10}$, when present, is selected from C1-C12 alkyl and C2-C12 alkenyl. In yet a further aspect, $R^{10}$, when present, is selected from C1-C8 alkyl and C2-C8 alkenyl. In an even further aspect, $R^{10}$, when present, is selected from C1-C4 alkyl and C2-C4 alkenyl. In a still further aspect, $R^{10}$, when present, is selected from methyl, ethyl, n-propyl, isopropyl, ethenyl, n-propenyl, and isopropenyl. In yet a further aspect, $R^{10}$, when present, is selected from methyl, ethyl, and ethenyl.

In various aspects, $R^{10}$, when present, is C1-C20 alkyl. In a further aspect, $R^{10}$, when present, is C1-C16 alkyl. In a still further aspect, $R^{10}$, when present, is C1-C12 alkyl. In yet a further aspect, $R^{10}$, when present, is C1-C8 alkyl. In an even further aspect, $R^{10}$, when present, is C1-C4 alkyl. In a still further aspect, $R^{10}$, when present, is selected from methyl, ethyl, and n-propyl. In yet a further aspect, $R^{10}$, when present, is selected from methyl and ethyl. In an even further aspect, $R^{10}$, when present, is ethyl. In a still further aspect, $R^{10}$, when present, is methyl.

In various aspects, $R^{10}$, when present, is C2-C20 alkenyl. In a further aspect, $R^{10}$, when present, is C2-C16 alkenyl. In a still further aspect, $R^{10}$, when present, is C2-C12 alkenyl. In yet a further aspect, $R^{10}$, when present, is C2-C8 alkenyl. In an even further aspect, $R^{10}$, when present, is C2-C4 alkenyl. In a still further aspect, $R^{10}$, when present, is selected from ethenyl, n-propenyl, and isopropyl. In yet a further aspect, $R^{10}$, when present, is ethenyl.

d. $R^{11}$ Groups

In one aspect, $R^{11}$, when present, is an amino acid derivative side chain. Amino acid derivative side chains are well-known by those of skill in the art. See, for example, Tsume, et al. (2014) "The development of orally administrable gemcitabine prodrugs with D-enantiomer amino acid: Enhanced membrane permeability and enzymatic stability," *Eur. J. Pharm. Sci.* 86: 514-523; Zhang, et al. (2013) "A Carrier-Mediated Prodrug Approach To Improve the Oral Absorption of Antileukemic Drug Decitabine," *Mol. Pharmaceutics* 10: 3195-3202; Vig, et al. (2013) "Amino acids as promoities in prodrug design and development," *Adv. Drug Deliv. Rev.* 65: 1370-1385; Hasabelnaby, et al. (2012) "Synthesis, chemical and enzymatic hydrolysis, and aqueous solubility of amino acid ester prodrugs of 3-carboranyl thymidine analogs for boron neutron capture therapy of brain tumors," *Eur. J. Med. Chem.* 55: 325-334; Song, et al. (2005) "Amino acid ester prodrug of the anticancer agent gemcitabine: Synthesis, bioconversion, metabolic bioevasion and hPEPT1-mediated transport," *Mol. Pharm.* 2: 157-167; Landowski, et al. (2005) "Targeted delivery to PEPT1-overexpresssing cells: Acidic, basic, and secondary floxuridine amino acid ester prodrugs," *Mol. Cancer Ther.* 4: 659-667; Landowski, et al. (2005) "Floxuridine amino acid ester prodrugs: Enhancing Caco-2 permeability and resistance to glycosidic bond metabolism," *Pharm. Res.* 22: 1510-1518; Sugawara, et al. (2000) "Transport of valganciclovir, a ganciclovir prodrug, via peptide transporters PEPT1 and PEPT2," *J. Pharm. Sci.* 89: 781-789; Guo, et al. (1999) "Interactions of a nonpeptidic drug, valacyclovir, with the human intestinal peptide transporter (hPEPT1) expressed in a mammalian cell line," *J. Pharmacol. Exp. Ther.* 289: 448-454; Balimane, et al. (1998) "Direct evidence for peptide transporter (PepT1)-mediated uptake of a nonpeptide prodrug, valacyclovir," *Biochem. Biophys. Res. Commun.* 250: 246-251; de Vrueh, et al. (1998) "Transport of Lvalineacyclovir via the oligopeptide transporter in the human intestinal cell line, Caco-2," *J. Pharmacol. Exp. Ther.* 286: 1166-1170.

In various aspects, the amino acid derivative side chain can be a derivative of a synthetic or naturally-occurring amino acid. Thus, in a further aspect, the amino acid is a synthetic amino acid. In a still further aspect, the amino acid is a naturally-occurring amino acid. Examples of naturally-occurring amino acids include, but are not limited to, arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan.

In various further aspects, the amino acid derivative side chain is a derivative of alanine, valine, isoleucine, leucine, methionine, phenylalanine, tyrosine, or tryptophan. In a still further aspect, the amino acid derivative side chain is a derivative of alanine, valine, isoleucine, or leucine. In yet a further aspect, the amino acid derivative side chain is a derivative of isoleucine or leucine.

e. $R^{12}$ Groups

In one aspect, $R^{12}$, when present, is selected from C1-C6 alkyl and C3-C6 cycloalkyl. In a further aspect, $R^{12}$, when present, is selected from C1-C4 alkyl and C3-C4 cycloalkyl. In a still further aspect, $R^{12}$, when present, is selected from methyl, ethyl, n-propyl, isopropyl, and cyclopropyl.

In various aspects, $R^{12}$, when present, is C1-C6 alkyl. In a further aspect, $R^2$, when present, is C1-C4 alkyl. In a still further aspect, $R^{12}$, when present, is selected from methyl, ethyl, n-propyl, and isopropyl. In yet a further aspect, $R^{12}$, when present, is selected from methyl and ethyl. In an even further aspect, $R^{12}$, when present, is ethyl. In a still further aspect, $R^{12}$, when present, is methyl.

In various aspects, $R^{12}$, when present, is selected from cyclopropyl, cyclobutyl, cyclopentyl, and cyclohexyl. In a further aspect, $R^{12}$, when present, is selected from cyclopropyl, cyclobutyl, and cyclopentyl. In a still further aspect, $R^{12}$, when present, is selected from cyclopropyl and cyclobutyl. In yet a further aspect, $R^{12}$, when present, is cyclopropyl.

f. $R^{13}$ Groups

In one aspect, $R^{13}$, when present, is selected from C1-C8 alkyl, C3-C8 cycloalkyl, $Ar^2$, and —$CH_2Ar^2$. In a further aspect, $R^{13}$, when present, is selected from C1-C4 alkyl, C3-C6 cycloalkyl, $Ar^2$, and —$CH_2Ar^2$. In a still further aspect, $R^{13}$, when present, is selected from methyl, ethyl, n-propyl, isopropyl, cyclopropyl, cyclobutyl, $Ar^2$, and —$CH_2Ar^2$. In yet a further aspect, $R^{13}$, when present, is selected from methyl, ethyl, cyclopropyl, $Ar^2$, and —$CH_2Ar^2$.

In various aspects, $R^{13}$, when present, is selected from C1-C8 alkyl and C3-C8 cycloalkyl. In a further aspect, $R^{13}$, when present, is selected from C1-C4 alkyl, C3-C6 cycloalkyl. In a still further aspect, $R^{13}$, when present, is selected from methyl, ethyl, n-propyl, isopropyl, cyclopropyl, and cyclobutyl. In yet a further aspect, $R^{13}$, when present, is selected from methyl, ethyl, cyclopropyl.

In various aspects, $R^{13}$, when present, is C1-C8 alkyl. In a further aspect, $R^{13}$, when present, is C1-C4 alkyl. In a still further aspect, $R^{13}$, when present, is selected from methyl, ethyl, n-propyl, and isopropyl. In yet a further aspect, $R^{13}$, when present, is selected from methyl and ethyl. In an even further aspect, $R^{13}$, when present, is ethyl. In a still further aspect, $R^{13}$, when present, is methyl.

In various aspects, $R^{13}$, when present, is C3-C8 cycloalkyl. In a further aspect, $R^{13}$, when present, is selected from cyclopropyl, cyclobutyl, cyclopentyl, and cyclohexyl. In a still further aspect, $R^{13}$, when present, is selected from cyclopropyl, cyclobutyl, and cyclopentyl. In yet a further aspect, $R^{13}$, when present, is selected from cyclopropyl and cyclobutyl. In an even further aspect, $R^{13}$, when present, is selected from cyclopropyl.

In various aspects, $R^{13}$, when present, is selected from $Ar^2$ and —$CH_2Ar^2$. In a further aspect, $R^{13}$, when present, is $Ar^2$. In a still further aspect, $R^{13}$, when present, is —$CH_2Ar^2$.

g. $R^{14a}$ and $R^{14b}$ Groups

In one aspect, each of $R^{14a}$ and $R^{14b}$, when present, is independently selected from hydrogen and C1-C8 alkyl. In a further aspect, each of $R^{14a}$ and $R^{14b}$, when present, is independently selected from hydrogen and C1-C6 alkyl. In a still further aspect, each of $R^{14a}$ and $R^{14b}$, when present, is independently selected from hydrogen, methyl, ethyl, n-propyl, isopropyl, n-butyl, isobutyl, sec-butyl, and tert-butyl. In yet a further aspect, each of $R^{14a}$ and $R^{14b}$, when present, is independently selected from hydrogen, methyl, ethyl, n-propyl, and isopropyl. In an even further aspect, each of $R^{14a}$ and $R^{14b}$, when present, is independently selected from hydrogen, methyl, and ethyl. In a still further aspect, each of $R^{14a}$ and $R^{14b}$, when present, is independently selected from hydrogen and ethyl. In yet a further aspect, each of $R^{14a}$ and $R^{14b}$, when present, is independently selected from hydrogen and methyl.

In various aspects, each of $R^{14a}$ and $R^{14b}$, when present, is independently C1-C8 alkyl. In a further aspect, each of $R^{14a}$ and $R^{14b}$, when present, is independently C1-C6 alkyl. In a still further aspect, each of $R^{14a}$ and $R^{14b}$, when present, is independently selected from methyl, ethyl, n-propyl, isopropyl, n-butyl, isobutyl, sec-butyl, and tert-butyl. In yet a further aspect, each of $R^{14a}$ and $R^{14b}$, when present, is independently selected from methyl, ethyl, n-propyl, and isopropyl. In an even further aspect, each of $R^{14a}$ and $R^{14b}$, when present, is independently selected from methyl and ethyl. In a still further aspect, each of $R^{14a}$ and $R^{14b}$, when present, is ethyl. In yet a further aspect, each of $R^{14a}$ and $R^{14b}$, when present, is methyl.

In various aspects, each of $R^{14a}$ and $R^{14b}$, when present, is hydrogen.

h. $R^{15}$ Groups

In one aspect, $R^{15}$, when present, is selected from hydrogen, —C(O)(C1-C20 alkyl), —C(O)(C3-C6 cycloalkyl), and —C(O)(C2-C20 alkenyl). In a further aspect, $R^{15}$, when present, is selected from hydrogen, —C(O)(C1-C16 alkyl), and —C(O)(C2-C16 alkenyl). In a still further aspect, $R^{15}$, when present, is selected from hydrogen, —C(O)(C1-C12 alkyl), and —C(O)(C2-C12 alkenyl). In yet a further aspect, $R^{15}$, when present, is selected from hydrogen, —C(O)(C1-C8 alkyl), and —C(O)(C2-C8 alkenyl). In an even further aspect, $R^{15}$, when present, is selected from hydrogen, —C(O)(C1-C4 alkyl), and —C(O)(C2-C4 alkenyl). In a still further aspect, $R^{15}$, when present, is selected from hydrogen, —C(O)CH$_3$, —C(O)CH$_2$CH$_3$, —C(O)CH$_2$CH$_2$CH$_3$, —C(O)(CH)(CH$_3$)$_2$, —C(O)CH=CH$_2$, —C(O)CH=CHCH$_3$, —C(O)CH$_2$CH=CH$_2$, and —C(O)(CH$_3$)C=CH$_2$. In yet a further aspect, $R^{15}$, when present, is selected from hydrogen, —C(O)CH$_3$, —C(O)CH$_2$CH$_3$, and —C(O)CH=CH$_2$.

In various aspects, $R^{15}$, when present, is selected from hydrogen and —C(O)(C1-C20 alkyl). In a further aspect, $R^{15}$, when present, is selected from hydrogen and —C(O)(C1-C16 alkyl). In a still further aspect, $R^{15}$, when present, is selected from hydrogen and —C(O)(C1-C12 alkyl). In yet a further aspect, $R^{15}$, when present, is selected from hydrogen and —C(O)(C1-C8 alkyl). In an even further aspect, $R^{15}$, when present, is selected from hydrogen and —C(O)(C1-C4 alkyl). In a still further aspect, $R^{15}$, when present, is selected from hydrogen, —C(O)CH$_3$, —C(O)CH$_2$CH$_3$, —C(O)CH$_2$CH$_2$CH$_3$, and —C(O)(CH)(CH$_3$)$_2$. In yet a further aspect, $R^{15}$, when present, is selected from hydrogen, —C(O)CH$_3$, and —C(O)CH$_2$CH$_3$. In an even further aspect, $R^{15}$, when present, is selected from hydrogen and —C(O)CH$_3$.

In various aspects, $R^{15}$, when present, is —C(O)(C1-C20 alkyl). In a further aspect, $R^{15}$, when present, is —C(O)(C1-C16 alkyl). In a still further aspect, $R^{15}$, when present, is —C(O)(C1-C12 alkyl). In yet a further aspect, $R^{15}$, when present, is —C(O)(C1-C8 alkyl). In an even further aspect, $R^{15}$, when present, is —C(O)(C1-C4 alkyl). In a still further aspect, $R^{15}$, when present, is selected from —C(O)CH$_3$, —C(O)CH$_2$CH$_3$, —C(O)CH$_2$CH$_2$CH$_3$, and —C(O)(CH)(CH$_3$)$_2$. In yet a further aspect, $R^{15}$, when present, is selected from —C(O)CH$_3$ and —C(O)CH$_2$CH$_3$. In an even further aspect, $R^{15}$, when present, is —C(O)CH$_3$.

In various aspects, $R^{15}$, when present, is selected from hydrogen and —C(O)(C2-C20 alkenyl). In a further aspect, $R^{15}$, when present, is selected from hydrogen and —C(O)(C2-C16 alkenyl). In a still further aspect, $R^{15}$, when present, is selected from hydrogen and —C(O)(C2-C12 alkenyl). In yet a further aspect, $R^{15}$, when present, is selected from hydrogen and —C(O)(C2-C8 alkenyl). In an even further aspect, $R^{15}$, when present, is selected from hydrogen and —C(O)(C2-C4 alkenyl). In a still further aspect, $R^{15}$, when present, is selected from hydrogen, —C(O)CH=CH$_2$, —C(O)CH=CHCH$_3$, —C(O)CH$_2$CH=CH$_2$, and —C(O)(CH$_3$)C=CH$_2$. In yet a further aspect, $R^{15}$, when present, is selected from hydrogen and —C(O)CH=CH$_2$.

In various aspects, $R^{13}$, when present, is —C(O)(C2-C20 alkenyl). In a further aspect, $R^{15}$, when present, is —C(O)(C2-C16 alkenyl). In a still further aspect, $R^{15}$, when present, is —C(O)(C2-C12 alkenyl). In yet a further aspect, $R^{15}$, when present, is —C(O)(C2-C8 alkenyl). In an even further aspect, $R^{15}$, when present, is —C(O)(C2-C4 alkenyl). In a still further aspect, $R^{15}$, when present, is selected from —C(O)CH=CH$_2$, —C(O)CH=CHCH$_3$, —C(O)

CH$_2$CH=CH$_2$, and —C(O)(CH$_3$)C=CH$_2$. In yet a further aspect, R$^{15}$, when present, is —C(O)CH=CH$_2$.

In various aspects, R$^{13}$, when present, is —C(O)(C3-C6 cycloalkyl). In a further aspect, R$^{15}$, when present, is selected from —C(O)(cyclopropyl), —C(O)(cyclobutyl), and —C(O)(cyclopentyl). In a still further aspect, R$^{15}$, when present, is selected from —C(O)(cyclopropyl) and —C(O)(cyclobutyl). In yet a further aspect, R$^{15}$, when present, is —C(O)(cyclobutyl). In an even further aspect, R$^{15}$, when present, is —C(O)(cyclopropyl).

In various aspects, R$^{13}$, when present, is hydrogen.

i. Ar$^1$ Groups

In one aspect, Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Ar$^1$, when present, is selected from C6-C14 aryl and C2-C10 heteroaryl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar$^1$, when present, is selected from C6-C14 aryl and C2-C10 heteroaryl, and is substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar$^1$, when present, is selected from C6-C14 aryl and C2-C10 heteroaryl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar$^1$, when present, is selected from C6-C14 aryl and C2-C10 heteroaryl, and is unsubstituted.

In various aspects, Ar$^1$, when present, is C6-C14 aryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, Ar$^1$, when present, is C6-C14 aryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar$^1$, when present, is C6-C14 aryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar$^1$, when present, is C6-C14 aryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar$^1$, when present, is unsubstituted C6-C14 aryl.

In various aspects, Ar$^1$, when present, is C2-C10 heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, furanyl, thiophenyl, pyrrolyl, pyrazolyl, imidazolyl, triazolyl, oxazolyl, thiazolyl, pyridinyl, pyrimidinyl, imidazolyl, purinyl, indolyl, and quinolinyl. In a further aspect, Ar$^1$, when present, is C2-C10 heteroaryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar$^1$, when present, is C2-C10 heteroaryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar$^1$, when present, is C2-C10 heteroaryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar$^1$, when present, is unsubstituted C2-C10 heteroaryl.

j. Ar$^2$ Groups

In one aspect, Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Ar$^2$, when present, is selected from C6-C14 aryl and C2-C10 heteroaryl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar$^2$, when present, is selected from C6-C14 aryl and C2-C10 heteroaryl, and is substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar$^2$, when present, is selected from C6-C14 aryl and C2-C10 heteroaryl, and is monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar², when present, is selected from C6-C14 aryl and C2-C10 heteroaryl, and is unsubstituted.

In various aspects, Ar², when present, is C6-C14 aryl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, anthracenyl, and phenanthrenyl. In a further aspect, Ar², when present, is C6-C14 aryl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar², when present, is C6-C14 aryl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar², when present, is C6-C14 aryl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar², when present, is unsubstituted C6-C14 aryl.

In various aspects, Ar², when present, is C2-C10 heteroaryl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, furanyl, thiophenyl, pyrrolyl, pyrazolyl, imidazolyl, triazolyl, oxazolyl, thiazolyl, pyridinyl, pyrimidinyl, imidazolyl, purinyl, indolyl, and quinolinyl. In a further aspect, Ar², when present, is C2-C10 heteroaryl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Ar², when present, is C2-C10 heteroaryl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Ar², when present, C2-C10 heteroaryl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Ar², when present, is unsubstituted C2-C10 heteroaryl.

2. Example Compounds

In one aspect, a compound can be present as one or more of the following structures:

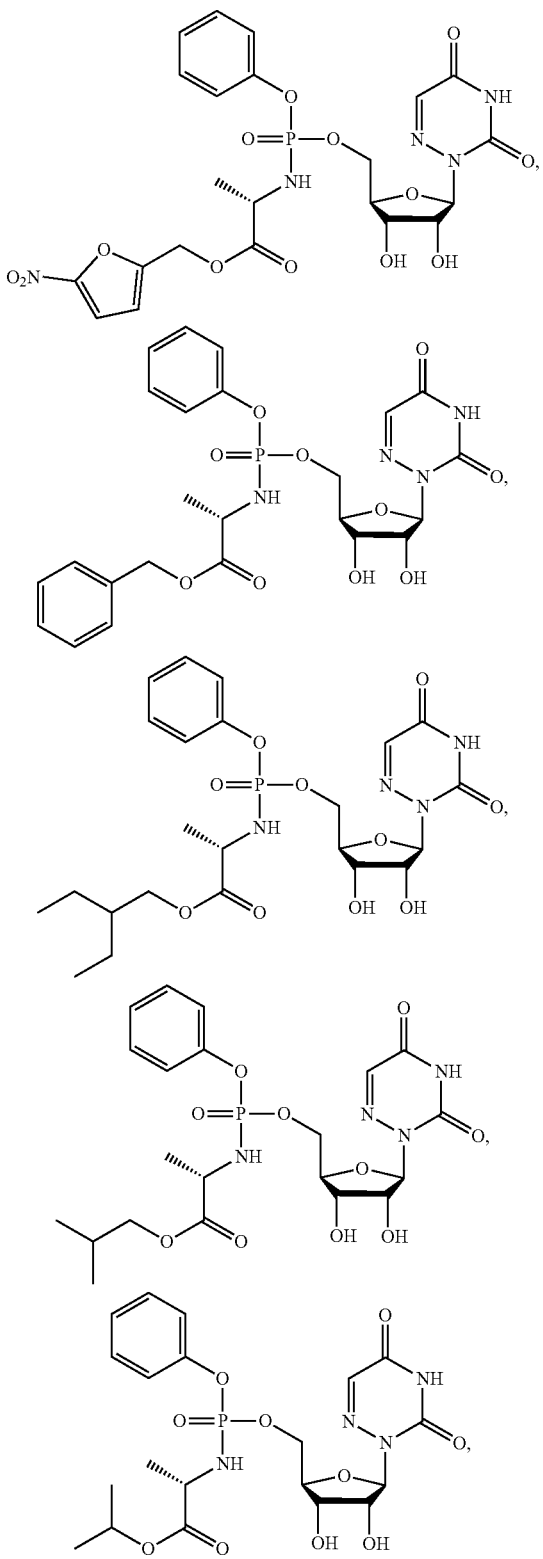

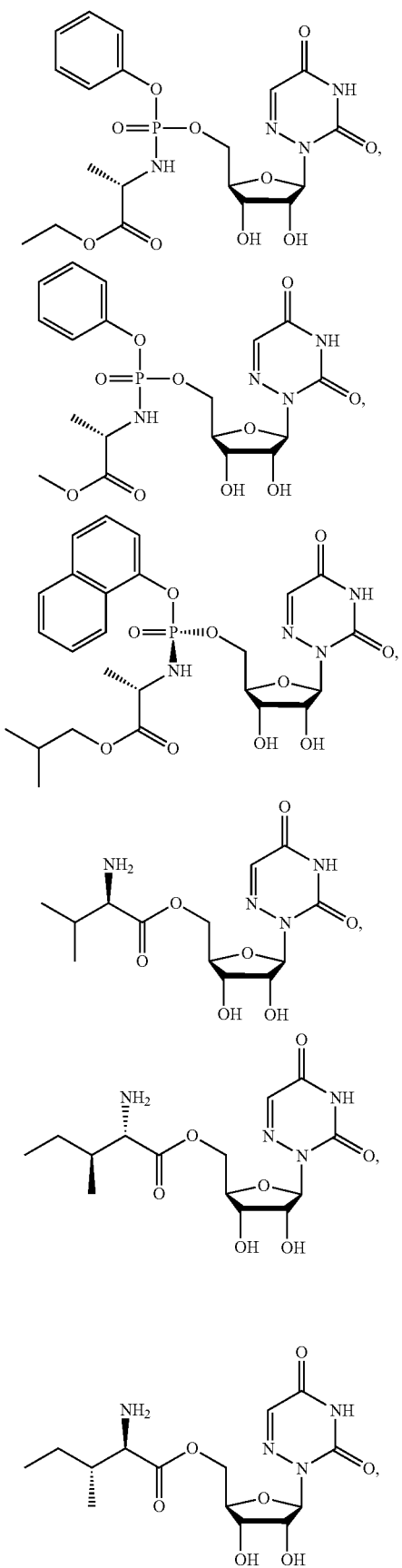
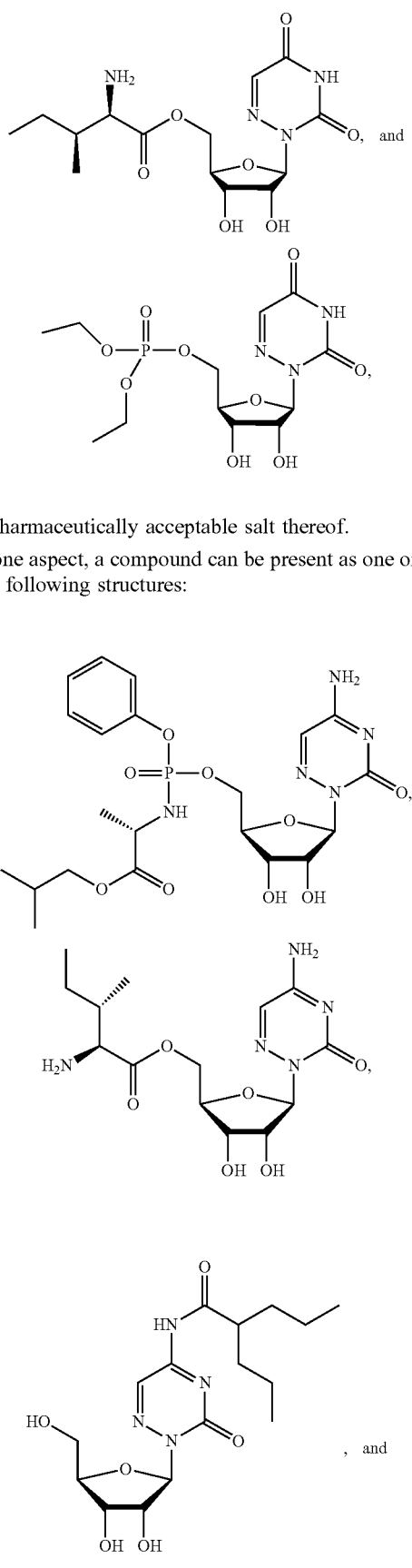
or a pharmaceutically acceptable salt thereof.
In one aspect, a compound can be present as one or more of the following structures:

-continued

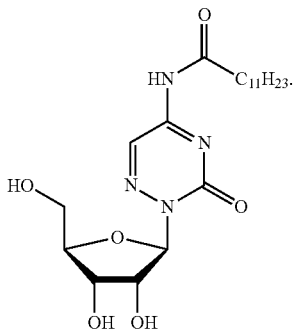

or a pharmaceutically acceptable salt thereof.

In one aspect, a compound can be present as one or more of the following structures:

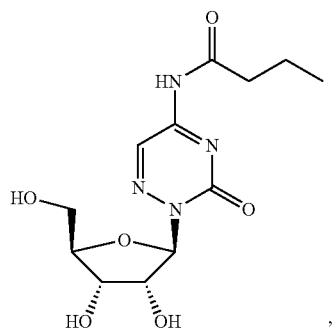

,

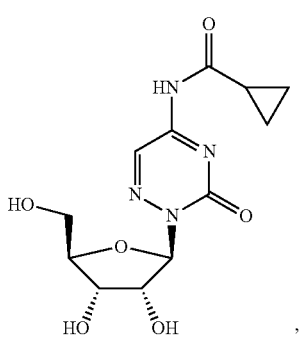

,

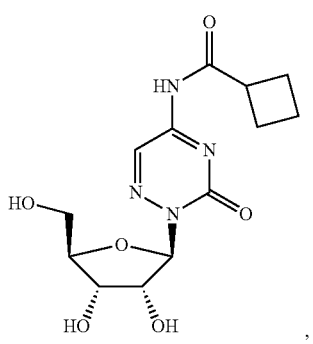

,

-continued

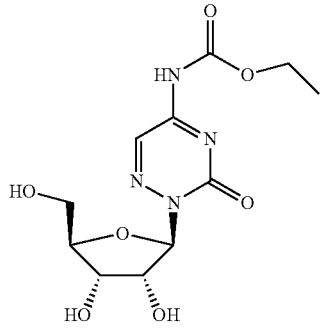

, and

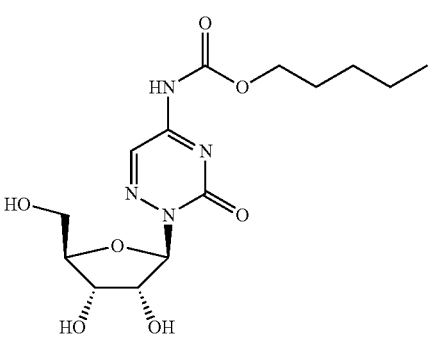

or a pharmaceutically acceptable salt thereof.

In one aspect, a compound can be present as the following structure:

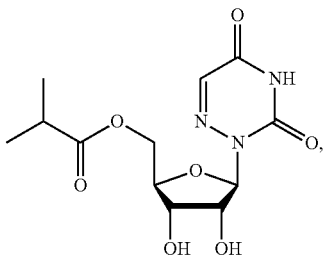

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of a viral infection, and such activity can be determined using the assay methods described herein below.

In one aspect, a compound can be selected from:

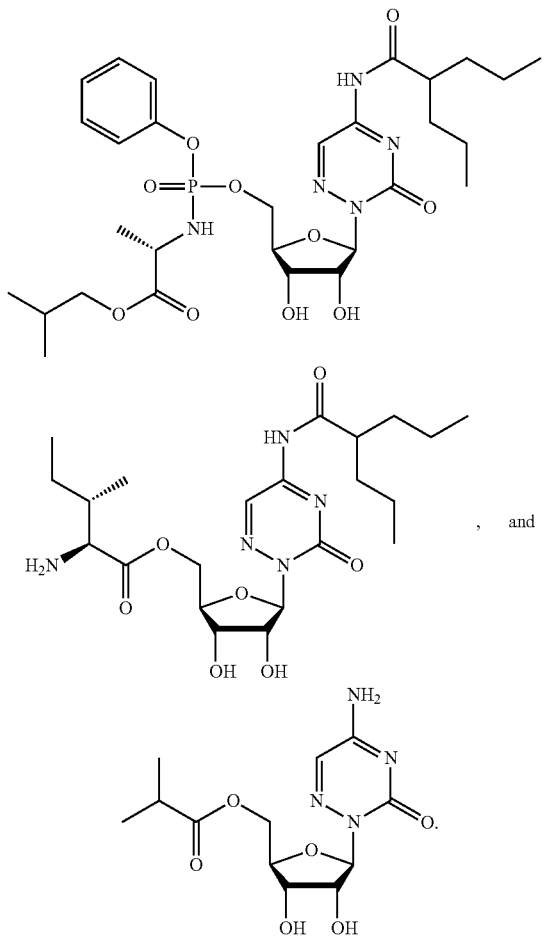

, and

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. PHARMACEUTICAL COMPOSITIONS

In one aspect, disclosed are pharmaceutical compositions comprising a disclosed compound, or a pharmaceutically acceptable salt thereof and a pharmaceutically acceptable carrier.

In one aspect, disclosed are pharmaceutical compositions comprising pharmaceutically acceptable carrier and a therapeutically effective amount of at least one compound having a structure represented by a formula:

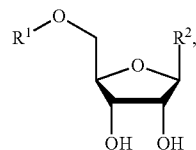

wherein $R^1$ is selected from hydrogen, —C(O)$R^{10}$, —C(O)CH($R^{11}$)NH$_2$, —P(O)(OAr$^1$)NHCH($R^{12}$)CO$_2$$R^{13}$, and —P(O)(OR$^{14a}$)(OR$^{14b}$); wherein $R^{10}$, when present, is selected from C1-C20 alkyl and C2-C20 alkenyl; wherein $R^{11}$, when present, is an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

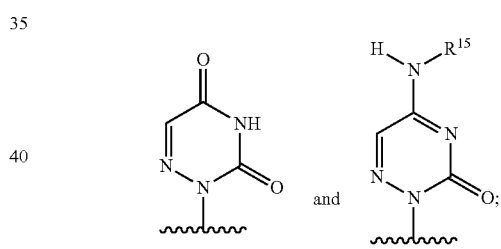

and wherein $R^{15}$, when present, is selected from hydrogen, —C(O)(C1-C20 alkyl), and —C(O)(C2-C20 alkenyl), provided that when $R^2$ is

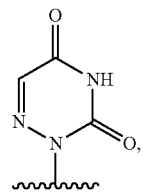

then $R^1$ is —C(O)CH($R^{11}$)NH$_2$— P(O)(OAr$^1$)NHCH($R^{12}$)CO$_2$$R^{13}$, or —P(O)(OR$^{14a}$)(OR$^{14b}$), and provided that when $R^1$ is hydrogen, then $R^{15}$ is —C(O)(C1-C20 alkyl), —C(O)(C3-C6 cycloalkyl) or —C(O)(C2-C20 alkenyl), or a pharmaceutically acceptable salt thereof.

In one aspect, disclosed are pharmaceutical compositions comprising pharmaceutically acceptable carrier and a therapeutically effective amount of at least one compound having a structure:

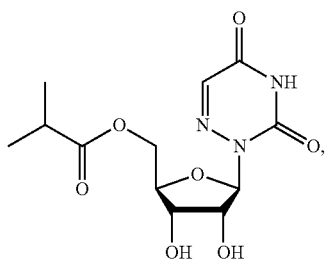

or a pharmaceutically acceptable salt thereof.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a viral infection such as, for example, chikungunya, Venezuelan equine encephalitis, dengue, influenza, and zika.

It is understood that the disclosed compositions can be prepared from the disclosed compounds. It is also understood that the disclosed compositions can be employed in the disclosed methods of using.

D. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-VII, as described and exemplified below. The following examples are provided so that the invention might be more fully understood, are illustrative only, and should not be construed as limiting.

1. Route I

In one aspect, substituted 6-aza nucleoside prodrugs can be prepared as shown below.

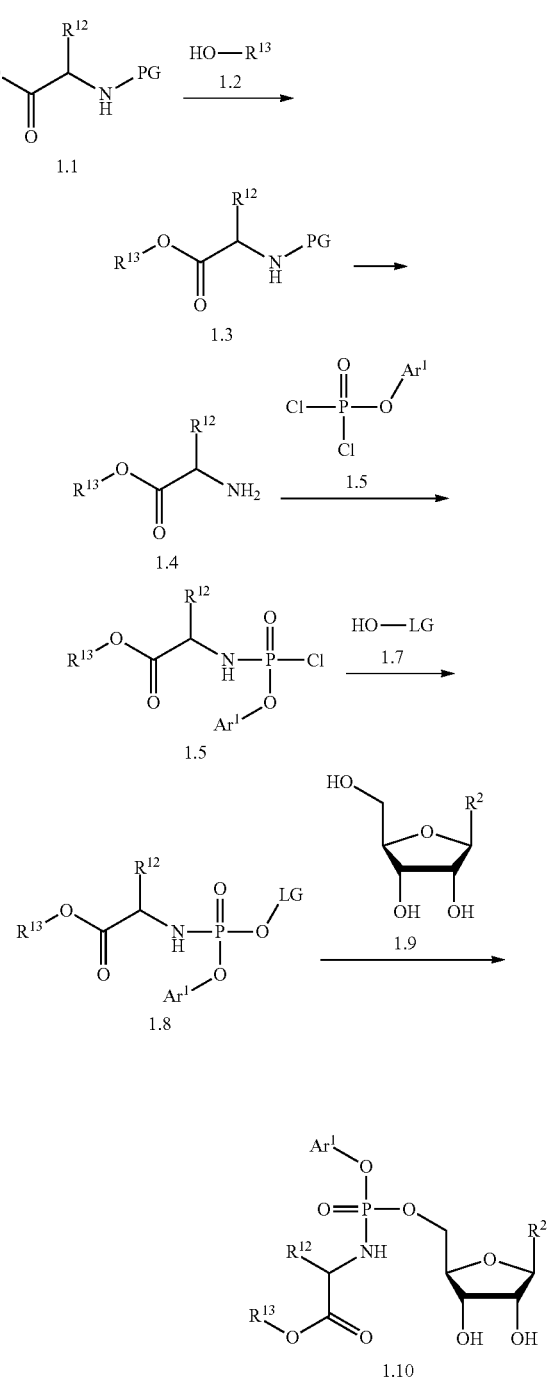

SCHEME 1A.

Compounds are represented in generic form, where PG is an amine protecting group, LG is a leaving group, and with other substituents as noted in compound descriptions elsewhere herein. A more specific example is set forth below.

SCHEME 1B.

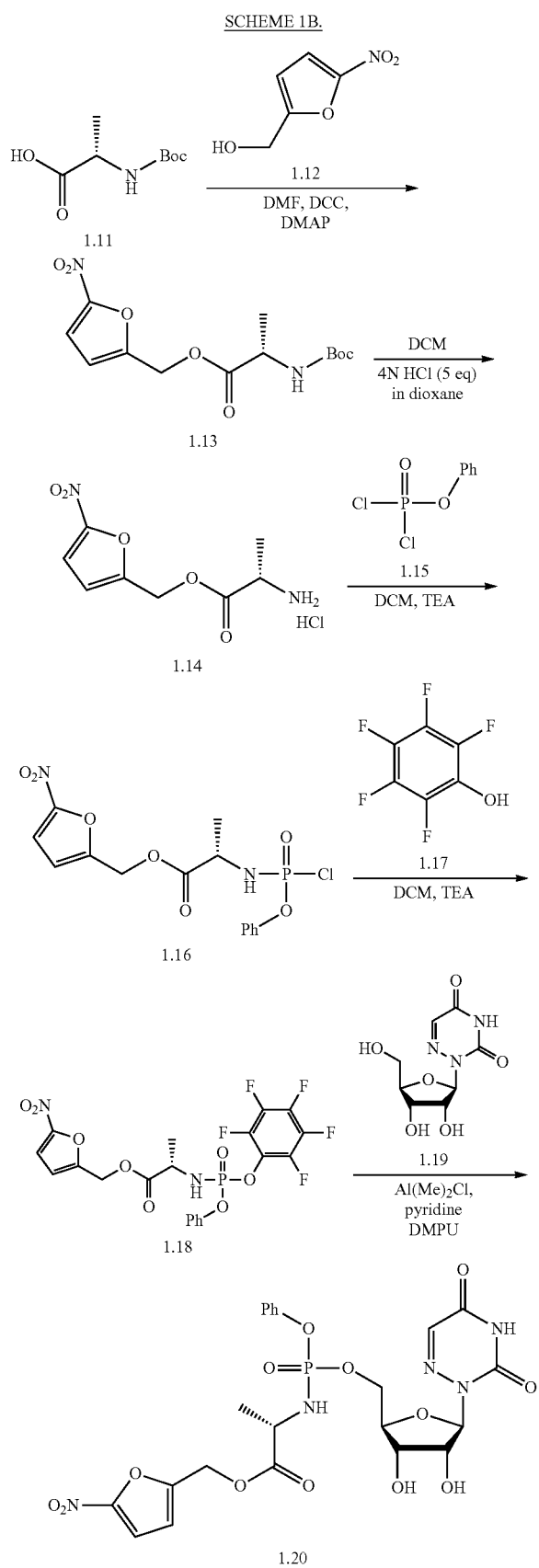

In one aspect, compounds of type 1.20, and similar compounds, can be prepared according to reaction Scheme 1B above. Thus, compounds of type 1.13 can be prepared by coupling an appropriate carboxylic acid, e.g., 1.11 as shown above, and an appropriate alcohol, e.g., 1.12 as shown above. Appropriate carboxylic acids and appropriate alcohols are commercially available or prepared by methods known to one skilled in the art. The coupling reaction is carried out in the presence of an appropriate coupling agent, e.g., N,N'-dicyclohexylcarbodiimide (DCC), and an appropriate activating agent, e.g., 4-dimethylaminopyridine (DMAP), in an appropriate solvent, e.g., dimethylformamide (DMF). Compounds of type 1.14 can be prepared deprotection of an appropriate amine, e.g., 1.13 as shown above. The deprotection is carried out in the presence of an appropriate deprotecting agent, e.g., 4N HCl (5 eq) in dioxange, in an appropriate solvent, e.g., dichloromethane (DCM). Compounds of type 1.16 can be prepared by coupling reaction of an appropriate amine, e.g., 1.14 as shown above, and an appropriate phosphoryl chloride, e.g., 1.15 as shown above. Appropriate phosphoryl chlorides are commercially available or prepared by methods known to one skilled in the art. The coupling reaction is carried out in the presence of an appropriate base, e.g., triethylamine (TEA), in an appropriate solvent, e.g., DCM. Compounds of type 1.18 can be prepared by activation of an appropriate organophosphorous compound, e.g., 1.16 as shown above. Appropriate organophosphorous compounds are commercially available or prepared by methods known to one skilled in the art. The activation is carried out in the presence of an appropriate alcohol, e.g., 1.17 as shown above, in the presence of an appropriate base, e.g., TEA, in an appropriate solvent, e.g., DCM. Appropriate alcohols are commercially available or prepared by methods known to one skilled in the art. Compounds of type 1.20 can be prepared by displacement of a leaving group on an appropriate activated organophosphorous compound, e.g., 1.18 as shown above. The displacement reaction is carried out in the presence of an appropriate primary alcohol, e.g., 1.19 as shown above, an appropriate Lewis acid, e.g., trimethylaluminum, and an appropriate base, e.g., pyridine, in an appropriate solvent, e.g., N,N'-dimethylpropyleneurea (DMPU). Appropriate primary alcohols are commercially available or prepared by methods known to one skilled in the art. As can be appreciated by one skilled in the art, the above reaction provides an example of a generalized approach wherein compounds similar in structure to the specific reactants above (compounds similar to compounds of type 1.1, 1.2, 1.3, 1.4, 1.5, 1.6, 1.7, 1.8, and 1.9), can be substituted in the reaction to provide substituted 6-aza nucoleoside prodrug derivatives similar to Formula 1.10.

2. Route II

In one aspect, substituted 6-aza nucoleoside prodrugs can be prepared as shown below.

SCHEME 2A

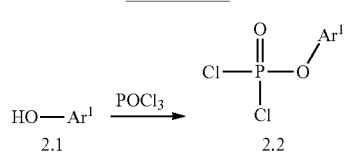

Compounds are represented in generic form, with substituents as noted in compound descriptions elsewhere herein. A more specific example is set forth below.

SCHEME 2B.

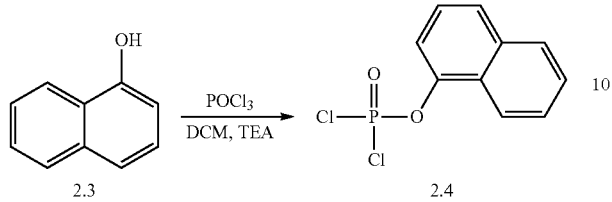

In one aspect, compounds of type 2.4, and similar compounds, can be prepared according to reaction Scheme 2B above. Thus, compounds of type 2.4 can be prepared by hydrolysis of an appropriate aryl alcohol, e.g., 2.3 as shown above. Appropriate aryl alcohols are commercially available or prepared by methods known to one skilled in the art. The hydrolysis is carried out in the presence of an appropriate hydrolysing agent, e.g., phosphorus oxychloride, and an appropriate base, e.g., TEA, in an appropriate solvent, e.g., DCM. As can be appreciated by one skilled in the art, the above reaction provides an example of a generalized approach wherein compounds similar in structure to the specific reactants above (compounds similar to compounds of type 2.1), can be substituted in the reaction to provide substituted 6-aza nucleoside prodrug derivatives similar to Formula 2.2.

3. Route III

In one aspect, substituted 6-aza nucleoside prodrugs can be prepared as shown below.

SCHEME 3A.

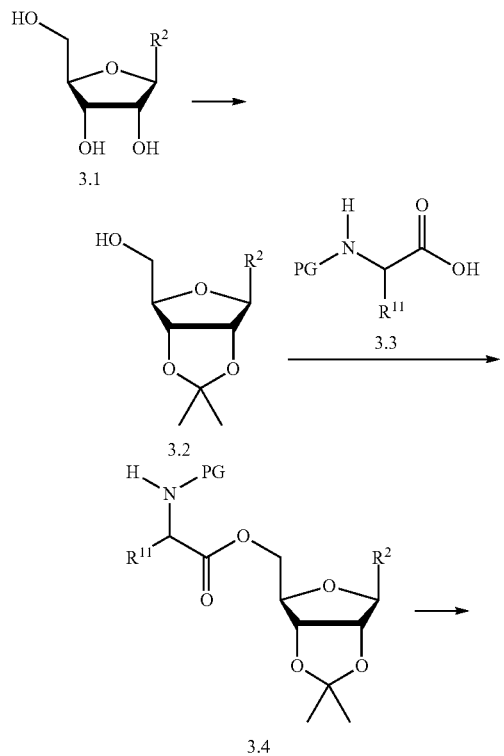

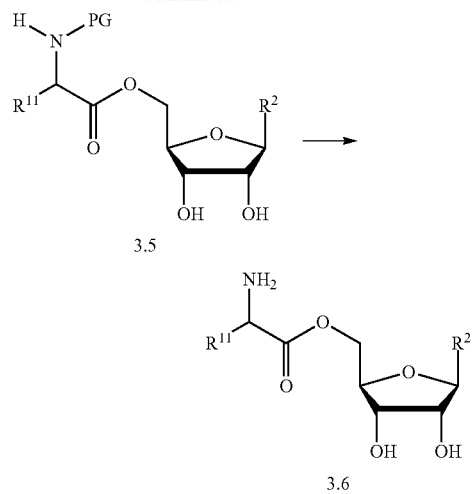

Compounds are represented in generic form, wherein PG is an amine protecting group, and with other substituents as noted in compound descriptions elsewhere herein. A more specific example is set forth below.

SCHEME 3B.

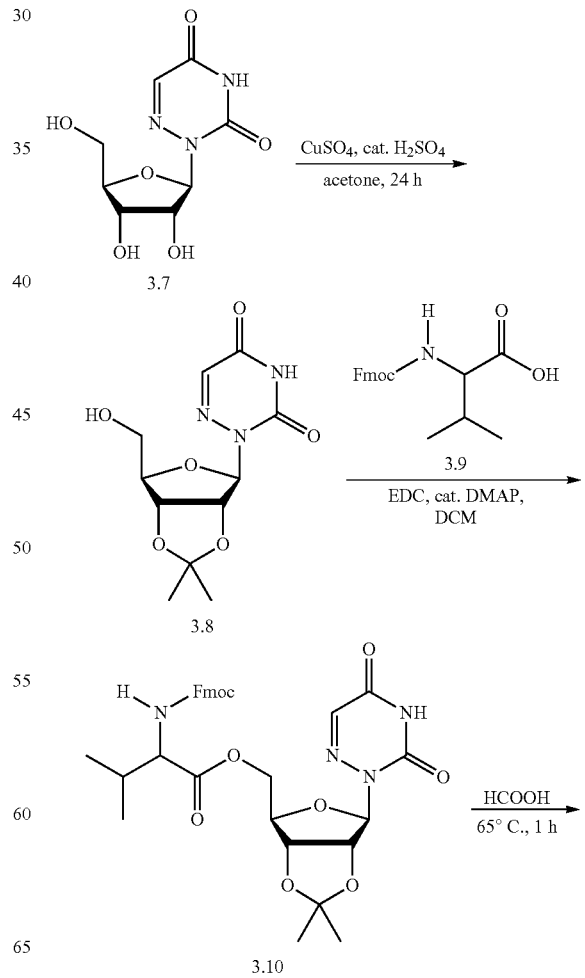

-continued

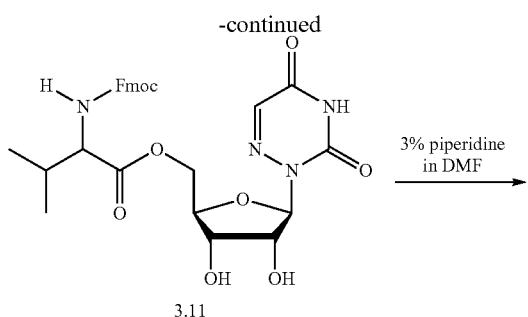

3.11

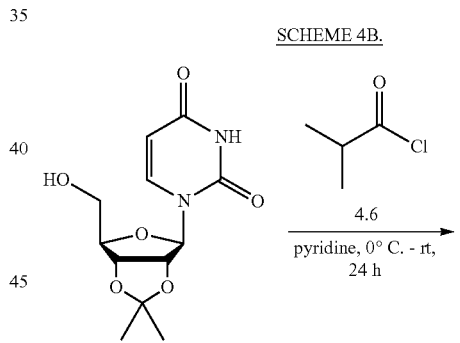

3.12

In one aspect, compounds of type 3.12, and similar compounds, can be prepared according to reaction Scheme 3B above. Thus, compounds of type 3.8 can be prepared by protection of an appropriate diol, e.g., 3.7 as shown above. Appropriate diols are commercially available or prepared by methods known to one skilled in the art. The protection is carried out in the presence of an appropriate catalyst, e.g., copper sulfate, an appropriate acid, e.g., catalytic sulphuric acid, in an appropriate solvent, e.g., acetone, for an appropriate period of time, e.g., 24 h. Compounds of type 3.10 can be prepared by coupling an appropriate alcohol, e.g., 3.8, and an appropriate carboxylic acid, e.g., 3.9 as shown above. Appropriate carboxylic acids are commercially available or prepared by methods known to one skilled in the art. The coupling reaction is carried out in the presence of an appropriate coupling agent, e.g., 1-ethyl-3-(3-dimethylaminopropyl)carbodiimide (EDC), and an appropriate activating agent, e.g., DMAP, in an appropriate solvent, e.g., DCM. Compounds of type 3.11 can be prepared by deprotection of an appropriate acetal, e.g., 3.10 as shown above. The deprotection reaction is carried out in the presence of an appropriate acid, e.g., acetic acid, at an appropriate temperature, e.g., 65° C., for an appropriate period of time, e.g., 1 h. Compounds of type 3.12 can be prepared by deprotection of an appropriate amine, e.g., 3.11 as shown above. The deprotection reaction is carried out in the presence of an appropriate base, e.g., 3% piperidine, in an appropriate solvent, e.g., DMF. As can be appreciated by one skilled in the art, the above reaction provides an example of a generalized approach wherein compounds similar in structure to the specific reactants above (compounds similar to compounds of type 3.1, 3.2, 3.3, 3.4, and 3.5), can be substituted in the reaction to provide substituted 6-aza nucleoside prodrug derivatives similar to Formula 3.6.

4. Route IV

In one aspect, substituted 6-aza nucleoside prodrugs can be prepared as shown below.

SCHEME 4A.

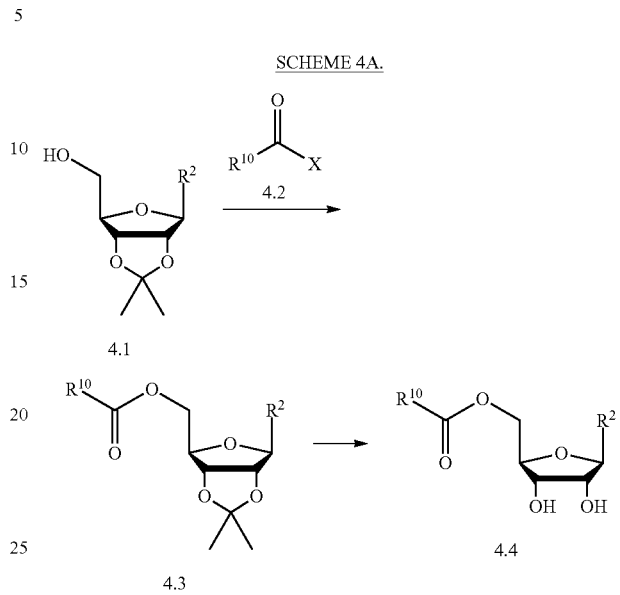

Compounds are represented in generic form, where X is a halogen, and with other substituents as noted in compound descriptions elsewhere herein. A more specific example is set forth below.

SCHEME 4B.

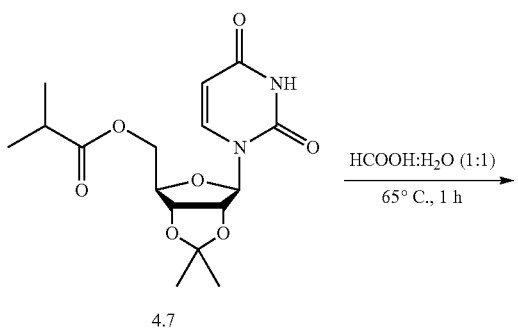

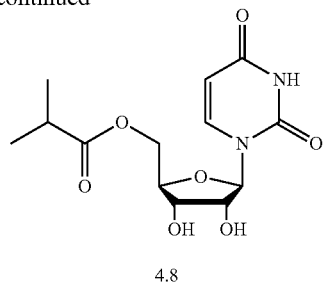

4.8

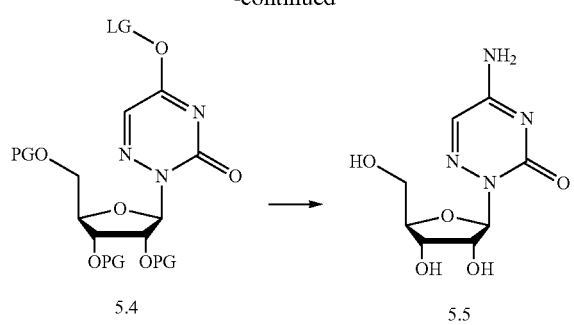

5.4

5.5

In one aspect, compounds of type 4.8, and similar compounds, can be prepared according to reaction Scheme 4B above. Thus, compounds of type 4.7 can be prepared by coupling an appropriate alcohol, e.g., 4.5 as shown above, and an appropriate acyl halide, e.g., 4.6 as shown above. Appropriate alcohols and appropriate acyl halides are commercially available or prepared by methods known to one skilled in the art. The coupling reaction is carried out in the presence of an appropriate base, e.g., pyridine, over an appropriate temperature range, e.g., 0° C. to rt, for an appropriate period of time, e.g., 24 h. Compounds of type 4.8 can be prepared by deprotection of an appropriate acetal, e.g., 4.7 as shown above. The deprotection reaction is carried out in the presence of an appropriate acid, e.g., acetic acid:water (1:1), at an appropriate temperature, e.g., 65° C., for an appropriate period of time, e.g., 1 h. As can be appreciated by one skilled in the art, the above reaction provides an example of a generalized approach wherein compounds similar in structure to the specific reactants above (compounds similar to compounds of type 4.1, 4.2, and 4.3), can be substituted in the reaction to provide substituted 6-aza nucoleoside prodrug derivatives similar to Formula 4.4.

5. Route V

In one aspect, substituted 6-aza nucoleoside prodrugs can be prepared as shown below.

Compounds are represented in generic form, where PG is a hydroxyl protecting group, X is a halogen, and LG is a leaving group, and with other substituents as noted in compound descriptions elsewhere herein. A more specific example is set forth below.

SCHEME 5A.

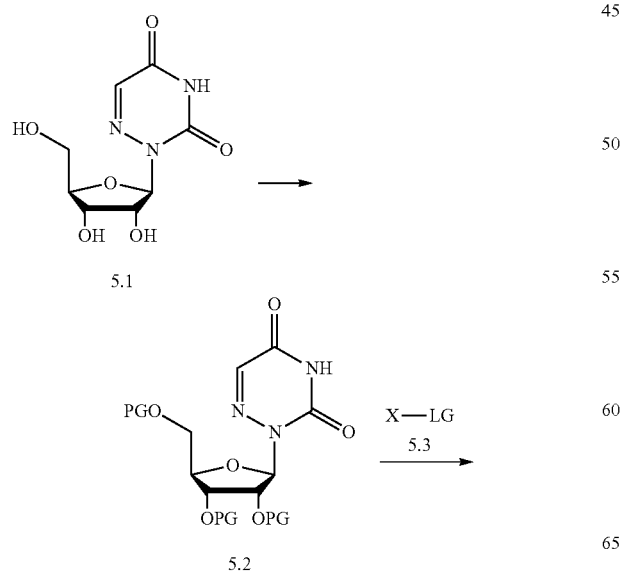

SCHEME 5B.

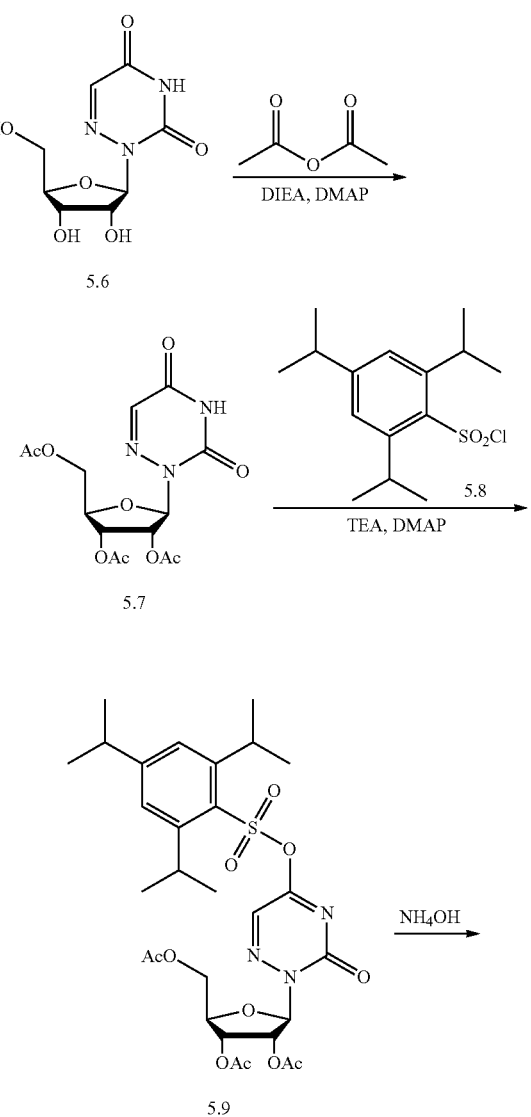

-continued

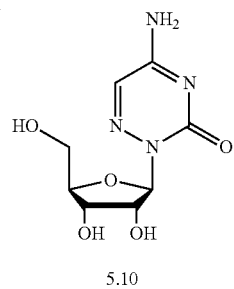

5.10

In one aspect, compounds of type 5.10, and similar compounds, can be prepared according to reaction Scheme 5B above. Thus, compounds of type 5.7 can be prepared by protection of an appropriate nucleoside, e.g., 5.6 as shown above. Appropriate nucleosides are commercially available or prepared by methods known to one skilled in the art or disclosed elsewhere herein. The protection is carried out in the presence of an appropriate protecting agent, e.g., acetic anhydride, and an appropriate base, e.g., DMAP, in an appropriate solvent, e.g., N,N-diisopropylethylamine. Compounds of type 5.9 can be prepared by activation of an appropriate pyrimidine, e.g., 5.7 as shown above. The activation is carried out in the presence of an appropriate activating agent, e.g., 5.8 as shown above, and an appropriate base, e.g., DMAP and TEA. Compounds of type 5.10 can be prepared by displacement and deprotection of an appropriate activated pyrimidine, e.g., 5.9 as shown above. The displacement/deprotection is carried out in the presence of an appropriate amine base, e.g., ammonium hydroxide as shown above. As can be appreciated by one skilled in the art, the above reaction provides an example of a generalized approach wherein compounds similar in structure to the specific reactants above (compounds similar to compounds of type 5.1, 5.2, 5.3, and 5.4), can be substituted in the reaction to provide substituted 6-aza nucoleoside prodrug derivatives similar to Formula 5.5.

6. Route VI

In one aspect, substituted 6-aza nucoleoside prodrugs can be prepared as shown below.

SCHEME 6A.

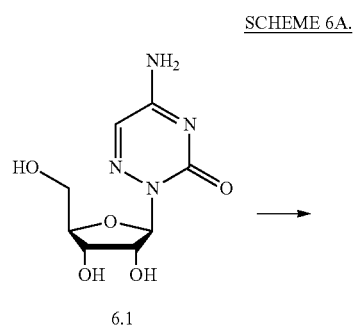

6.1

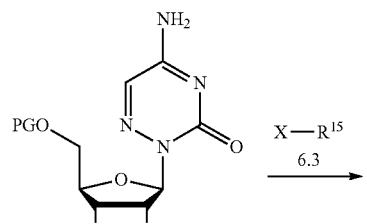

6.2

-continued

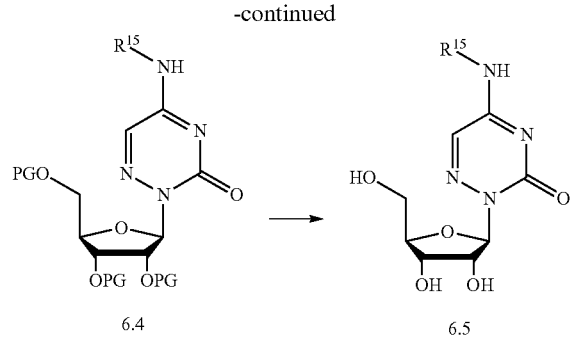

6.4        6.5

Compounds are represented in generic form, where PG is a hydroxyl protecting group, and with other substituents as noted in compound descriptions elsewhere herein. A more specific example is set forth below.

SCHEME 6B.

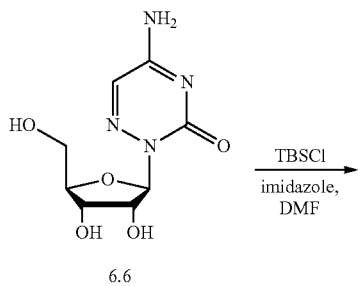

6.6

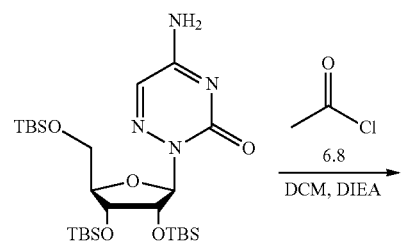

6.7

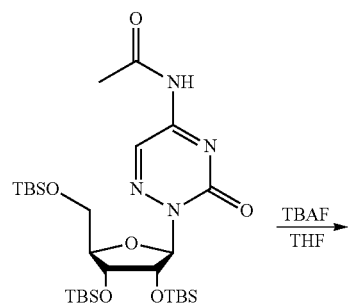

6.9

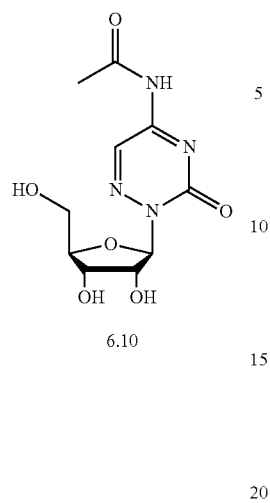

6.10

In one aspect, compounds of type 6.10, and similar compounds, can be prepared according to reaction Scheme 63 above. Thus, compounds of type 6.7 can be prepared by protection of an appropriate nucleoside, e.g., 6.7 as shown above. Appropriate nucleosides are commercially available or prepared by methods known to one skilled in the art. The protection is carried out in the presence of an appropriate protecting agent, e.g., tert-butyldimethylsilyl ether, and an appropriate base, e.g., imidazole, in an appropriate solvent, e.g., DMF. Compounds of type 6.9 can be prepared by acylation of an appropriate amine, e.g., 6.7 as shown above. The acylation is carried out in the presence of an appropriate acyl halide, e.g., 6.8 as shown above, and an appropriate base, e.g., N,N-diisopropylethylamine, in an appropriate base, e.g., DCM. Compounds of type 6.10 can be prepared by deprotection of an appropriate nucleoside, e.g., 6.9 as shown above. The deprotection is carried out in the presence of an appropriate deprotecting agent, e.g., tetra-n-butylammonium fluoride, in an appropriate solvent, e.g., tetrahydrofuran. As can be appreciated by one skilled in the art, the above reaction provides an example of a generalized approach wherein compounds similar in structure to the specific reactants above (compounds similar to compounds of type 6.1, 6.2, 6.3, and 6.4), can be substituted in the reaction to provide substituted 6-aza nucleoside prodrug derivatives similar to Formula 6.5.

7. Route VII

In one aspect, substituted 6-aza nucoleoside prodrugs can be prepared as shown below.

SCHEME 7A.

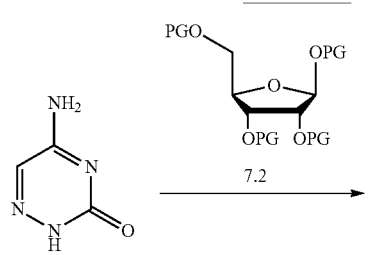

7.1

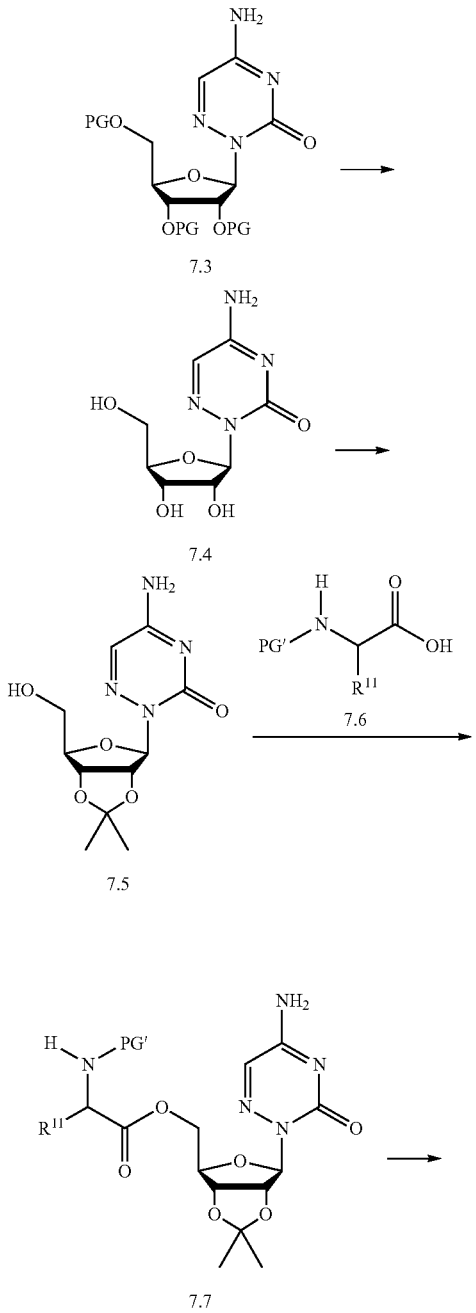

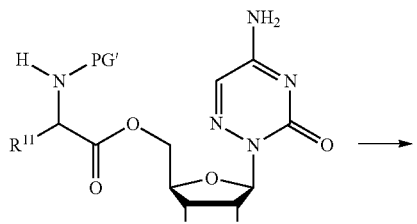

7.8

-continued

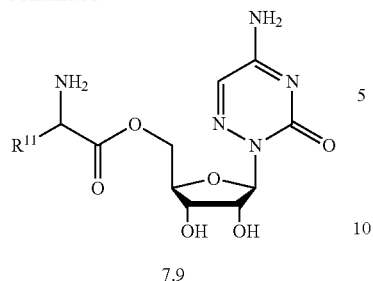

7.9

Compounds are represented in generic form, where PG is a hydroxyl protecting group, PG' is an amine protecting group, and with other substituents as noted in compound descriptions elsewhere herein. A more specific example is set forth below.

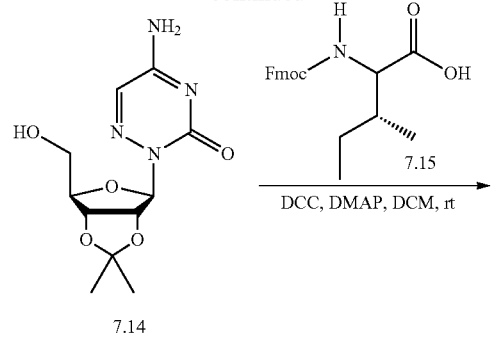

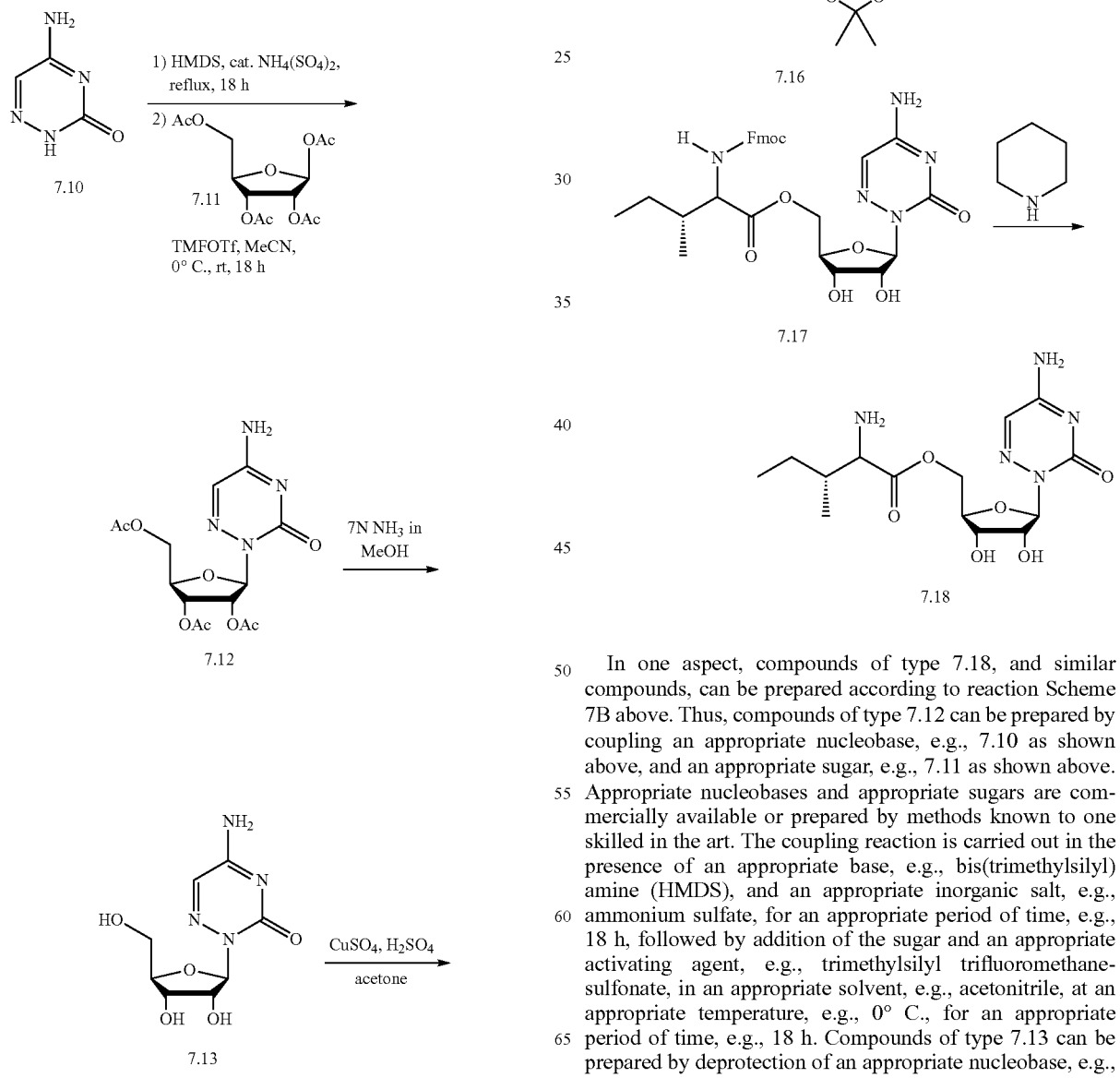

In one aspect, compounds of type 7.18, and similar compounds, can be prepared according to reaction Scheme 7B above. Thus, compounds of type 7.12 can be prepared by coupling an appropriate nucleobase, e.g., 7.10 as shown above, and an appropriate sugar, e.g., 7.11 as shown above. Appropriate nucleobases and appropriate sugars are commercially available or prepared by methods known to one skilled in the art. The coupling reaction is carried out in the presence of an appropriate base, e.g., bis(trimethylsilyl) amine (HMDS), and an appropriate inorganic salt, e.g., ammonium sulfate, for an appropriate period of time, e.g., 18 h, followed by addition of the sugar and an appropriate activating agent, e.g., trimethylsilyl trifluoromethanesulfonate, in an appropriate solvent, e.g., acetonitrile, at an appropriate temperature, e.g., 0° C., for an appropriate period of time, e.g., 18 h. Compounds of type 7.13 can be prepared by deprotection of an appropriate nucleobase, e.g., 7.12 as shown above. The deprotection is carried out in the presence of an appropriate deprotecting agent, e.g., 7N $NH_3$, in an appropriate solvent, e.g., methanol. Compounds of type 7.14 can be prepared by protection of an appropriate diol, e.g., 7.13 as shown above, The protection reaction is carried out in the presence of an appropriate catalyst, e.g., copper sulfate, and an appropriate acid, e.g., sulphuric acid, in an appropriate solvent, e.g., acetone. Compounds of type 7.16 can be prepared by coupling an appropriate alcohol, e.g., 7.14 as shown above, and an appropriate carboxylic acid, e.g., 7.15 as shown above. Appropriate carboxylic acids are commercially available or prepared by methods known to one skilled in the art. The coupling reaction is carried out in the presence of an appropriate coupling agent, e.g., DCC, and an appropriate activating agent, e.g., DMAP, in an appropriate solvent, e.g., DCM, at an appropriate temperature, e.g., r. Compounds of type 7.17 can be prepared by deprotection of an appropriate acetal, e.g., 7.16 as shown above. The deprotection is carried out in the presence of an appropriate acid, e.g., acetic acid, at an appropriate temperature, e.g., 65° C., for an appropriate period of time, e.g., 1 h. Compounds of type 7.18 can be prepared by deprotection of an appropriate amine, e.g., 7.17 as shown above. The deprotection reaction is carried out in the presence of an appropriate base, e.g., piperidine. As can be appreciated by one skilled in the art, the above reaction provides an example of a generalized approach wherein compounds similar in structure to the specific reactants above (compounds similar to compounds of type 7.1, 7.2, 7.3, 7.4, 7.5, 7.6, 7.7, and 7.8), can be substituted in the reaction to provide substituted 6-aza nucoleoside prodrug derivatives similar to Formula 7.9.

E. METHODS OF USING THE COMPOUNDS

The compounds and pharmaceutical compositions of the invention are useful in treating or controlling disorders associated with a viral infection due to, for example, an Alphavirus (e.g., Chikungunya virus (CHIKV), Ross River virus, Venezuelan equine encephalitis (VEEV), Eastern equine encephalitis (EEEV), and Western equine encephalitis (WEEV)), a Flavivirus (e.g., dengue virus (DENV), West Nile virus (WNV), zika virus (ZIKV), tick-borne encephalitis virus, and yellow fever virus), a Coronavirus (e.g., Middle East Respiratory Syndromes coronavirus (MERS-CoV), Severe Acute Respiratory Syndrome coronavirus (SARS-CoV), and SARS-CoV-2), and a influenza virus (influenza A and influenza B).

Examples of viral infections for which the compounds and compositions can be useful in treating, include, but are not limited to, human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), and coronavirus disease 2019 (COVID-19).

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a viral infection, such as human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), and coronavirus disease 2019 (COVID-19).

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a viral infection, such as human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), and coronavirus disease 2019 (COVID-19).

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with a viral infection due to, for example, an Alphavirus (e.g., Chikungunya virus (CHIKV), Ross River virus, Venezuelan equine encephalitis (VEEV), Eastern equine encephalitis (EEEV), and Western equine encephalitis (WEEV)), a Flavivirus (e.g., dengue virus (DENV), West Nile virus (WNV), zika virus (ZIKV), tick-borne encephalitis virus, and yellow fever virus), a Coronavirus (e.g., Middle East Respiratory Syndromes coronavirus (MERS-CoV), Severe Acute Respiratory Syndrome coronavirus (SARS-CoV), and SARS-CoV-2), and influenza virus (influenza A and influenza B). Thus, provided is a method comprising administering a therapeutically effective amount of a composition comprising a disclosed compound to a subject. In a further aspect, the method can be a method for treating a viral infection.

a. Treating a Viral Infection

In one aspect, disclosed are methods of treating a viral infection in a subject having the viral infection, the method comprising the step of administering to the subject a therapeutically effective amount of at least one disclosed compound, or a pharmaceutically acceptable salt thereof.

In one aspect, disclosed are methods for the treatment of a viral infection in a subject having the viral infection, the method comprising the step of administering to the subject a therapeutically effective amount of at least one compound having a structure represented by a formula:

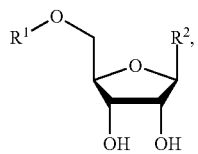

wherein $R^1$ is selected from hydrogen, —C(O)$R^{10}$, —C(O)CH($R^{11}$)NH$_2$, —P(O)(OAr$^1$)NHCH($R^{12}$)CO$_2R^{13}$, and —P(O)(O$R^{14a}$)(O$R^{14b}$); wherein $R^{10}$, when present, is selected from C1-C20 alkyl and C2-C20 alkenyl; wherein $R^{11}$, when present, is a an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

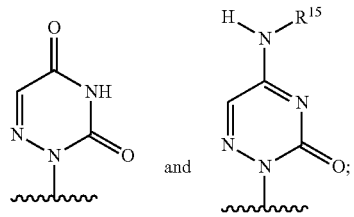

and wherein $R^{15}$, when present, is selected from hydrogen, —C(O)(C1-C20 alkyl), —C(O)(C3-C6 cycloalkyl), and —C(O)(C2-C20 alkenyl), provided that when $R^1$ is hydrogen, then $R^2$ is

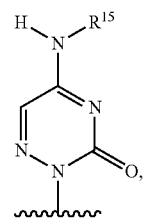

and $R^{15}$ is —C(O)(C1-C20 alkyl), —C(O)(C3-C6 cycloalkyl), or —C(O)(C2-C20 alkenyl), or a pharmaceutically acceptable salt thereof.

Examples of viral infections include, but are not limited to, human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), coronavirus disease 2019 (COVID-19).

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the viral infection.

In a further aspect, the disorder is associated with a viral infection. In a still further aspect, the viral infection is selected from human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), and coronavirus disease 2019 (COVID-19).

In a further aspect, the viral infection is due to an Alphavirus. Examples of Alphaviruses include, but are not limited to, Chikungunya virus (CHIKV), Ross River virus, Venezuelan equine encephalitis (VEEV), Eastern equine encephalitis (EEEV), and Western equine encephalitis (WEEV).

In a further aspect, the viral infection is due to a Flavivirus. Examples of Flaviviruses include, but are not limited to, dengue virus (DENV), West Nile virus (WNV), zika virus (ZIKV), tick-borne encephalitis virus, and yellow fever virus.

In a further aspect, the viral infection is due to a Coronavirus. Examples of Coronaviruses include, but are not limited to, Middle East Respiratory Syndromes coronavirus (MERS-CoV), Severe Acute Respiratory Syndrome coronavirus (SARS-CoV), and SARS-CoV-2.

In a further aspect, the viral infection is due to an influenza virus. Examples of influenza viruses include, but are not limited to, influenza A and influenza B viruses.

In a further aspect, the effective amount is a therapeutically effective amount. In a still further aspect, the effective amount is a prophylactically effective amount.

In a further aspect, the method further comprises the step of administering a therapeutically effective amount of at least one antiviral agent. In a still further aspect, the at least one agent is selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxil fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Inhibiting a Viral Infection in a Mammal

In one aspect, disclosed are methods of inhibiting a viral infection in a mammal, the method comprising the step of administering to the mammal a therapeutically effective amount of at least one disclosed compound, or a pharmaceutically acceptable salt thereof.

In one aspect, disclosed are methods of inhibiting a viral infection in a mammal, the method comprising the step of administering to the mammal a therapeutically effective amount of at least one compound having a structure represented by a formula:

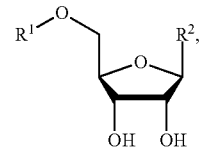

wherein $R^1$ is selected from hydrogen, —C(O)$R^{10}$, —C(O)CH($R^{11}$)NH$_2$, —P(O)(OAr$^1$)NHCH($R^{12}$)CO$_2$$R^{13}$, and —P(O)(OR$^{14a}$)(OR$^{14b}$); wherein $R^{10}$, when present, is selected from C1-C20 alkyl and C2-C20 alkenyl; wherein $R^{11}$, when present, is a an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

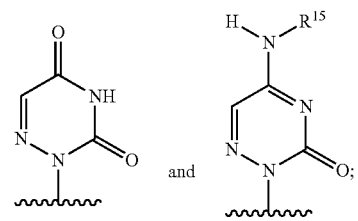

and
wherein $R^{15}$, when present, is selected from hydrogen, —C(O)(C1-C20 alkyl), —C(O)(C3-C6 cycloalkyl), and —C(O)(C2-C20 alkenyl), provided that when $R^1$ is hydrogen, then $R^2$ is

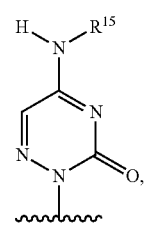

and $R^{15}$ is —C(O)(C1-C20 alkyl), —C(O)(C3-C6 cycloalkyl), or —C(O)(C2-C20 alkenyl), or a pharmaceutically acceptable salt thereof.

In a further aspect, the compound exhibits inhibition of a viral infection. In a still further aspect, the compound exhibits a decrease in a viral infection. In yet a further aspect, the viral infection is due to an Alphavirus (e.g., Chikungunya virus (CHIKV), Ross River virus, Venezuelan equine encephalitis (VEEV), Eastern equine encephalitis (EEEV), and Western equine encephalitis (WEEV)). In an even further aspect, the viral infection is due to a Flavivirus (e.g., dengue virus (DENV), West Nile virus (WNV), zika virus (ZIKV), tick-borne encephalitis virus, and yellow fever virus). In a still further aspect, the viral infection is due to a Coronavirus (e.g., Middle East Respiratory Syndromes coronavirus (MERS-CoV), Severe Acute Respiratory Syndrome coronavirus (SARS-CoV), and SARS-CoV-2). In yet a further aspect, the viral infection is influenza.

In a further aspect, the compound exhibits inhibition of viral activity with an $EC_{50}$ of less than about 30 μM. In a still further aspect, the compound exhibits inhibition of viral activity with an $EC_{50}$ of less than about 25 μM. In yet a further aspect, the compound exhibits inhibition of CHIKV activity with an $EC_{50}$ of less than about 20 μM. In an even further aspect, the compound exhibits inhibition of viral activity with an $EC_{50}$ of less than about 15 μM. In a still further aspect, the compound exhibits inhibition of viral activity with an $EC_{50}$ of less than about 10 μM. In yet a further aspect, the compound exhibits inhibition of viral activity with an $EC_{50}$ of less than about 5 μM. In an even further aspect, the compound exhibits inhibition of viral activity with an $EC_{50}$ of less than about 1 μM. In a still further aspect, the compound exhibits inhibition of viral activity with an $EC_{50}$ of less than about 0.5 μM.

In a further aspect, the subject is a mammal. In a still further aspect, the subject is a human.

In a further aspect, the subject has been diagnosed with a need for treatment of the disorder prior to the administering step. In a still further aspect, the method further comprises the step of identifying a subject in need of treatment of the disorder.

3. Methods of Inhibiting a Viral Infection in at Least One Cell

In one aspect, disclosed are methods for inhibiting a viral infection in at least one cell, the method comprising the step of contacting the at least one cell with an effective amount of at least one disclosed compound, or a pharmaceutically acceptable salt thereof.

In one aspect, disclosed are methods for inhibiting a viral infection in at least one cell, the method comprising the step of contacting the at least one cell with an effective amount of at least one compound having a structure represented by a formula:

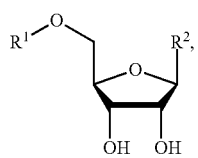

wherein $R^1$ is selected from hydrogen, —C(O)$R^{10}$, —C(O)CH($R^{11}$)NH$_2$, —P(O)(OAr$^1$)NHCH($R^{12}$)CO$_2$$R^{13}$, and —P(O)(OR$^{14a}$)(OR$^{14b}$); wherein $R^{10}$, when present, is selected from C1-C20 alkyl and C2-C20 alkenyl; wherein $R^{11}$, when present, is a an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

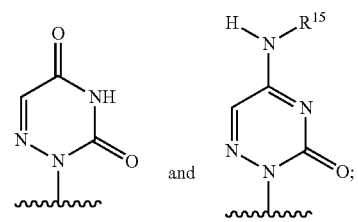

wherein $R^{15}$, when present, is selected from hydrogen, —C(O)(C1-C20 alkyl), —C(O)(C3-C6 cycloalkyl), and —C(O)(C2-C20 alkenyl), provided that when $R^1$ is hydrogen, then $R^2$ is

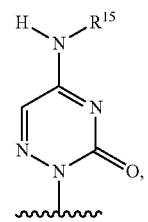

and $R^{15}$ is —C(O)(C1-C20 alkyl), —C(O)(C3-C6 cycloalkyl), or —C(O)(C2-C20 alkenyl), or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

4. Use of Compounds

In one aspect, the invention relates to the use of a disclosed compound or a product of a disclosed method. In a further aspect, a use relates to the manufacture of a medicament for the treatment of a viral infection in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a viral infection in a subject. Also disclosed is the use of a compound for antagonism of a viral infection. In one aspect, the use is characterized in that the subject is a human. In one aspect, the use is characterized in that the disorder is a viral infection.

In a further aspect, the use relates to the manufacture of a medicament for the treatment of a viral infection in a subject.

In a further aspect, the use relates to antagonism of a viral infection in a subject. In a further aspect, the use relates to modulating viral activity in a subject. In a still further aspect, the use relates to modulating viral activity in a cell. In yet a further aspect, the subject is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a viral infection in a mammal. In a further aspect, the viral infection is selected from human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), and coronavirus disease 2019 (COVID-19).

5. Manufacture of a Medicament

In one aspect, the invention relates to a method for the manufacture of a medicament for treating a viral infection in a subject having the viral infection, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of a viral infection. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, disclosed are kits comprising at least one disclosed compound and one or more of: (a) at least one antiviral agent; (b) a instructions for administering the at least one compound in connection with treating a viral infection; (c) instructions for administering the at least one compound in connection with reducing the risk of viral infection; and (d) instructions for treating a viral infection.

In a further aspect, the compound has a structure represented by a formula:

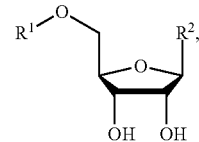

wherein $R^1$ is selected from hydrogen, —C(O)$R^{10}$, —C(O)CH($R^{11}$)NH$_2$, —P(O)(OAr$^1$)NHCH($R^{12}$)CO$_2R^{13}$, and —P(O)(OR$^{14a}$)(OR$^{14b}$); wherein $R^{10}$, when present, is selected from C1-C20 alkyl and C2-C20 alkenyl; wherein $R^1$, when present, is a an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

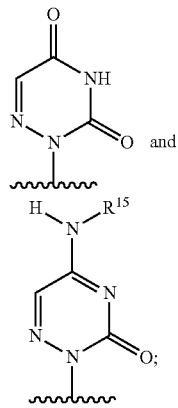

and
wherein $R^{15}$, when present, is selected from hydrogen, —C(O)(C1-C20 alkyl), —C(O)(C3-C6 cycloalkyl), and —C(O)(C2-C20 alkenyl), provided that when $R^1$ is hydrogen, then $R^2$ is

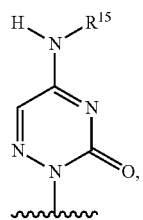

and $R^{15}$ is —C(O)(C1-C20 alkyl), —C(O)(C3-C6 cycloalkyl), or —C(O)(C2-C20 alkenyl), or a pharmaceutically acceptable salt thereof.

In a further aspect, the compound has a structure represented by a formula:

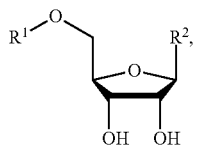

wherein $R^1$ is selected from hydrogen, —C(O)$R^{10}$, —C(O)CH($R^{11}$)NH$_2$, —P(O)(OAr$^1$)NHCH($R^{12}$)CO$_2R^{13}$, and —P(O)(OR$^{14a}$)OR$^{14b}$); wherein $R^{10}$, when present, is selected from C1-C20 alkyl and C2-C20 alkenyl; wherein $R^{11}$, when present, is an amino acid derivative side chain; wherein $R^{12}$, when present, is selected from C1-C6 alkyl and C3-C6 cycloalkyl; wherein $R^{13}$, when present, is selected from C1-C8 alkyl, C3-C8 cycloalkyl, Ar$^2$, and —CH$_2$Ar$^2$; wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{14a}$ and $R^{14b}$, when present, is independently selected from hydrogen and C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

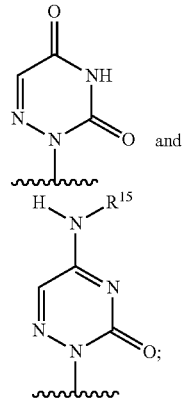

and
wherein $R^{15}$, when present, is selected from hydrogen, —C(O)(C1-C20 alkyl), —C(O)(C3-C6 cycloalkyl), and —C(O)(C2-C20 alkenyl), provided that when $R^2$ is

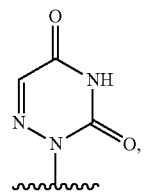 [SMILES: *n1ncc(=O)[nH]c1=O]

then $R^1$ is —C(O)CH($R^{11}$)NH$_2$, —P(O)(OAr$^1$)NHCH($R^{12}$)CO$_2R^{13}$, or —P(O)(OR$^{14a}$)(OR$^{14b}$), and provided that when $R^1$ is hydrogen, then $R^{15}$ is —C(O)(C1-C20 alkyl), —C(O)(C3-C6 cycloalkyl), or —C(O)(C2-C20 alkenyl), or a pharmaceutically acceptable salt thereof.

In a further aspect, the compound has a structure:

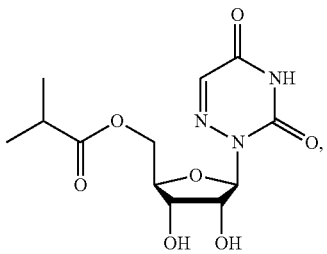

or a pharmaceutically acceptable salt thereof.

In a further aspect, the viral infection is selected from human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, yellow fever virus, tick-borne encephalitis virus, Chikungunya virus (CHIKV), Venezuelan equine encephalitis (VEEV), Eastern equine encephalitis (EEEV), Western equine encephalitis (WEEV), dengue (DENV), influenza, West Nile virus (WNV), zika (ZIKV), Middle East Respiratory Syndromes (MERS), Severe Acute Respiratory Syndrome (SARS), and coronavirus disease 2019 (COVID-19). In a still further aspect, the viral infection is selected from CHIKV, DENV, WNV, ZIKA, VEEV, SARS, and COVID-19.

In a still further aspect, the antiviral agent is selected from selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscamet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, MK-4482 (EIDD-2801), penciclovir, raltegravir, ribavirin, rimantadine hydrochloride, rilpivirine (TMC-278), remdesivir, saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the immunity booster is selected from vitamin D, elderberry, Echinacea, a probiotic, vitamin C, vitamin B, green tea, turmeric, zinc, ashwagandha, a prebiotic, and a synbiotic.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals a. General Experimental

The reactions were performed under a dry argon atmosphere and reaction temperatures were measured externally. Anhydrous solvents over molecular sieves were purchased from Aldrich and used as such in reactions. Microwave (MW) reactions were performed in CEM Discover Labmate System with Intelligent Technology for Focused™ Microwave Synthesizer (Explorer 48) or Biotage Initiator+ equipped with Robot Eight microwave system. The reactions were monitored by thin-layer chromatography (TLC) on pre-coated silica gel ($60F_{254}$) aluminium plates (0.25 mm) from E. Merck and visualized using UV light (254 nm). Purification of compounds was performed on an Isco Teledyne Combiflash Rf200. Universal RediSep solid sample loading pre-packed cartridges (5.0 g silica) were used to absorb crude product and purified on silica RediSep Rf Gold Silica (20-40 μm spherical silica) columns using appropriate solvent gradients. Pure samples were dried overnight under high vacuum before analyses. The high resolution electrospray ionization mass spectral data (HR-ESIMS) were obtained on an Agilent LC-MSTOF. $^1$H, $^{13}$C, $^{19}$F, and $^{31}$P NMR spectra were recorded at 400, 101, 376 and 162 MHz respectively on an Agilent/Varian MR-400 spectrometer. The chemical shifts (δ) are in ppm downfield from standard tetramethylsilane (TMS). HPLC of final compounds were run on an Agilent 1100 LC equipped with a diode array UV detector and were monitored at 254 nm by using one of the following methods Method A: Sunfire C18 column (5 μm, 4.6×150 mm) using $H_2O$—$CH_3CN$ (both containing 0.1% formic acid) 5-95% in 20 min with flow rate 1.0 mL/min.; Method B: Phenomenex Kinetex 2.6p Phenyl-hexyl 100 Å 50×4.6 mm column using Solvent A: 95:5 $H_2O$:MeCN with 1% $HCO_2H$, Solvent B: MeCN with 0.1% $HCO_2H$, flow rate 2.0 mL/min; 4 min linear gradient from 5-95% B.

b. Synthesis of (5-nitrofuran-2-yl)methyl ((((2R,3S,4R,5R)-5-(3,5-dioxo-4,5-dihydro-1,2,4-triazin-2(3H)-yl)-3,4-dihydroxytetra-hydrofuran-2-yl)methoxy)(phenoxy)phosphoryl)-L-alaninate (1)

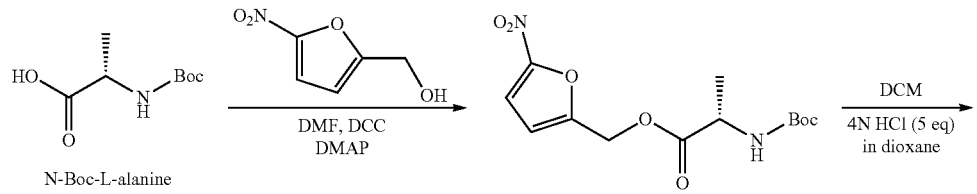

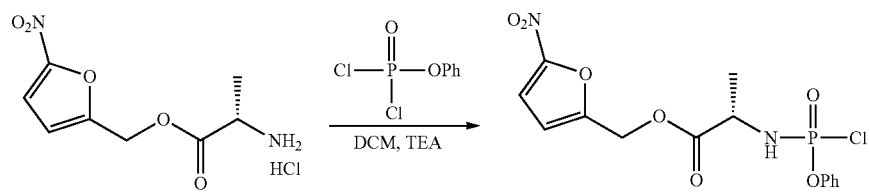

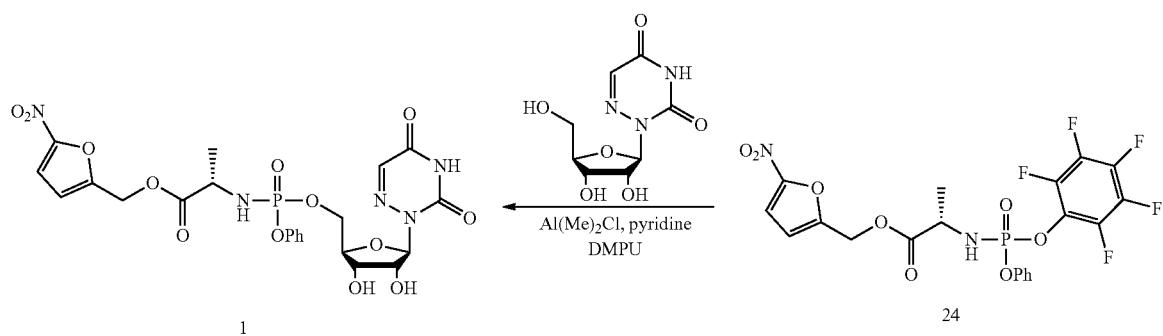

i. Preparation of (5-nitrofuran-2-yl)methyl (tert-butoxy-carbonyl)-L-alaninate (21)

To a 500 mL round bottom flask was added 5-nitrofurfuryl alcohol (10.0 g, 69.9 mmol, 1.0 eq), N-Boc-L-alanine (14.5 g, 76.9 mmol, 1.1 eq), 4-dimethylaminopyridine (0.08 g, 0.69 mmol, 0.01 eq), 130 mL of anhydrous N,N-dimethylformamide, followed by dicyclohexylcarbodiimide (21.6 g, 104.8 mmol, 1.5 eq). The reaction mixture was stirred for 2 days at room temperature. The reaction mixture was diluted with 500 mL of ethyl acetate and then filtered by vacuum filtration to remove byproduct dicyclohexyl urea. The filtrate was washed with water (3×200 mL), saturated sodium bicarbonate (2×200 mL), saturated ammonium chloride (100 mL), followed by brine (100 mL). The combined organic layer was separated, dried over sodium sulfate, filtered, and then the filtrate was evaporated under reduced pressure to afford 34 g of a dark red-brown oil. The crude material was purified in two portions (2×220 g RediSep Rf Gold Silica gel column, 100-90% dichloromethane in methanol, gradient elution) to provide 17.79 g (81%) of 21 as an orange oil. $^1$HNMR (DMSO-d$_6$) δ 7.71 (d, J=3.7 Hz, 1H), 7.40 (d, J=7.2 Hz, 1H), 6.94 (d, J=3.8 Hz, 1H), 5.33-5.09 (m, 2H), 4.06 (dq, J=11.5, 7.2 Hz, 2H), 1.37 (s, 9H), 1.26 (d, J=7.4 Hz, 3H). LCMS m/z 529 (M+H)$^+$.

i. Preparation of (5-nitrofuran-2-yl)methyl L-alaninate hydro-chloride (22)

To a solution of 21 (5.3 g, 16.86 mmol, 1.0 eq) in 50 mL of anhydrous dichloromethane was added 4N hydrochloric acid (21.1 mL, 84.3 mmol, 5.0 eq) in 1,4-dioxane. The reaction mixture was stirred at 20° C. for 18 h. A precipitate formed, which was filtered by vacuum filtration, rinsed with anhydrous diethyl ether and then dried under reduced pressure to afford 3.89 g of 22 (92%) as an off-white solid. $^1$HNMR (DMSO-$d_6$) δ 8.67 (s, 3H), 7.73 (d, J=3.8 Hz, 1H), 7.15-6.93 (m, 1H), 5.37 (s, 2H), 4.18 (q, J=7.2 Hz, 3H), 1.45 (d, J=7.2 Hz, 3H).

ii. Preparation of (5-nitrofuran-2-yl)methyl ((per-fluoro-phenoxy)-(phenoxy)-phosphoryl)-L-alaninate (24)

To a mixture of 22 (10.0 g, 39.9 mmol, 1.0 eq) in 140 mL of anhydrous dichloromethane was added phenyl phosphorodichloridate (6.54 mL, 43.9 mmol, 1.1 eq). The mixture was cooled to −75° C. and then a solution of triethylamine (11.7 mL, 83.8 mmol, 2.1 eq) in 120 mL of anhydrous dichloromethane was added over 70 min at −70° C. Upon completion of addition, the reaction mixture was stirred at −75° C. for 2 h and then for 18 h as it warmed to 20° C. The reaction mixture was evaporated under reduced pressure to afford a semi-solid, which was triturated in 200 mL of anhydrous t-butyl methylether for 1 h. The mixture was filtered by vacuum filtration to remove triethylamine hydrochloride, which was rinsed with anhydrous t-butyl methylether (2×50 mL). The filtrate was evaporated under vacuum to provide 17.88 g of 23 as an orange oil, which was used further as such. To a cold (−5° C.) solution of 23 (15.51 g, 39.9 mmol, 1.0 eq) in 120 mL of anhydrous dichloromethane was added a solution of pentafluorophenol (8.1 g, 43.9 mmol, 1.1 eq) and triethylamine (6.12 mL, 43.9 mmol, 1.1 eq) in 120 mL of anhydrous dichloromethane over 45 min at −5° C. The reaction mixture was stirred at 0° C. for 2 h and then for 18 h as it warmed to 20° C. The reaction mixture was evaporated under reduced pressure to afford a semi-solid, which was triturated in ethyl acetate (250 mL) and then stirred for 30 min. The mixture was filtered by vacuum filtration to remove triethylamine hydrochloride, which was rinsed with 100 mL of ethyl acetate. The filtrate was washed with water (2×100 mL), 10% aqueous sodium carbonate (2×100 mL), followed by brine (25 mL). The organic layer was separated, dried over sodium sulfate, filtered, and then the filtrate was evaporated under vacuum to give 27.8 g of a crude semi-solid. Purification by flash chromatography (220 g silica column, 100-40% hexane in ethyl acetate, gradient elution) provided 8.25 g (38%) of compound 24 as a white solid (mixture of diastereomers 55:45). $^1$HNMR (DMSO-$d_6$) δ 7.67 (t, J=3.7 Hz, 1H), 7.46-7.36 (m, 2H), 7.29-7.16 (m, 3H), 7.02 (ddd, J=14.0, 9.9, 6.2 Hz, 1H), 6.92 (d, J=3.8 Hz, 1H), 5.36-5.09 (m, 2H), 4.23-3.85 (m, 1H), 1.34 (dd, J=7.2, 1.3 Hz, 3H). $^{19}$FNMR (DMSO-$d_6$) $δ_F$ −153.83 (ddt, J=19.1, 15.9, 3.9 Hz, 2F), −160.21 (td, J=23.1, 3.3 Hz, 1F), −163.07 (dtd, J=27.8, 23.7, 4.1 Hz, 2F). $^{31}$PNMR (DMSO-$d_6$) $δ_p$ 0.13, 0.03. LCMS: m/z 537 (M+H)$^+$.

iii. Preparation of Compound 1

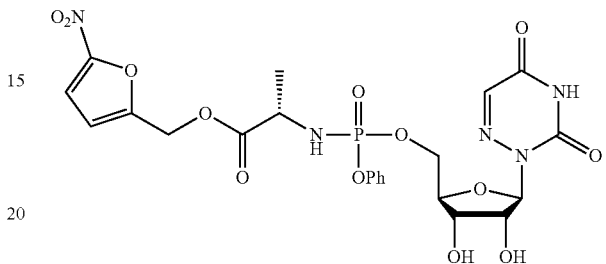

To an oven-dried 50 mL round bottom flask was added 6-azauridine (400 mg, 1.63 mmol, 1.0 eq) and co-evaporation twice with anhydrous pyridine (2×3.0 mL) under reduced pressure at 40° C. Further, vacuum dried 6-azauridine was dissolved in anhydrous pyridine (4.89 mL) followed by addition of 1,3-dimethyl-3,4,5,6-tetrahydro-2-(1H)-pyrimidone (0.933 mL, 7.71 mmol., 5.0 eq). The mixture was stirred for 15 min and then 24 (1.05 g, 1.96 mmol, 1.2 eq) was added. The mixture was further stirred for 5 min and then cooled to 0° C. An 1M solution of dimethylaluminum chloride (0.816 mL, 0.82 mmol, 0.50 eq) in hexanes was slowly added over 5 seconds and them the reaction mixture was stirred for 5 days as it warmed to 20° C. The reaction mixture was evaporated under vacuum to afford crude 1 as a brown oil, which was purified by flash chromatography (40 g silica column, 100-95% dichloromethane in methanol, gradient elution) to provide 118 mg (12%) of pure 1 as a yellow foamy solid (mixture of diastereomers, 53:47). $^1$HNMR (DMSO-$d_6$) δ 12.24 (s, 1H), 7.62 (dd, J=10.5, 3.7 Hz, 1H), 7.48 (dd, J=2.9, 0.6 Hz, 1H), 7.37-7.26 (m, 2H), 7.19-7.05 (m, 3H), 6.88 (ddt, J=6.1, 3.7, 0.6 Hz, 1H), 6.07 (dd, J=13.1, 9.9 Hz, 1H), 5.94-5.84 (m, 1H), 5.40 (dd, J=5.9, 5.1 Hz, 1H), 5.25-5.11 (m, 3H), 4.30-3.64 (m, 7H), 1.21 (ddd, J=13.1, 7.1, 1.0 Hz, 3H). $^{31}$PNMR (DMSO-$d_6$) δ 3.41, 3.32. LCMS m/z 598 (M+H)$^+$. HR-ESIMS m/z calcd for $C_{22}H_{24}N_5O_{13}P·H$, 598.1181, found 598.1170. HPLC purity by Method B: 97.7% at 254 nm.

c. Synthesis of Compound Nos. 2-7

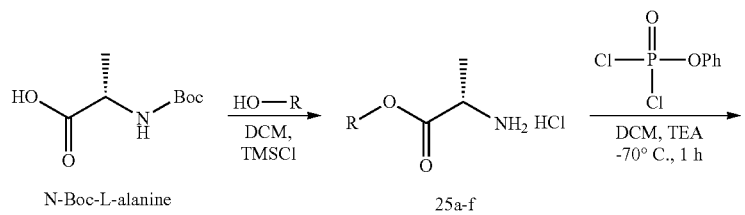

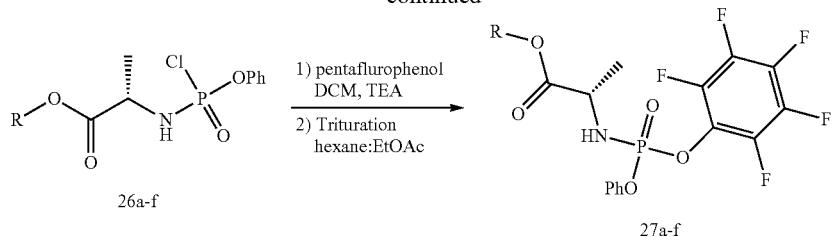

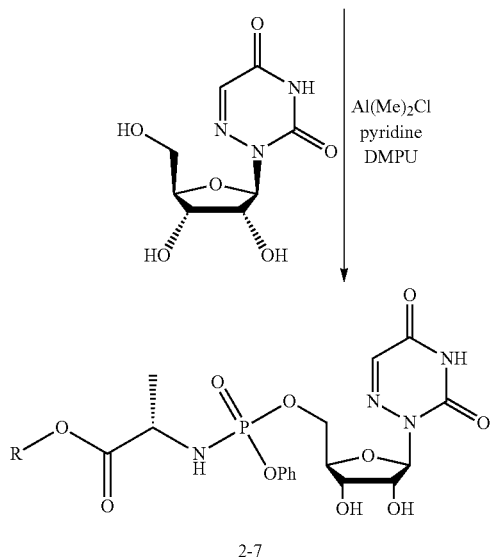

i. Synthesis of Benzyl (((((2R,3S,4R,5R)-5-(3,5-dioxo-4,5-dihydro-1,2,4-triazin-2(3H)-yl)-3,4-dihydroxytetrahydrofuran-2-yl)methoxy)-(phenoxy)phosphoryl)-L-alaninate (2)

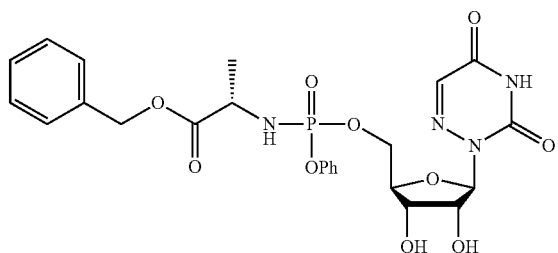

(1) Preparation of Benzyl ((S)-(perfluorophenoxy)(phenoxy)-phosphoryl)-L-alaninate (27a)

To a solution of commercial benzyl-L-alaninate hydrochloride 25a (10.0 g, 46.37 mmol, 1.0 eq) in 140 mL of anhydrous dichloromethane was added phenyl phosphorodichloridate (7.60 mL, 51.00 mmol, 1.1 eq). The mixture was cooled to −75° C. and then a solution of triethylamine (13.57 mL, 97.37 mmol, 2.1 eq) in 50 mL of anhydrous dichloromethane was added over 70 min at −70° C. Upon completion of addition, the reaction mixture was stirred at −75° C. for 2 h and then for 18 h as it warmed to 20° C. The reaction mixture was evaporated under reduced pressure to afford a semi-solid, which was triturated in 200 mL of anhydrous t-butyl methylether for 1 h. The mixture was filtered by vacuum filtration to remove triethylamine hydrochloride, which was rinsed with anhydrous t-butyl methylether (2×50 mL). The filtrate was evaporated under vacuum to provide 18.02 g of 26a intermediate as a yellow-green oil. This material was used as such in the next step to prepare intermediate 27a. To a cold (−5° C.) solution of 26a (16.40 g, 46.37 mmoles, 1.0 eq) in 120 mL of anhydrous dichloromethane was added a solution of pentafluorophenol (9.31 g, 51.00 mmoles, 1.1 eq) and triethylamine (7.11 mL, 51.00 mmoles, 1.1 eq) in 50 mL of anhydrous dichloromethane over 45 min at −5° C. The reaction mixture was stirred at 0° C. for 2 hrs and then for 18 hrs as it warmed to 20° C. The reaction mixture was evaporated under reduced pressure to afford a semi-solid, which was triturated in ethyl acetate (250 mL) and then stirred for 30 min. The mixture was filtered by vacuum filtration to remove triethylamine hydrochloride, which was rinsed with 100 mL of ethyl acetate. The filtrate was washed with water (2×100 mL), 10% sodium carbonate (2×100 mL), followed by brine (25 mL). The organic layer was separated, dried over sodium sulfate, filtered, and then the filtrate was evaporated under vacuum to give 28.91 g of a crude semi-solid. The crude material was purified in two portions by flash chromatography (120 g silica column, 100 to 70% hexane in ethyl acetate, gradient elution) to provide a combined mass which was triturated from 95% hexane in ethyl acetate (100 mL) to give 11.24 g (48%) of 27a as a single diastereomer. $^1$HNMR (DMSO-d$_6$) δ 7.44-7.30 (m, 7H), 7.29-7.19 (m, 3H), 6.97 (dd, J=14.1, 9.9 Hz, 1H), 5.12 (s, 2H), 4.17-3.94 (m, 1H), 1.33 (dd, J=7.1, 1.3 Hz, 3H). $^{19}$FNMR (DMSO-d$_6$) δ$_F$ −153.30−−154.12 (m, 2F), −160.26 (td, J=23.6, 3.5 Hz, 1F), −163.14 (td, J=23.6, 4.1 Hz, 2F). $^{31}$PNMR (DMSO-d$_6$) δ$_P$ 0.26. LCMS: m/z 502 (M+H)$^+$.

(2) Preparation of Compound 2

The final target 2 was prepared from commercial 6-azauridine (250 mg, 1.02 mmoles, 1.0 eq), 27a (613 mg, 1.22 mmol, 1.2 eq), 1,3-dimethyl-3,4,5,6-tetrahydro2(1H)-pyrimidone (0.62 mL, 5.10 mmol, 5.0 eq), and 1M dimethylaluminum chloride in hexanes (0.51 mL, 0.51 mmol, 0.50 eq) in 3.0 mL of anhydrous pyridine according to the procedure described for the preparation of 1 to afford an oil, which was purified by flash chromatography (40 g silica column, 100-90% dichloromethane in methanol, gradient elution) to provide 50 mg (9%) of compound 2 as a white foamy solid (mixture of diasteromers 81:19). $^1$HNMR (DMSO-d$_6$) δ 12.20 (s, 1H), 7.51 (d, J=0.6 Hz, 1H), 7.41-7.30 (m, 7H), 7.21-7.11 (m, 3H), 6.08-5.99 (m, 1H), 5.96-5.93 (m, 1H), 5.43 (d, J=5.1 Hz, 1H), 5.24 (d, J=6.1 Hz, 1H), 5.15-5.04 (m, 2H), 4.34-3.72 (m, 6H), 1.26 (dd, J=7.1, 1.0 Hz, 3H); $^{31}$PNMR (DMSO-d$_6$) δ$_P$ 3.49, 3.47. LCMS m/z 563 (M+H)$^+$. HR-ESIMS m/z calcd for C$_{24}$H$_{27}$N$_4$O$_{10}$P·H, 563.1538, found 563.1539. HPLC purity 91.6% at 254 nm.

ii. Synthesis of 2-ethylbutyl ((((2R,3S,4R,5R)-5-(3,5-dioxo-4,5-dihydro-1,2,4-triazin-2(3H)-yl)-3,4-dihydroxytetrahydrofuran-2-yl)methoxy)(phenoxy)phosphoryl)-L-alaninate (3)

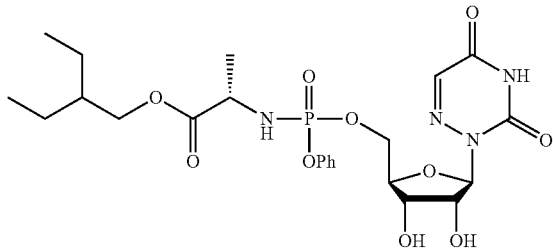

(1) Preparation of 2-ethylbutyl L-alaninate hydrochloride (25b)

To a solution of N-Boc-L-alanine (10.0 g, 52.85 mmol, 1.0 eq.) in 2-ethyl-1-butanol (100 mL, 15.5 eq.) was added trimethylsilyl chloride (33.5 mL, 264 mmol, 5.0 eq). The reaction mixture was stirred at 20° C. for 18 h. The reaction mixture was evaporated under reduced pressure at 60° C. to afford an oil, which was triturated in 100 mL of anhydrous diethyl ether. The mixture was filtered by vacuum filtration to collect a solid which was rinsed with anhydrous diethyl ether (2×40 mL) and then dried under reduced pressure at 50° C. to provide 9.40 g (85%) of 25b as a white solid. $^1$HNMR (DMSO-d$_6$) δ 8.59 (s, 3H), 4.18-4.01 (m, 3H), 1.53 (hept, J=6.1 Hz, 1H), 1.44 (d, J=7.2 Hz, 3H), 1.41-1.29 (m, 4H), 0.88 (t, J=7.4 Hz, 6H).

(2) Preparation of 2-ethylbutyl ((S)-(perfluorophenoxy)-(phenoxy)phosphoryl)-L-alaninate (27b)

Intermediate 26b was prepared from 25b (10.0 g, 46.37 mmol, 1.0 eq) and phenyl phosphorodichloridate (7.82 mL, 52.45 mmol, 1.1 eq) in 140 mL of anhydrous dichloromethane with triethylamine (13.96 mL, 100 mmol, 2.1 eq) as a base according to the procedure described for the preparation of 26a to afford 18.02 g as a colorless oil. Further, compound 27b was prepared from intermediate 26b (16.6 g, 47.68 mmol, 1.0 eq) and pentafuorophenol (8.44 g, 45.86 mmol, 0.96 eq) in 120 mL of anhydrous dichloromethane with triethylamine (6.39 mL, 45.86 mmol, 0.96 eq) as base according to the procedure described for the preparation of 27a to afford 4.9 g (21%) as white needles and as a single diastereomer. $^1$HNMR (DMSO-d$_6$) δ 7.43 (dd, J=8.5, 7.4 Hz, 2H), 7.32-7.17 (m, 3H), 6.91 (dd, J=14.1, 9.9 Hz, 1H), 3.99 (dd, J=14.2, 6.4 Hz, 3H), 1.45 (h, J=6.1 Hz, 1H), 1.37-1.23 (m, 7H), 0.83 (t, J=7.4 Hz, 6H). $^{19}$FNMR (DMSO-d$_6$) δ$_F$ −153.68 to −153.78 (m, 2F), −160.39 (td, J=23.6, 3.3 Hz, 1F), −163.21 (td, J=23.6, 4.1 Hz, 2F). $^{31}$PNMR (DMSO-d$_6$) δ$_P$ 0.27. LCMS: m/z 496 (M+H)$^+$.

(3) Preparation of Compound 3

The final target 3 was prepared from commercial 6-azauridine (100 mg, 0.408 mmol, 1.0 eq), 27b (242 mg, 0.489 mmol, 1.2 eq), 1,3-dimethyl-3,4,5,6-tetrahydro-2-(1H)-pyrimidone (0.247 mL, 2.04 mmol, 5.0 eq), and 1M solution of dimethylaluminum chloride in hexanes (0.204 mL, 0.204 mmol, 0.50 eq) in 3.0 mL of anhydrous pyridine according to the procedure described for the preparation of 1 to afford an oil, which was purified by flash chromatography (40 g silica column, 100-90% dichloromethane in methanol, gradient elution) to provide 26 mg (11%) of compound 3 as a colorless solid (mixture of diastereomers 94:6). $^1$HNMR (DMSO-d$_6$) δ 12.27 (d, J=9.5 Hz, 1H), 7.51 (s, 1H), 7.43-7.31 (m, 2H), 7.27-7.11 (m, 3H), 6.02-5.88 (m, 2H), 5.43 (d, J=5.0 Hz, 1H), 5.24 (d, J=6.1 Hz, 1H), 4.25-4.13 (m, 2H), 4.10-3.89 (m, 5H), 3.88-3.78 (m, 1H), 1.47 (hept, J=6.2 Hz, 1H), 1.37-1.22 (m, 7H), 0.85 (t, J=7.5 Hz, 6H). $^{31}$PNMR (DMSO-d$_6$) δ$_P$ 3.51, 3.47. LCMS m/z 557 (M+H)$^+$. HR-ESIMS m/z calcd for C$_{23}$H$_{33}$N$_4$O$_{10}$P·H, 557.20071, found 557.20075. HPLC purity by Method B: 97.4% at 254 nm.

iii. Synthesis of 2-isobutyl ((((2R,3S,4R,5R)-5-(3,5-dioxo-4,5-dihydro-1,2,4-triazin-2(3H)-yl)-3,4-dihydroxytetrahydrofuran-2-yl)methoxy)(phenoxy)phosphoryl)-L-alaninate (4)

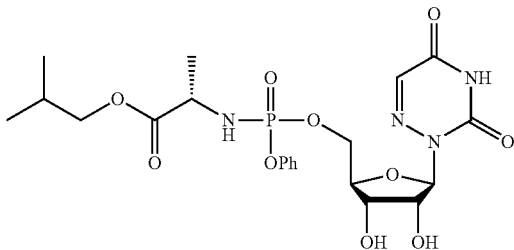

(1) Preparation of Isobutyl L-alaninate hydrochloride (25c)

Intermediate 25c was prepared from N-Boc-L-alanine (3.0 g, 15.86 mmoles, 1.0 eq.) and trimethylsilyl chloride (10.0 mL, 79.28 mmoles, 5.0 eq) in 2-methyl-1-propanol (100 mL, 69 mmol) according to the procedure described for the preparation of 25b to afford 2.66 g (92%) of a white solid. $^1$HNMR (DMSO-d6) δ 8.61 (s, 3H), 4.09 (q, J=7.2 Hz, 1H), 4.04-3.89 (m, 2H), 1.94 (dh, J=13.4, 6.6 Hz, 1H), 1.45 (d, J=7.2 Hz, 3H), 0.93 (dd, J=6.7, 0.7 Hz, 6H).

(2) Preparation of Isobutylbutyl ((S)-(perfluorophenoxy)-(phenoxy)phosphoryl)-L-alaninate (27c)

Intermediate 26c was prepared from 25c (2.0 g, 11.01 mmol, 1.0 eq) and phenyl phosphorodichloridate (1.81 mL, 12.11 mmol, 1.1 eq) in 20 mL of anhydrous dichloromethane with triethylamine (3.22 mL, 23.12 mmol, 2.1 eq) as base according to the procedure described for the preparation of 26a to afford 3.83 g of 26c as a colorless oil. Further, 27c, was prepared from 26b (3.83 g, 11.98 mmol, 1.0 eq) and pentafuorophenol (2.43 g, 13.18 mmol, 1.1 eq) in 20 mL of anhydrous dichloromethane with triethylamine (1.84 mL, 13.18 mmol, 1.1 eq) as base according to the procedure described for the preparation of 27a to afford 1.43 g (26%) of pure 27c as a single diastereomer. $^1$HNMR (DMSO-d$_6$) δ 7.48-7.38 (m, 2H), 7.30-7.19 (m, 3H), 6.90 (dd, J=14.1, 9.9 Hz, 1H), 4.11-3.94 (m, 1H), 3.84 (dd, J=6.6, 0.6 Hz, 2H), 1.93-1.79 (m, J=6.7 Hz, 1H), 1.32 (dd, J=7.1, 1.2 Hz, 3H), 0.88 (d, J=6.7 Hz, 6H). $^{31}$PNMR (DMSO-d$_6$) δ$_P$ 0.28. LCMS: m/z 468 (M+H)$^+$.

(3) Preparation of Compound 4

The final target 4 was prepared from commercial 6-azauridine (200 mg, 0.816 mmol, 1.0 eq), 27c (457 mg, 0.979 mmol, 1.2 eq), 1,3-dimethyl-3,4,5,6-tetrahydro-2-(1H)-pyrimidone (0.49 mL, 4.08 mmol, 5.0 eq), and 1M dimethylaluminum chloride solution in hexanes (0.49 mL, 0.494 mmol, 0.60 eq) and 1.50 mL of anhydrous pyridine according to the procedure described for the preparation of 1 to afford a residue, which was purified by flash chromatography (40 g silica column, 100-90% dichloromethane in methanol, gradient elution) to provide 47 mg (11%) as a white solid and as a single diastereomer. $^1$HNMR (DMSO-d$_6$) δ 12.24 (d, J=5.0 Hz, 1H), 7.52 (d, J=0.5 Hz, 1H), 7.40-7.33 (m, 2H), 7.24-7.14 (m, 3H), 6.01-5.91 (m, 2H), 5.42 (d, J=5.0 Hz, 1H), 5.23 (d, J=6.2 Hz, 1H), 4.27-4.12 (m, 2H), 4.10-3.90 (m, 3H), 3.89-3.75 (m, 3H), 1.86 (hept, J=6.7 Hz, 1H), 1.25 (dd, J=7.1, 1.0 Hz, 3H), 0.88 (d, J=6.7 Hz, 6H). $^{31}$PNMR (DMSO-d$_6$) δ$_P$: 3.49; LCMS m/z 551 (M+H)$^+$. HRMS m/z calcd. for C$_{21}$H$_{29}$N$_4$O$_{10}$P·H, 529.1694, found, 529.1690. HPLC purity by Method B: 91% at 254 nm.

iv. Synthesis of isopropyl (((((2R,3S,4R,5R)-5-(3,5-dioxo-4,5-dihydro-1,2,4-triazin-2(3H)-yl)-3,4-dihydroxytetrahydrofuran-2-yl)methoxy)(phenoxy)phosphoryl)-L-alaninate (5)

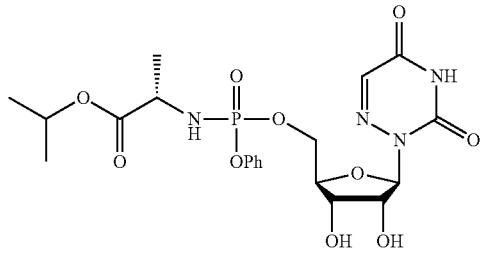

(1) Preparation of Isopropyl ((S)-(perfluorophenoxy)-(phenoxy)phosphoryl)-L-alaninate (27d)

Intermediate 26d was prepared from commercial isopropyl-L-alaninate hydrochloride 25d (2.0 g, 11.93 mmol, 1.0 eq.) and phenyl phosphorodichloridate (1.96 mL, 13.12 mmol, 1.1 eq.) in 20 mL of anhydrous dichloromethane with triethylamine (3.49 mL, 25.05 mmol, 2.1 eq.) as base according to the procedure described for the preparation of 26a to afford 3.65 g of a colorless oil. Further, compound 27d was prepared from intermediate 26d (3.65 g, 11.93 mmol, 1.0 eq) and pentafuorophenol (2.41 g, 13.12 mmol, 1.1 eq) in 20 mL of anhydrous dichloromethane with triethylamine (1.83 mL, 13.12 mmol, 1.1 eq) as base according to the procedure described for the preparation of 27a to afford 2.22 g (41%) (27d) of a white solid and as a single diastereomer. $^1$HNMR (DMSO-d$_6$) δ 7.48-7.39 (m, 2H), 7.32-7.20 (m, 3H), 6.99-6.74 (m, 1H), 4.89 (pd, J=6.3, 5.5 Hz, 1H), 4.02-3.82 (M, 1 h), 1.29 (ddd, J=7.1, 4.6, 1.2 Hz, 3H), 1.17 (dd, J=6.3, 1.1 Hz, 6H). $^{19}$FNMR (DMSO-d$_6$) δ$_F$ −153.76 (t, J=21.2 Hz, 2F), −159.94 to −160.90 (m, 1F), −162.68 to −163.68 (m, 2F). $^{31}$PNMR (DMSO-d$_6$) δ$_P$ 0.31. LCMS: m/z 454 (M+H)$^+$.

(2) Preparation of Compound 5

The final target 5 was prepared from commercial 6-azauridine (250 mg, 1.02 mmoles, 1.0 eq.), 27d (555 mg, 1.22 mmol, 1.2 eq.), 1,3-dimethyl-3,4,5,6-tetrahydro-2-(1H)-pyrimidone (0.616 mL, 5.10 mmol, 5.0 eq.) and 1M (in hexanes) dimethylaluminum chloride (0.51 mL, 0.510 mmol, 0.50 eq.) in 3.0 mL of anhydrous pyridine according to the procedure described for the preparation of 1 to afford a residue, which was purified by flash chromatography (40 g silica column, 100-90% dichloromethane in methanol, gradient elution) to provide 61 mg (12%) (5) as a white solid and as a mixture of diasteromers (63:37). $^1$HNMR (DMSO-d$_6$) δ 12.04 (s, 1H), 7.51 (dd, J=2.3, 0.5 Hz, 1H), 7.41-7.32 (m, 2H), 7.24-7.12 (m, 3H), 5.99-5.86 (m, 2H), 5.42 (td, J=4.8, 2.9 Hz, 1H), 5.24 (dd, J=6.0, 1.4 Hz, 1H), 4.85 (pd, J=6.3, 3.7 Hz, 1H), 4.25-4.13 (m, 2H), 4.12-3.89 (m, 3H), 3.82-3.67 (m, 1H), 1.28-1.10 (m, 9H); $^{31}$PNMR (DMSO-d$_6$) δ$_P$ 3.51, 3.48. LCMS m/z 515 (M+H)$^+$. HR-ESIMS m/z calcd. for C$_{20}$H$_{27}$N$_4$O$_{10}$P·H, 515.1538, found 515.1536. HPLC purity by Method B: 95% at 254 nm.

v. Synthesis of ethyl ((((2R,3S,4R,5R)-5-(3,5-di-oxo-4,5-dihydro-1,2,4-triazin-2(3H)-yl)-3,4-dihydroxytetrahydrofuran-2-yl)methoxy)-(phenoxy)phosphoryl)-L-alaninate (6)

vi. Synthesis of methyl ((((2R,3S,4R,5R)-5-(3,5-dioxo-4,5-dihydro-1,2,4-triazin-2(3H)-yl)-3,4-dihydroxytetrahydrofuran-2-yl)methoxy)-(phenoxy)phosphoryl)-L-alaninate (7)

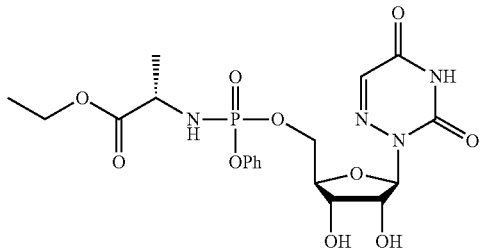

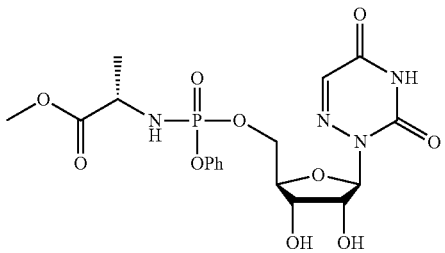

(1) Preparation of ethyl ((S)-(perfluorophenoxy)-(phenoxy)phosphoryl)-L-alaninate (27e)

(1) Preparation of methyl ((S)-(perfluorophenoxy)-(phenoxy)phosphoryl)-L-alaninate (27F)

Intermediate 26e was prepared from commercial ethyl-L-alaninate hydrochloride 25e (6.50 g, 42.34 mmol, 1.0 eq) and phenyl phosphorodichloridate (6.94 mL, 46.58 mmol, 1.1 eq) in 70 mL of anhydrous dichloromethane with triethylamine (12.13 mL, 88.92 mmol, 2.1 eq) as base according to the procedure described for the preparation of 26a to afford 14.01 g (26e) of a colorless oil. Further, compound 27e was prepared from 26e (12.35 g, 42.34 mmol, 1.0 eq) and pentafluorophenol (8.57 g, 46.58 mmol, 1.1 eq) in 100 mL of anhydrous dichloromethane with triethylamine (6.49 mL, 46.58 mmol, 1.1 eq) as base according to the procedure described for the preparation of 27a to afford 8.28 g (45%) of a white solid and as a single diastereomer. $^1$HNMR (DMSO-d$_6$) δ 7.48-7.38 (m, 2H), 7.26 (dddt, J=9.8, 7.7, 2.3, 1.1 Hz, 3H), 6.89 (ddd, J=13.9, 9.9, 6.4 Hz, 1H), 4.12-4.04 (m, 2H), 4.04-3.92 (m, 1H), 1.30 (ddd, J=7.1, 5.0, 1.2 Hz, 3H), 1.17 (t, J=7.1 Hz, 3H). $^{19}$FNMR (DMSO-d$_6$) δ$_F$ δ −153.69-−154.18 (m, 2F), −160.26-−160.44 (m, 1F), −163.0426-−163.27 (m, 2F); $^{31}$P NMR (DMSO-d$_6$) δ 0.33. LCMS m/z 440 (M+H)$^+$.

Intermediate 26f was prepared from commercial methyl-L-alaninate hydrochloride 25f (10.0 g, 71.64 mmol, 1.0 eq.) and phenyl phosphorodichloridate (11.75 mL, 78.08 mmol, 1.1 eq.) in 140 mL of anhydrous dichloromethane with triethylamine (20.97 mL, 150.45 mmol, 2.1 eq.) as base according to the procedure described for the preparation of 26a to afford 21.34 g of a yellow oil. Further, compound 27f was prepared from 26f (19.89 g, 71.64 mmol, 1.0 eq.) and pentafluorophenol (14.51 g, 78.80 mmol, 1.1 eq.) in 120 mL of anhydrous dichloromethane with triethylamine (10.98 mL, 78.80 mmol, 1.1 eq.) as base according to the procedure described for the preparation of 27a to afford 8.39 g (28%) of a white solid and as a single diastereomer. $^1$HNMR (DMSO-d$_6$) δ 7.48-7.39 (m, 2H), 7.30-7.21 (m, 3H), 6.91 (dd, J=14.1, 9.9 Hz, 1H), 4.01 (ddq, J=10.9, 9.9, 7.1 Hz, 1H), 3.61 (s, 3H), 1.29 (dd, J=7.1, 1.2 Hz, 3H). $^{19}$F NMR (DMSO-d$_6$) δ$_F$ δ −153.39-−154.18 (m, 2F), −160.05-−160.77 (m, 1F), −163.19 (td, J=23.2, 3.6 Hz, 2F). $^{31}$PNMR (DMSO-d$_6$) δ$_P$ 0.35. LCMS m/z 426 (M+H)$^+$.

(2) Preparation of Compound 6

The final target 6 was prepared from commercial 6-azauridine (250 mg, 1.02 mmol, 1.0 eq.), 27e (537 mg, 1.22 mmol, 1.2 eq.), 1,3-dimethyl-3,4,5,6-tetrahydro-2-(1H)-pyrimidone (0.62 mL, 5.10 mmol, 5.0 eq.), and 1M (in hexanes) dimethylaluminum chloride (0.51 mL, 0.51 mmol, 0.50 eq.) in 3.0 mL of anhydrous pyridine according to the procedure described for the preparation of 1 to afford an oil, which was purified by flash chromatography (40 g silica column, 100-90% dichloromethane in methanol, gradient elution) to provide 53 mg (10%) of 6 as a white solid and as a mixture of diasteromers (68:32). $^1$HNMR (DMSO-d$_6$) δ 12.28 (s, 1H), 7.52 (dd, J=1.9, 0.5 Hz, 1H), 7.41-7.33 (m, 2H), 7.24-7.13 (m, 3H), 6.10-5.77 (m, 2H), 5.42 (dd, J=5.0, 3.8 Hz, 1H), 5.24 (dd, J=6.2, 1.6 Hz, 1H), 4.26-3.90 (m, 7H), 3.79 (dddt, J=17.0, 13.5, 9.9, 7.1 Hz, 1H), 1.29-1.11 (m, 6H). $^{31}$PNMR (DMSO-d$_6$) δ 3.48, 3.46. LCMS m/z 501 (M+H)$^+$. HR-ESIMS m/z calcd for C$_{19}$H$_{25}$N$_4$O$_{10}$P·H, 501.1381, found, 501.1378. HPLC purity 96.3% at 254 nm.

(2) Preparation of Compound 7

The final target 7 was prepared from commercial 6-azauridine (250 mg, 1.02 mmol, 1.0 eq.), 27f (520 mg, 1.22 mmol, 1.2 eq.), 1,3-dimethyl-3,4,5,6-tetrahydro-2-(1H)-pyrimidone (0.616 mL, 5.10 mmol, 5.0 eq.), and 1M (in hexanes) dimethylaluminum chloride (0.51 mL, 0.51 mmol, 0.50 eq.) in 3.0 mL of anhydrous pyridine according to the procedure described for the preparation of 1 to afford a residue, which was purified by flash chromatography (40 g silica column, 100-90% dichloromethane in methanol, gradient elution) to provide 51 mg (10%) (7) as a colorless solid and as a mixture of diasteromers (55:45). $^1$HNMR (DMSO-d$_6$) δ 12.22 (s, 1H), 7.53 (dd, J=2.9, 0.5 Hz, 1H), 7.41-7.33 (m, 2H), 7.23-7.13 (m, 3H), 6.02-5.91 (m, 2H), 5.42 (dd, J=5.1, 3.4 Hz, 1H), 5.24 (dd, J=6.2, 3.1 Hz, 1H), 4.27-3.90 (m, 5H), 3.89-3.73 (m, 1H), 3.59 (d, J=8.2 Hz, 3H), 1.27-1.18 (m, 3H). $^{31}$PNMR (DMSO-d$_6$) δ$_P$ 3.44. LCMS m/z 487 (M+H)$^+$. HR-ESIMS m/z calcd for C$_{18}$H$_{23}$N$_4$O$_{10}$P·H, 487.1225, found 487.1219. HPLC purity by Method B: 91.7% at 254 nm.

d. Synthesis of isobutyl ((((2R,3S,4R,5R)-5-(3,5-dioxo-4,5-dihydro-1,2,4-triazin-2(3H)-yl)-3,4-dihydroxytetrahydrofuran-2-yl)-methoxy)(naphthalen-1-yloxy)phosphoryl)-L-alaninate (8)

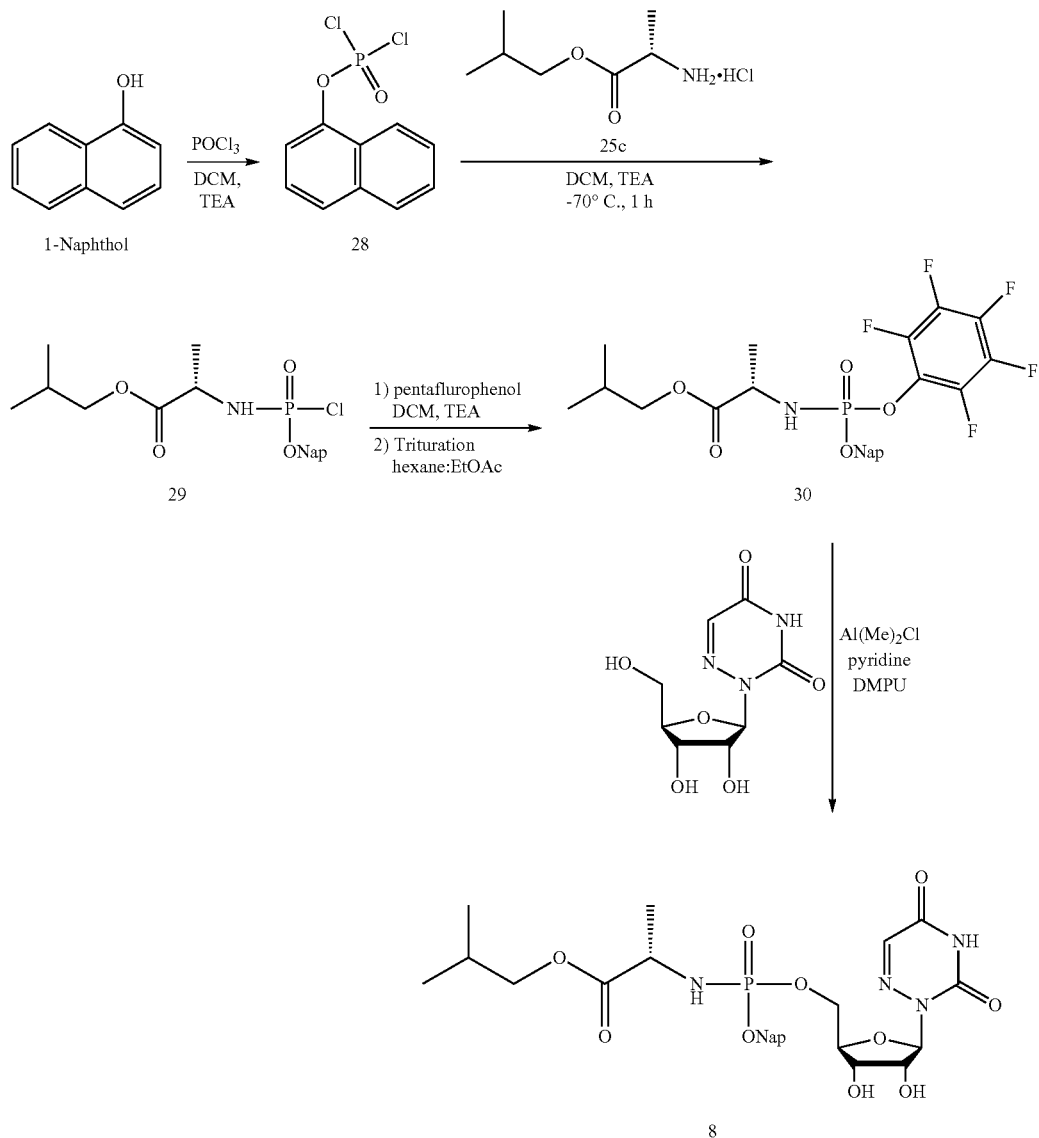

i. Preparation of naphthalen-1-yl phosphorodichloridate (28)

To a cold (−75° C.) solution of 1-naphthol (2.00 g, 13.9 mmol, 1.0 eq.) in 35 mL of anhydrous diethyl ether was added phosphorusoxychloride (1.42 mL, 15.3 mmol, 1.1 eq.) followed by a solution of triethylamine (2.13 mL, 15.3 mmol, 1.1 eq.) in 10 mL anhydrous diethyl ether dropwise over the period of 20 min at −70° C. Upon completion of addition, the reaction mixture was stirred at −70° C. under argon for 2 h and then for 18 h as it warmed to 20° C. The reaction mixture was filtered by vacuum filtration to remove triethylamine hydrochloride, which was rinsed with diethyl ether (2×20 mL). The filtrate was concentrated under vacuum to afford 3.74 g of 28 as a light tan oil. $^1$HNMR (CDCl$_3$) δ 8.13-8.06 (m, 1H), 7.94-7.87 (m, 1H), 7.84-7.77 (m, 1H), 7.66-7.51 (m, 3H), 7.47 (ddd, J=8.3, 7.6, 0.6 Hz, 1H), 4.34 (s, 1H). $^{31}$PNMR (CDCl$_3$) δ 3.81.

ii. Preparation of isobutyl ((naphthalen-1-yloxy)(perfluoro-phenoxy)phosphoryl)-L-alaninate (30)

Intermediate 29 was prepared from 25c (2.37 g, 13.05 mmol, 1.0 eq) and 28 (3.75, 14.35 mmol, 1.1 eq.) in 30 mL of anhydrous dichloromethane with triethylamine (3.82 mL, 27.4 mmol, 2.1 eq.) as base according to the procedure described for the preparation of 26a to afford 5.64 g of a light tan oil. Further, compound 30 was prepared from 29 (5.64 g, 15.30 mmol, 1.0 eq.) and pentafluorophenol (3.09 g, 16.80 mmol, 1.1 eq.) in 30 mL of anhydrous dichloromethane with triethylamine (2.34 mL, 16.80 mmol, 1.1 eq.) as base according to the procedure described for the preparation of 27a to afford a tan oil. Purification by flash chromatography (120 g silica column, 100-70% hexane in ethyl acetate, gradient elution), followed by trituration in 5-10% ethyl acetate in hexane provided 1.60 g (20%) of compound 30 as a white solid (mixture of diastereomers 55:45). $^1$HNMR (DMSO-d$_6$) δ 8.22-8.07 (m, 1H), 8.05-7.96 (m, 1H), 7.84 (ddd, J=8.1, 2.6, 1.3 Hz, 1H), 7.71-7.46 (m, 4H), 7.11 (ddd, J=15.3, 13.8, 9.9 Hz, 1H), 4.22-4.01 (m, 1H), 3.94-3.68 (m, 2H), 1.82 (dhept, J=11.7, 6.7 Hz, 1H), 1.36 (ddd, J=11.1, 7.1, 1.2 Hz, 3H), 0.94-0.75 (m, 6H). $^{19}$FNMR (DMSO-d$_6$) δ −153.32−−154.10 (m, 2F), −159.86−−160.61 (m, 1F), −163.07 (dtd, J=33.5, 23.2, 3.9 Hz, 2F). $^{31}$PNMR (DMSO-d$_6$) δ$_P$ 0.93, 0.48. LCMS m/z 518 (M+H)$^+$.

iii. Preparation of Compound 8

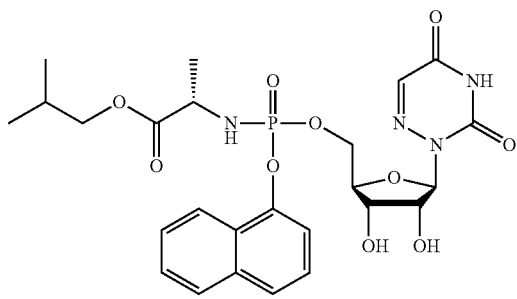

The final target 8 was prepared from commercial 6-azauridine (250 mg, 1.02 mmoles, 1.0 eq), 30 (633 mg, 1.22 mmol, 1.2 eq.), 1,3-dimethyl-3,4,5,6-tetrahydro-2-(1H)-pyrimidone (0.62 mL, 5.10 mmol, 5.0 eq.), and 1M (in hexanes) dimethylaluminum chloride (0.51 mL, 0.51 mmol, 0.50 eq.) in 3.0 mL of anhydrous pyridine according to the procedure described for the preparation of 2 to afford a residue, which was purified by flash chromatography (40 g silica column, 100-90% dichloromethane in methanol, gradient elution) to provide 8 (71 mg, 12%) as a white solid and as a mixture of diastereomers (55:45). $^1$HNMR (DMSO-d$_6$) δ 12.22 (s, 1H), 8.16-8.04 (m, 1H), 8.01-7.92 (m, 1H), 7.84-7.69 (m, 1H), 7.64-7.53 (m, 2H), 7.52-7.35 (m, 3H), 6.17 (ddd, J=12.2, 10.1, 4.7 Hz, 1H), 5.96 (d, J=3.1 Hz, 1H), 5.43 (ddd, J=6.5, 5.1, 1.1 Hz, 1H), 5.26 (d, J=6.1 Hz, 1H), 4.24 (dddd, J=15.4, 8.2, 5.5, 2.9 Hz, 2H), 4.16-3.98 (m, 3H), 3.97-3.64 (m, 3H), 1.81 (dhept, J=20.0, 6.7 Hz, 1H), 1.25 (td, J=7.0, 1.0 Hz, 3H), 0.84 (dd, J=16.6, 6.7 Hz, 6H). $^{31}$PNMR (DMSO-d$_6$) δ$_P$ 3.93, 3.72; LCMS m/z 579 (M+H)$^+$. HR-ESIMS m/z calcd for $C_{25}H_{31}N_4O_{10}P \cdot H$, 579.1851, found 579.1850. HPLC purity by Method B: 86% at 254 nm.

e. Synthesis of Compound Nos. 9-13

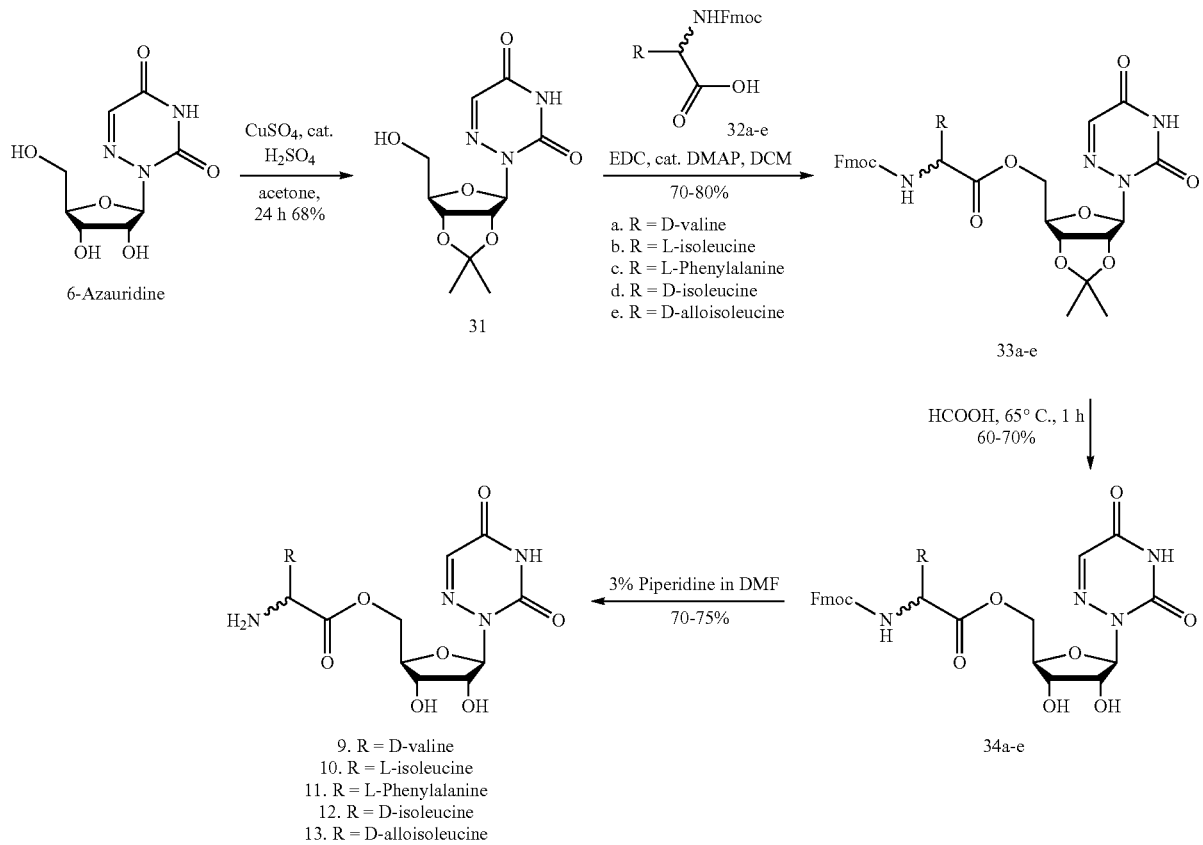

i. Preparation of 2-((3ar,4r,6r,6ar)-6-(hydroxymethyl)-2,2-dimethyltetrahydrofuro[3,4-d][1,3]dioxol-4-yl)-1,2,4-triazine-3,5(2H,4H)-dione (31)

6-Azauridine (2.7 g, 11.01 mmol, 1.0 eq.) was added to the flask containing copper sulfate (5 g, 31.33 mmol, 3.0 eq.) (after drying under vacuum at 130° C.) and suspended in 70 mL of anhydrous acetone under argon. To this mixture, 0.13 mL of concentrated sulfuric acid was added and stirred for 3 days at room temperature. The mixture was filtered and the filtrate was neutralized slowly to pH 7 by addition of 1.8 mL cold 7N ammonia in methanol. Solvent was removed by evaporation and purified on RediSep Rf Gold Silica column (0-30% methanol in dichloromethane) to afford 31 (2.14 g, 68% yield) as a white solid. $^1$HNMR (DMSO-$d_6$) δ 12.25 (s, 1H), 7.54 (s, 1H), 6.04 (d, J=1.5 Hz, 1H), 4.98 (dd, J=6.2, 1.5 Hz, 1H), 4.82 (t, J=5.9 Hz, 1H), 4.68 (dd, J=6.2, 2.8 Hz, 1H), 4.01 (td, J=6.8, 2.8 Hz, 1H), 3.39 (t, J=6.2 Hz, 2H), 1.45 (s, 3H), 1.27 (s, 3H).

ii. Synthesis of ((2r,3s,4r,5r)-5-(3,5-dioxo-4,5-dihydro-1,2,4-triazin-2(3H)-yl)-3,4-dihydroxytetrahydrofuran-2-yl) methyl-D-valinate (9)

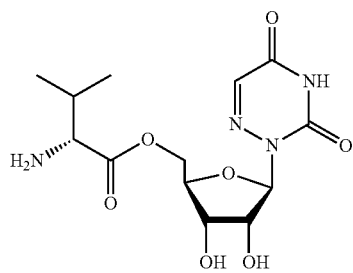

(1) Preparation of ((3ar,4r,6r,6ar)-6-(3,5-dioxo-4,5-dihydro-1,2,4-triazin-2(3H)-yl)-2,2-dimethyltetrahydrofuro[3,4-d][1,3]dioxol-4-yl)methyl (((9H-fluoren-9-yl)methoxy)carbonyl)-D-valinate (33a)

To a solution of intermediate 31 (64.0 mg, 0.22 mmol, 1.0 eq.) in anhydrous dichloromethane (5 mL) and DMPU (0.1 mL) was added N-(3-dimethylaminopropyl)-N-ethylcarbodiimide hydrochloride (64.5 mg, 0.34 mmol, 1.5 eq.) and 32a (114 mg, 0.34 mmol, 1.5 eq.). The reaction mixture was stirred for 5 min at room temperature followed by addition of 4-(dimethylamino)pyridine (33 mg, 0.27 mmol, 1.2 eq.) and further the mixture was stirred for 18 h at room temperature. The mixture was concentrated under vacuum and purified by column chromatography (0-40% ethyl acetate in dichlorometane) to afford 33a (88 mg, 64.7% yield) as a white foamy solid. $^1$HNMR (DMSO-$d_6$) δ 12.27 (s, 1H), 7.87 (d, J=7.5 Hz, 2H), 7.78-7.66 (m, 3H), 7.52 (s, 1H), 7.40 (td, J=7.5, 1.1 Hz, 2H), 7.30 (dt, J=7.6, 1.6 Hz, 2H), 6.07 (d, J=1.3 Hz, 1H), 5.03 (dd, J=6.1, 1.4 Hz, 1H), 4.75 (dd, J=6.1, 2.3 Hz, 1H), 4.34-4.08 (m, 5H), 3.91 (dd, J=8.2, 6.4 Hz, 1H), 2.03 (dt, J=13.5, 6.5 Hz, 1H), 1.43 (s, 3H), 1.25 (s, 3H), 0.87 (t, J=6.8 Hz, 6H).

(2) Preparation of ((2r,3s,4r,5r)-5-(3,5-dioxo-4,5-dihydro-1,2,4-triazin-2(3H)-yl)-3,4-dihydroxytetrahydrofuran-2-yl)-methyl(((9H-fluoren-9-yl)methoxy)carbonyl)-D-valinate (34a)

Formic acid (1 mL, 50% v/v in water) was added to 33a (80 mg, 0.13 mmol) and the mixture was warmed to 65° C. and stirred for 90 min. TLC showed complete consumption of starting material and a new spot with lower Rf was observed. The formic acid was removed by evaporation and the residue was purified by column chromatography (0-30% methanol in dichloromethane) to afford 34a (66 mg, 88.3% yield) as a white solid. $^1$HNMR (DMSO-$d_6$) δ 12.23 (s, 1H), 7.87 (d, J=7.5 Hz, 2H), 7.80-7.64 (m, 3H), 7.53 (s, 1H), 7.40 (t, J=7.4 Hz, 2H), 7.31 (td, J=7.2, 6.8, 4.1 Hz, 2H), 5.90 (d, J=2.8 Hz, 1H), 5.40 (d, J=4.9 Hz, 1H), 5.23 (d, J=6.2 Hz, 1H), 4.32 (t, J=7.5 Hz, 1H), 4.26 (d, J=6.2 Hz, 2H), 4.23-4.16 (m, 2H), 4.06 (q, J=5.9 Hz, 1H), 4.01-3.90 (m, 3H), 2.13-1.88 (m, 1H), 0.85 (dd, J=6.9, 1.9 Hz, 6H).

(3) Preparation of Compound 9

A solution of piperidine (0.21 mL, 0.11 mmol, 5% by volume in DMF) was added to a vial containing 34a (60 mg, 0.11 mmol) and stirred for 15 min at room temperature. TLC showed completion of starting material and presence of a new spot. The mixture was then concentrated to remove DMF and residue was purified by column chromatography (0-20% methanol in dichloromethane) to afford 9 (28 mg, 76.8% yield) as a foamy white solid. $^1$HNMR (DMSO-$d_6$) δ 7.52 (s, 1H), 5.89 (d, J=2.9 Hz, 1H), 5.40 (s, 1H), 5.21 (s, 2H), 4.28 (dd, J=9.5, 5.1 Hz, 1H), 4.19 (dd, J=5.1, 2.9 Hz, 1H), 4.05 (t, J=5.4 Hz, 1H), 3.97 (dd, J=9.5, 5.7 Hz, 2H), 3.14 (d, J=5.2 Hz, 1H), 1.81 (dq, J=13.2, 6.8 Hz, 1H), 0.80 (dd, J=23.8, 6.8 Hz, 6H). $^{13}$C NMR (DMSO-$d_6$) δ 175.2, 157.5, 149.0, 136.8, 136.72, 90.3, 72.9, 70.8, 64.6, 59.6, 32.1, 19.5, 17.7. HR-ESIMS m/z calcd for $C_{13}H_{21}N_4O_7$ [M+H]$^+$ 345.1405, found 345.1406. HPLC purity by Method A: 96% at 254 nm.

iii. Synthesis of ((2r,3s,4r,5r)-5-(3,5-dioxo-4,5-dihydro-1,2,4-triazin-2(3H)-yl)-3,4-dihydroxytetrahydrofuran-2-yl)methyl L-isoleucinate (10)

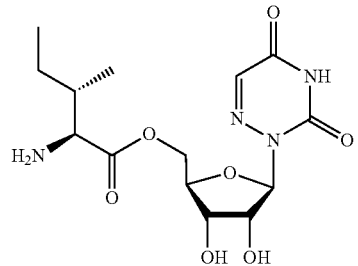

(1) Preparation of ((3ar,4r,6r,6ar)-6-(3,5-dioxo-4,5-dihydro-1,2,4-triazin-2(3H)-yl)-2,2-dimethyltetrahydrofuro[3,4-d][1,3]dioxol-4-yl)methyl-(((9H-fluoren-9-yl)methoxy)carbonyl)-L-isoleucinate (33b)

Intermediate 33b was synthesized from 31 (60 mg, 0.21 mmol, 1.0 eq.), 32b (112 mg, 0.32 mmol, 1.4 eq.) and N-(3-dimethylaminopropyl)-N-ethylcarbodiimide hydrochloride (61 mg, 0.32 mmol, 1.4 eq.) and 4-(dimethylamino)pyridine (31 mg, 0.25 mmol, 1.2 eq.) using similar procedure as for 33a and afforded 33b as a white solid (99 mg, 75.7% yield). $^1$HNMR (DMSO-$d_6$) δ 12.28 (s, 1H), 7.87 (d, J=7.5 Hz, 2H), 7.81-7.64 (m, 3H), 7.54 (s, 1H), 7.43-7.22 (m, 4H), 6.08 (s, 1H), 5.03 (d, J=6.0 Hz, 1H), 4.78-4.68 (m, 1H), 4.23 (q, J=8.4 Hz, 5H), 4.10 (dd, J=9.5, 3.3 Hz, 1H), 4.03-3.87 (m, 1H), 1.75 (d, J=14.0 Hz, 1H), 1.44 (s, 3H), 1.38-1.29 (m, 1H), 1.25 (s, 3H), 1.16 (td, J=7.1, 1.0 Hz, 1H), 0.79 (dd, J=9.1, 6.9 Hz, 6H).

(2) Preparation of ((2r,3s,4r,5r)-5-(3,5-dioxo-4,5-dihydro-1,2,4-triazin-2(3H)-yl)-3,4-dihydroxytetrahydrofuran-2-yl)methyl (((9H-fluoren-9-yl)methoxy)carbonyl)-L-isoleucinate (34b)

Intermediate 34b was synthesized from 33b (90 mg, 0.15 mmol) and formic acid (2 mL, 50% aqueous solution) using similar procedure as for 34a and afforded 34b as a white solid (74 mg, 88% yield). ¹HNMR (DMSO-d₆) δ 12.23 (s, 1H), 7.87 (d, J=7.5 Hz, 2H), 7.72 (t, J=7.3 Hz, 3H), 7.51 (s, 1H), 7.45-7.36 (m, 2H), 7.33-7.26 (m, 2H), 5.90 (d, J=3.2 Hz, 1H), 5.39 (d, J=5.1 Hz, 1H), 5.22 (d, J=6.0 Hz, 1H), 4.36-4.14 (m, 4H), 4.12-3.92 (m, 4H), 3.37 (s, 2H), 1.79 (d, J=7.8 Hz, 1H), 1.40-1.28 (m, 1H), 1.19 (dt, J=14.1, 7.4 Hz, 1H), 0.87-0.73 (m, 6H).

(3) Preparation of Compound 10

Compound 10 was synthesized from 34b (73 mg, 0.126 mmol) and piperidine (1 mL of 5% solution v/v in DMF) using similar procedure for 9 and afforded 10 as a white solid in 37 mg, 82% yield. ¹HNMR (DMSO-d₆) δ 7.49 (s, 1H), 5.89 (d, J=3.2 Hz, 1H), 5.38 (s, 1H), 5.22 (s, 2H), 4.30-4.16 (m, 2H), 4.09-3.92 (m, 3H), 3.17 (d, J=5.4 Hz, 1H), 1.64-1.49 (m, 1H), 1.44-1.27 (m, 1H), 1.16-0.99 (m, 1H), 0.79 (dd, J=8.3, 7.0 Hz, 6H). ¹³C NMR (DMSO-d₆) δ 175.25, 157.38, 149.02, 136.84, 136.78, 90.17, 90.09, 81.27, 72.87, 70.95, 64.48, 58.98, 38.97, 24.62, 15.98, 11.85. HR-ESIMS m/z calcd for [M+H]⁺ $C_{14}H_{23}N_4O_7$ 359.1561, found, 359.1568. HPLC purity by Method A: 96% at 254 nm.

iv. Synthesis of ((2r,3s,4r,5r)-5-(3,5-dioxo-4,5-dihydro-1,2,4-triazin-2(3H)-yl)-3,4-dihydroxytetrahydrofuran-2-yl)methyl L-phenylalaninate (11)

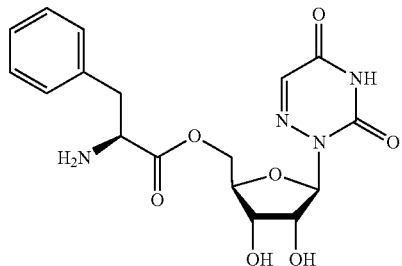

(1) Preparation of ((3ar,4r,6r,6ar)-6-(3,5-dioxo-4,5-dihydro-1,2,4-triazin-2(3H)-yl)-2,2-dimethyltetrahydrofuro[3,4-d][1,3]dioxol-4-yl)methyl-(((9H-fluoren-9-yl)methoxy)carbonyl)-L-phenylalaninate (33c)

Intermediate 33c was synthesized from 31 (76 mg, 0.27 mmol, 1.0 eq.), 32c (155 mg, 0.40 mmol, 1.5 eq.), N-(3-dimethylaminopropyl)-N-ethylcarbodiimide hydrochloride (77 mg, 0.40 mmol, 1.5 eq.) and 4-(dimethylamino)pyridine (39 mg, 0.32 mmol, 1.2 eq.) using similar procedure as for 33a to afford 33c as a white solid (119 mg, 68% yield). ¹H NMR (DMSO-d₆) δ 12.29 (s, 1H), 7.90-7.80 (m, 3H), 7.62 (dd, J=7.4, 2.9 Hz, 2H), 7.53 (s, 1H), 7.39 (t, J=7.5 Hz, 2H), 7.34-7.11 (m, 7H), 6.06 (d, J=1.3 Hz, 1H), 4.99 (dd, J=6.2, 1.3 Hz, 1H), 4.69 (dd, J=6.0, 2.4 Hz, 1H), 4.29-4.06 (m, 8H), 3.01 (dd, J=13.8, 5.1 Hz, 1H), 2.92-2.82 (m, 1H), 1.43 (s, 3H), 1.24 (s, 3H).

(2) Preparation of ((2r,3s,4r,5r)-5-(3,5-dioxo-4,5-dihydro-1,2,4-triazin-2(3H)-yl)-3,4-dihydroxytetrahydrofuran-2-yl)methyl (((9H-fluoren-9-yl)methoxy)carbonyl)-L-phenylalaninate (34c)

Intermediate 34c was synthesized from 33c (100 mg, 0.15 mmol) and formic acid (3 mL of 50% aqueous solution) using similar procedure as for 34a to afford 34c as a white solid (80 mg, 85% yield). ¹HNMR (DMSO-d₆) δ 12.23 (s, 1H), 7.85 (t, J=8.0 Hz, 3H), 7.61 (d, J=7.5 Hz, 2H), 7.48 (s, 1H), 7.38 (t, J=7.5 Hz, 2H), 7.33-7.09 (m, 7H), 5.91 (d, J=3.1 Hz, 1H), 5.40 (d, J=5.1 Hz, 1H), 5.22 (d, J=6.1 Hz, 1H), 4.32 (d, J=9.0 Hz, 1H), 4.20 (dd, J=6.6, 4.3 Hz, 3H), 4.17-4.11 (m, 1H), 4.08-3.92 (m, 3H), 3.05 (dd, J=13.8, 4.7 Hz, 1H), 2.87 (dd, J=13.8, 10.3 Hz, 1H).

(3) Preparation of Compound 11

Compound 11 was synthesized from 34c (75 mg, 0.12 mmol) and piperidine (1 mL of 5% v/v solution in DMF) using similar procedure as for 9 to afford 11 as a white solid (34 mg, 64% yield, 9:1 diastereomeric ratio). ¹HNMR (DMSO-d₆) δ 7.53 (s, 1H), 7.50 (s, 1H), 7.22 (dd, J=8.2, 6.3 Hz, 2H), 7.16 (td, J=6.8, 6.3, 1.8 Hz, 3H), 5.90 (d, J=3.1 Hz, 1H), 5.38 (s, 1H), 5.22 (s, 3H), 4.26-4.16 (m, 2H), 4.03 (t, J=5.4 Hz, 1H), 4.00-3.87 (m, 2H), 3.57 (dd, J=7.3, 6.2 Hz, 1H), 2.86 (dd, J=13.4, 6.0 Hz, 1H), 2.75 (dd, J=13.4, 7.1 Hz, 1H). HR-ESIMS m/z calcd. for [M+H]⁺ $C_{17}H_{21}N_4O_7$ 393.1405, found 393.1396. HPLC purity by Method B: >99% at 254 nm.

v. Synthesis of ((2r,3s,4r,5r)-5-(3,5-dioxo-4,5-dihydro-1,2,4-triazin-2(3H)-yl)-3,4-dihydroxytetrahydrofuran-2-yl)methyl D-isoleucinate (12)

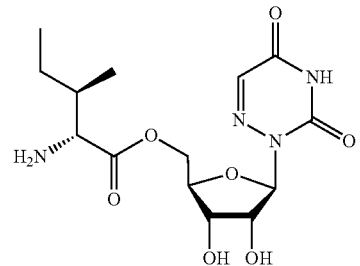

(1) Preparation of ((3ar,4r,6r,6ar)-6-(3,5-dioxo-4,5-dihydro-1,2,4-triazin-2(3H)-yl)-2,2-dimethyltetrahydrofuro[3,4-d][1,3]dioxol-4-yl)methyl (((9H-fluoren-9-yl)methoxy)carbonyl)-D-isoleucinate (33d)

Intermediate 33d was synthesized from 31 (84 mg, 0.29 mmol, 1.0 eq.), 32d (156 mg, 0.44 mmol, 1.5 eq.), N-(3-dimethylaminopropyl)-N-ethylcarbodiimide hydrochloride (85 mg, 0.44 mmol, 1.5 eq.) and DMAP (43 mg, 0.35 mmol, 1.2 eq.) using similar procedure as for 33a and afforded 33d as a white solid (86 mg, 47% yield). ¹HNMR (DMSO-d₆) δ 12.27 (s, 1H), 7.92-7.82 (m, 2H), 7.79-7.66 (m, 3H), 7.52 (s, 1H), 7.39 (d, J=7.5 Hz, 2H), 7.30 (t, J=7.4 Hz, 2H), 6.07 (d, J=1.3 Hz, 1H), 5.03 (d, J=6.2 Hz, 1H), 4.74 (dd, J=6.1, 2.5 Hz, 1H), 4.36-4.05 (m, 5H), 4.03-3.87 (m, 1H), 1.77 (s, 1H), 1.43 (s, 3H), 1.38 (d, J=3.4 Hz, 1H), 1.25 (s, 3H), 0.81 (ddd, J=12.2, 8.0, 4.7 Hz, 6H).

(2) Preparation of ((2r,3s,4r,5r)-5-(3,5-dioxo-4,5-dihydro-1,2,4-triazin-2(3H)-yl)-3,4-dihydroxytetrahydrofuran-2-yl)methyl (((9H-fluoren-9-yl)methoxy)carbonyl)-D-isoleucinate (34d)

Intermediate 34d was synthesized from 33d (80 mg, 0.13 mmol) and formic acid (2 mL of 50% aqueous solution) using similar procedure as for 34a and afforded 34d as a white solid (47 mg, 63% yield). $^1$HNMR (DMSO-$d_6$) δ 12.20 (s, 1H), 7.87 (d, J=7.6 Hz, 2H), 7.82-7.66 (m, 3H), 7.53 (s, 1H), 7.40 (t, J=7.5 Hz, 2H), 7.31 (td, J=7.4, 2.6 Hz, 2H), 5.90 (d, J=2.7 Hz, 1H), 5.41 (d, J=4.9 Hz, 1H), 5.23 (d, J=6.1 Hz, 1H), 4.45-4.15 (m, 5H), 4.10-3.86 (m, 4H), 1.76 (s, 1H), 1.34 (dd, J=12.7, 6.1 Hz, 1H), 1.19 (dd, J=14.5, 7.3 Hz, 1H), 0.79 (q, J=7.0 Hz, 6H).

(3) Preparation of Compound 12

Compound 10 was synthesized from 34d (45 mg, 0.07 mmol) and piperidine (1 mL of 5% v/v solution in DMF), using similar procedure as for 9 to afford 12 as a white solid (23 mg, 82% yield). $^1$HNMR (DMSO-$d_6$) δ 7.51 (s, 1H), 5.89 (d, J=2.8 Hz, 1H), 5.40 (d, J=5.0 Hz, 1H), 5.21 (s, 1H), 4.30-4.20 (m, 1H), 4.20-4.14 (m, 1H), 4.05 (t, J=5.4 Hz, 1H), 3.99-3.93 (m, 2H), 3.17 (d, J=5.4 Hz, 1H), 1.60-1.48 (m, 1H), 1.36 (ddd, J=13.5, 7.5, 4.4 Hz, 1H), 1.08 (ddd, J=13.5, 8.9, 7.3 Hz, 1H), 0.84-0.71 (m, 6H). HR-ESIMS m/z calcd. for $C_{14}H_{23}N_4O_7[M+H]^+$ 359.1561, found 359.1563. HPLC purity by Method A: 98% at 254 nm.

vi. Synthesis of ((2r,3s,4r,5r)-5-(3,5-dioxo-4,5-dihydro-1,2,4-triazin-2(3)-yl)-3,4-dihydroxytetrahydrofuran-2-yl)methyl D-alloisoleucinate (13)

(2) Preparation of ((2r,3s,4r,5r)-5-(3,5-dioxo-4,5-dihydro-1,2,4-triazin-2(3H)-yl)-3,4-dihydroxytetrahydrofuran-2-yl)methyl (((9H-fluoren-9-yl)methoxy)carbonyl)-D-alloisoleucinate (34e)

Intermediate 34e was synthesized from 33e (119 mg, 0.19 mmol) and formic acid (2 mL of 50% aqueous solution) using similar procedure as for 34a to afford 34e as a white solid (84 mg, 75% yield). $^1$HNMR (DMSO-$d_6$) δ 12.24 (s, 1H), 7.88 (d, J=7.5 Hz, 2H), 7.80-7.66 (m, 3H), 7.53 (s, 1H), 7.44-7.20 (m, 4H), 5.90 (d, J=2.7 Hz, 1H), 5.41 (d, J=4.9 Hz, 1H), 5.23 (d, J=6.2 Hz, 1H), 4.41-4.09 (m, 5H), 4.05-3.93 (m, 2H), 1.84 (dt, J=13.1, 6.8 Hz, 1H), 1.41-1.19 (m, 2H), 1.12 (dt, J=13.9, 7.2 Hz, 1H), 0.91-0.68 (m, 6H).

(3) Preparation of Final Target 13

Compound 13 was synthesized from 34e (80 mg, 0.14 mmol) and piperidine (1 mL of 5% v/v in DMF) using similar procedure as for 9 to afford 13 as a white solid (34 mg, 69% yield). $^1$HNMR (DMSO-$d_6$) δ 7.50 (d, J=0.5 Hz, 1H), 5.89 (d, J=2.7 Hz, 1H), 5.40 (d, J=4.9 Hz, 1H), 5.21 (s, 1H), 4.34-4.23 (m, 1H), 4.18 (s, 1H), 4.04 (s, 1H), 4.01-3.90 (m, 2H), 3.28 (d, J=4.4 Hz, 1H), 1.60 (dtd, J=7.7, 6.5, 4.4 Hz, 1H), 1.36 (ddd, J=13.7, 7.5, 6.3 Hz, 1H), 1.11 (dt, J=13.3, 7.4 Hz, 1H), 0.82 (t, J=7.4 Hz, 3H), 0.71 (d, J=6.9 Hz, 3H). HR-ESIMS m/z calcd. for $C_{14}H_{23}N_4O_7[M+H]^+$ 359.1561 found 359.1562. HPLC purity by Method B: >99% at 254 nm.

f. Synthesis of Compound Nos. 14-16

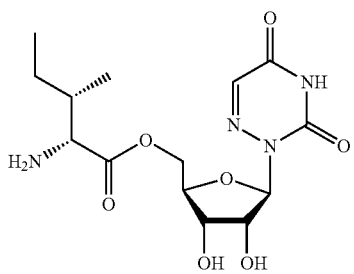

(1) Preparation of ((3ar,4r,6r,6ar)-6-(3,5-dioxo-4,5-dihydro-1,2,4-triazin-2(3H)-yl)-2,2-dimethyltetrahydrofuro[3,4-d][1,3]dioxol-4-yl)methyl (((9H-fluoren-9-yl)methoxy)carbonyl)-D-allisoleucinate (33e)

Intermediate 33e was synthesized from 31 (84. mg, 0.29 mmol, 1.0 eq.), N-(3-dimethylaminopropyl)-N-ethylcarbodiimide hydrochloride (85 mg, 0.44 mmol, 1.5 eq.) and 32e (156 mg, 0.44 mmol, 1.5 eq.) and 4-(dimethylamino)pyridine (43 mg, 0.35 mmol, 1.2 eq.) using similar procedure as for 33a to afford 33e as a white solid (123 mg, 67% yield). $^1$HNMR (DMSO-$d_6$) δ 12.27 (s, 1H), 7.87 (d, J=7.5 Hz, 2H), 7.72 (t, J=6.9 Hz, 3H), 7.51 (d, J=1.3 Hz, 1H), 7.44-7.36 (m, 2H), 7.30 (tdd, J=7.4, 3.0, 1.2 Hz, 2H), 6.07 (d, J=1.3 Hz,

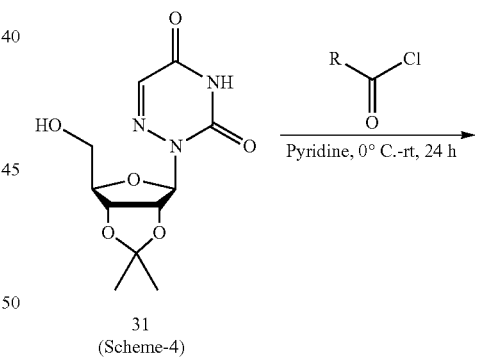

31
(Scheme-4)

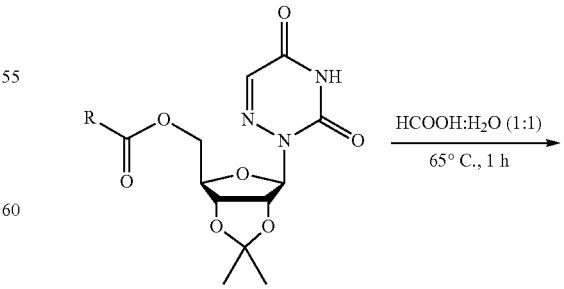

35a. R = Isopropylate
35b. R = Stearate
35c. R = Diethyl phosphonate

-continued

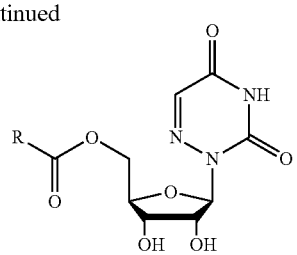

14. R = Isopropylate
15. R = Stearate
16. R = Diethyl phosphonate i. Synthesis of ((2r,3s,4r,5r)-5-(3,5-dioxo-4,5-dihydro-1,2,4-triazin-2(3H)-yl)-3,4-dihydroxytetrahydrofuran-2-yl)-methyl isobutyrate (14)

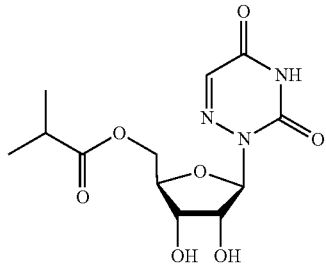

(1) Preparation of ((3ar,4r,6r,6ar)-6-(3,5-dioxo-4,5-dihydro-1,2,4-triazin-2(3H)-yl)-2,2-dimethyltetrahydrofuro[3,4-d][1,3]dioxol-4-yl)methyl isobutyrate (35a)

2-Methyl propanoyl chloride (0.11 mL, 1.05 mmol, 1.5 eq.) was added as a solution in anhydrous dichloromethane (1 mL) to a pre-stirred solution of 31 (200 mg, 0.7 mmol, 1.0 eq.) in anhydrous pyridine (5 mL, 0.70 mmol, 1.0 eq.) at 0° C. and the reaction mixture was allowed to warm to room temperature overnight. The reaction mixture was concentrated under vacuum to dryness. The residue was chromatographed (0-30% methanol in dichloromethane) to afford 35a (185 mg, 74% yield) as a white viscous solid. $^1$HNMR (DMSO-$d_6$) δ 12.26 (s, 1H), 7.53 (s, 1H), 6.06 (d, J=1.3 Hz, 1H), 5.03 (dd, J=6.1, 1.3 Hz, 1H), 4.75 (dd, J=6.1, 2.9 Hz, 1H), 4.19 (dd, J=6.5, 2.9 Hz, 1H), 4.09 (dd, J=6.4, 1.0 Hz, 2H), 2.60-2.50 (m, 1H), 1.45 (s, 3H), 1.28 (s, 3H), 1.04 (dd, J=6.9, 0.9 Hz, 6H).

(2) Preparation of Compound 14

Intermediate 35a (180 mg, 0.51 mmol) was taken in a 20 mL vial and added formic acid (2 mL, 0.51 mmol, 50% by v/v in water). The mixture was warmed to 65° C. stirred for 30 min and concentrated to dryness under vacuum at 50° C. The residue obtained was co-evaporated with methanol (2×5 mL) to remove residual formic acid. The residue was purified by flash column chromatography (0-30% methanol in dichloromethane) to afford 14 (103 mg, 64% yield) as a sticky white solid. $^1$H NMR (DMSO-$d_6$) δ 12.23 (s, 1H), 7.53 (s, 1H), 5.88 (d, J=3.0 Hz, 1H), 5.36 (d, J=5.0 Hz, 1H), 5.18 (d, J=6.2 Hz, 1H), 4.32-4.14 (m, 2H), 4.04 (q, J=5.5 Hz, 1H), 3.95 (dd, J=8.3, 5.8 Hz, 2H), 2.52 (d, J=7.0 Hz, 1H), 1.05 (dd, J=7.0, 3.4 Hz, 6H). $^{13}$C NMR (DMSO-$d_6$) δ 176.37, 156.94, 148.64, 136.87, 136.83, 90.14, 90.09, 81.23, 72.91, 70.87, 64.39, 33.58, 19.16. HR-ESIMS calcd. for [M+H]$^+$ $C_{12}H_{18}N_3O_7$ 316.1139, found 316.1138. HPLC purity by Method A: 99% at 254 nm.

ii. Synthesis of ((2r,3s,4r,5r)-5-(3,5-dioxo-4,5-dihydro-1,2,4-triazin-2(3H)-yl)-3,4-dihydroxytetrahydrofuran-2-yl)methyl stearate (15)

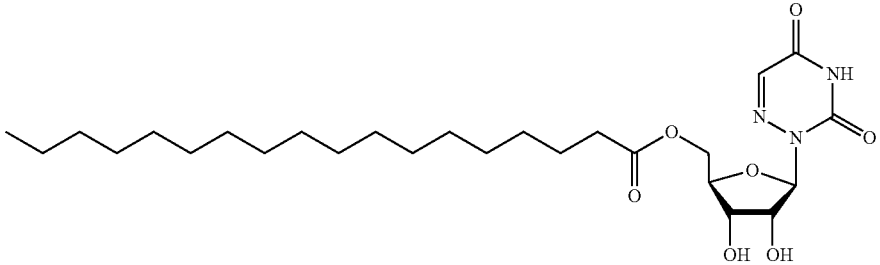

(1) Preparation of ((3ar,4r,6r,6ar)-6-(3,5-dioxo-4,5-dihydro-1,2,4-triazin-2(3H)-yl)-2,2-dimethyltetrahydrofuro[3,4-d][1,3]dioxol-4-yl)methyl stearate (35b)

Stearoyl chloride (164 mg, 0.54 mmol) was added to a solution of 31 in anhydrous pyridine (3 mL, 0.36 mmol) at 0° C. and the mixture was warmed to room temperature and stirred for 18 h. The reaction was quenched with water (1 mL) and diluted with ethyl acetate (10 mL). The organic layer was washed with water (5 mL), dried over sodium sulfate, filtered, and then the filtrate was evaporated under vacuum. The residual pyridine was removed by co-evaporation with toluene (2×5 mL). The crude residue was purified by column chromatography (0-100% ethyl acetate in dichloromethane) to afford 35b (160 mg, 80% yield) as a white solid. $^1$HNMR (DMSO-$d_6$) δ 12.27 (s, 1H), 7.52 (s, 1H), 6.06 (s, 1H), 5.01 (d, J=6.1 Hz, 1H), 4.74 (dd, J=6.1, 2.9 Hz, 1H), 4.19 (td, J=6.7, 6.0, 3.0 Hz, 1H), 4.08 (d, J=7.3

Hz, 2H), 2.25 (t, J=7.2 Hz, 2H), 1.45 (m, 5H), 1.24 (d, J=26.2 Hz, 33H), 0.83 (t, J=5.6 Hz, 3H).

(2) Preparation of Compound 15

Formic acid (1 mL, 50% v/v in water) was added to 35b (128 mg, 0.23 mmol) and mixture was heated at 65° C. with stirring for 1 h. The mixture was concentrated at 50° C. under vacuum to remove formic acid. The residue was re-dissolved in methanol (2 mL) and concentrated down with silica gel (2 g). The slurry was purified by column chromatography to yield 15 (87 mg, 72% yield) as a white solid. $^1$HNMR (DMSO-d6) δ 12.23 (s, 1H), 7.53 (s, 1H), 5.88 (d, J=3.0 Hz, 1H), 5.38 (d, J=5.0 Hz, 1H), 5.19 (d, J=6.2 Hz, 1H), 4.25 (dd, J=10.5, 4.0 Hz, 1H), 4.17 (td, J=4.8, 2.9 Hz, 1H), 4.02 (t, J=5.5 Hz, 1H), 3.98-3.86 (m, 2H), 2.25 (t, J=7.4 Hz, 2H), 1.51-1.42 (m, 3H), 1.21 (d, J=2.4 Hz, 31H), 0.89-0.77 (m, 3H). HR-ESIMS m/z calcd. for $C_{26}H_{46}N_3O_7$ 512.3330, found 512.3319. HPLC purity by Method A: 98% at 254 nm.

iii. Synthesis of (2r,3s,4r,5r)-5-(3,5-dioxo-4,5-dihydro-1,2,4-triazin-2(3H)-yl)-3,4-dihydroxytetrahydrofuran-2-yl) methyl diethyl phosphate (16)

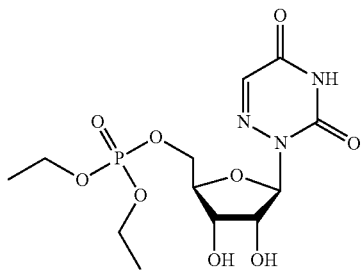

(1) Preparation of ((3ar,4r,6r,6ar)-6-(3,5-dioxo-4,5-dihydro-1,2,4-triazin-2(3)-yl)-2,2-dimethyltetrahydrofuro[3,4-d][1,3]dioxol-4-yl)methyl (diethoxyphosphoryl) formate (35c)

Compound 31 (100 mg, 0.35 mmol, 1.0 eq.) was co-evaporated with anhydrous pyridine (2×2 mL) and the residue was dried under vacuum overnight. The dried 31 was dissolved in anhydrous pyridine (5 mL), cooled to 0° C. and added 1-[chloro(ethoxy)phosphoryl]oxyethane (0.07 mL, 0.53 mmol, 1.5 eq.) dropwise under argon atmosphere. The reaction mixture was further stirred for 18 h at room temperature. On completion of the reaction, the mixture was concentrated to remove pyridine by co-evaporation with toluene (2×5 mL). The residue was purified by column chromatography (0-100% ethyl acetate in dichloromethane) to afford 35c (31 mg, 21% yield) as a colorless oil. $^1$HNMR (DMSO-$d_6$) δ 12.28 (s, 1H), 7.52 (d, J=2.7 Hz, 1H), 6.08 (d, J=2.4 Hz, 1H), 5.02 (dd, J=6.2, 2.4 Hz, 1H), 4.75 (dt, J=5.9, 2.8 Hz, 1H), 4.22 (tt, J=5.5, 2.7 Hz, 1H), 3.98 (dtt, J=21.5, 8.5, 4.5 Hz, 6H), 1.46 (d, J=2.5 Hz, 3H), 1.28 (d, J=2.5 Hz, 3H), 1.19 (ddd, J=9.0, 6.0, 1.9 Hz, 6H).

(2) Preparation of Compound 16

Compound 35c (25 mg, 0.06 mmol) dissolved in formic acid (1 mL of 50% v/v solution in water) and the mixture was heated to 65° C. for 1 h. The mixture was concentrated to remove excess formic acid with co-evaporation with methanol (2×5 mL). The residue was purified by column chromatography to yield 16 (20 mg, 88% yield) as a viscous oil. $^1$H NMR (DMSO-$d_6$) δ 12.25 (s, 1H), 7.52 (d, J=0.6 Hz, 1H), 5.90 (d, J=3.0 Hz, 1H), 5.40 (d, J=5.0 Hz, 1H), 5.23 (d, J=6.3 Hz, 1H), 4.18 (td, J=5.0, 3.1 Hz, 1H), 4.09-3.84 (m, 8H), 1.20 (tdd, J=7.0, 2.4, 0.9 Hz, 6H). $^{31}$P NMR (DMSO-$d_6$) δ −1.23. HR-ESIMS m/z calcd. for $C_{12}H_{20}N_3O_9P$ [M+H]$^+$ 382.1010, found 382.1015. HPLC purity by Method A: 99% at 254 nm.

g. Synthesis of 2-ethylbutyl ((((2r,9,4r,5r)-5-(5-amino-3-oxo-1,2,4-triazin-2(3H)-yl)-3,4-dihydroxytetrahydrofuran-2-yl)methoxy)-(phenoxy)phosphoryl)-L-alaninate (17)

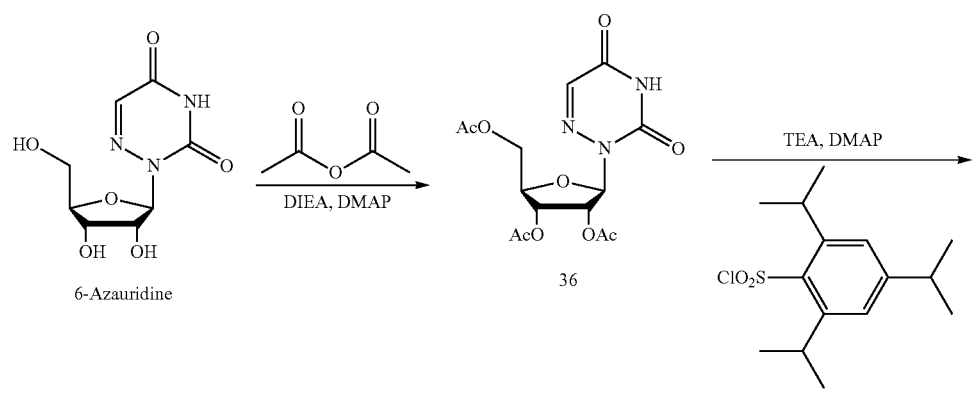

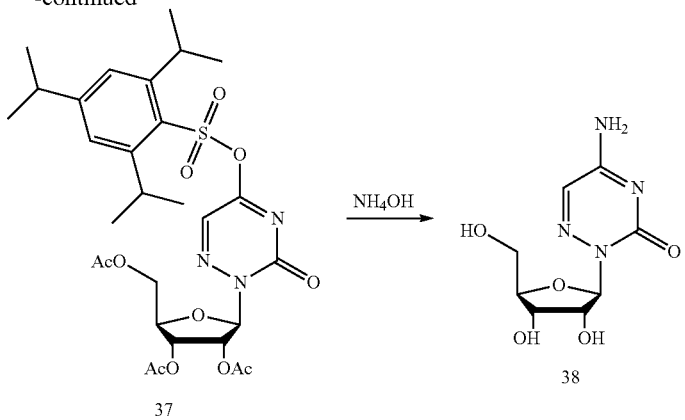

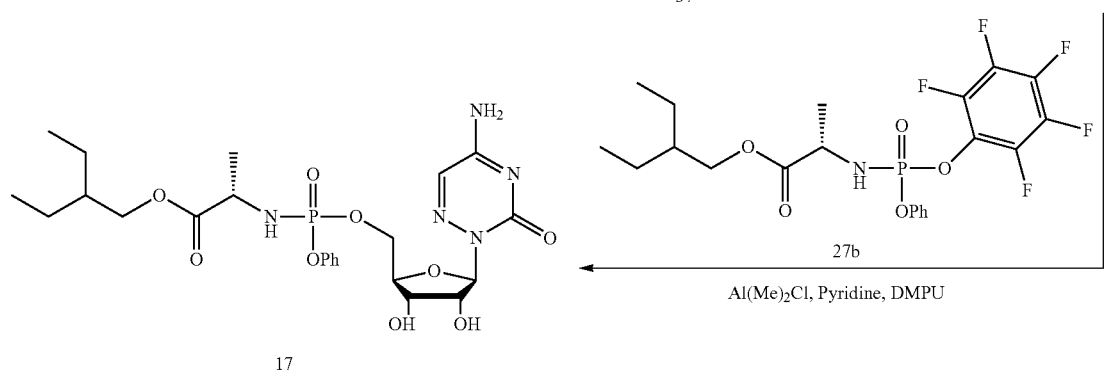

i. Preparation of (2r,3r,4r,5r)-2-(acetoxymethyl)-5-(3,5-dioxo-4,5-dihydro-1,2,4-triazin-2(3)-yl)tetrahydrofuran-3,4-diyl diacetate (36)

To a solution of 6-azauridine (2.0 g, 8.16 mmol, 1.0 eq.) in 120 mL of anhydrous acetonitrile was added 4-dimethylaminopyridine (120 mg, 0.98 mmol, 0.12 eq), N,N'-diisopropylethylamine (5.83 mL, 33.4 mmol, 4.1 eq), followed by acetic anhydride (3.08 mL, 32.6 mmol, 4.0 eq). The reaction mixture was stirred at 20° C. for 18 h and then was evaporated under reduced pressure to afford an oil, which was dissolved in 200 mL of ethyl acetate. The organic layer was washed with saturated sodium bicarbonate (2×50 mL), sat ammonium chloride (2×50 mL), followed by brine (50 mL). The organic layer was separated, dried in sodium sulfate, filtered, and then the filtrate was evaporated in vacuum to afford 2.20 g (73%) of 36 as a white foamy solid. $^1$HNMR (DMSO-d$_6$) δ 12.35 (s, 1H), 7.68 (d, J=0.6 Hz, 1H), 6.27-6.02 (m, 1H), 5.62-5.49 (m, 1H), 5.35 (ddd, J=6.0, 5.6, 0.4 Hz, 1H), 4.40-4.23 (m, 2H), 4.14-3.97 (m, 1H), 2.10 (s, 3H), 2.07 (s, 3H), 2.03 (s, 3H). HR-ESIMS m/z calcd. for C$_{14}$H$_{17}$N$_3$O$_9$·H, 372.1038, found 372.1036.

ii. Preparation of 5-amino-2-((2r,3r,4s,5r)-3,4-dihydroxy-5-(hydroxymethyl)tetrahydrofuran-2-yl)-1,2,4-triazin-3(2H)-one (38)

To a mixture of 36 (2.00 g, 5.39 mmoles, 1.0 eq), triisopropylbenzenesulfonyl chloride (4.80 g, 15.8 mmoles, 2.94 eq) and 4-dimethylaminopyridine (2.04 g, 16.7 mmoles, 3.1 eq) was added 30 mL of anhydrous acetonitrile, followed by triethylamine (1.58 mL, 11.3 mmoles, 2.1 eq). The reaction mixture was stirred at 20° C. for 24 h to afford 37, which was reacted further without isolation. To the reaction mixture containing intermediate 37 was added 28% aqueous ammonium hydroxide (103 mL, 747 mmol, 135 eq.) and then the reaction mixture was stirred at 20° C. for 3 days. The reaction mixture was evaporated under reduced pressure to afford a solid, which was purified by flash chromatography (80 g silica column, 100-80% dichloromethane in methanol, gradient elution) to provide 1.34 g of crude product as a yellow solid. Recrystallization from a mixture of boiling methanol (18 mL) and water (2 mL) gave 534 mg (40%) of 38 as a yellow crystalline solid. $^1$HNMR (DMSO-d$_6$) δ 7.95 (d, J=47.0 Hz, 2H), 7.51 (d, J=0.6 Hz, 1H), 5.98 (d, J=4.1 Hz, 1H), 5.19 (d, J=5.6 Hz, 1H), 4.98 (d, J=5.9 Hz, 1H), 4.67 (t, J=5.8 Hz, 1H), 4.21 (td, J=5.4, 4.1 Hz, 1H), 3.99 (q, J=5.5 Hz, 1H), 3.78 (td, J=5.6, 4.4 Hz, 1H), 3.56-3.36 (m, 2H).

iii. Preparation of Compound 17

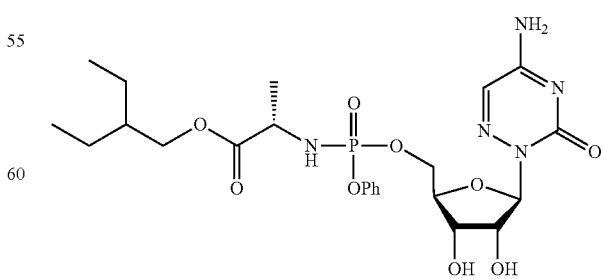

The final target 17 was prepared from 38 (200 mg, 0.819 mmol, 1.0 eq), 27b (Scheme-2) (487 mg, 0.983 mmol, 1.2 eq.), and 1M (in hexanes) dimethylaluminum chloride (0.409 mL, 0.409 mmol, 0.50 eq.) in a mixture of anhydrous pyridine (2.46 mL) and 1,3-dimethyl-3,4,5,6-tetrahydro-2-(1H)-pyrimidone (DMPU) (0.495 mL, 4.09 mmol, 5.0 eq) by the procedure described for the preparation of 2 to afford a semi-solid. Two purifications by flash chromatography (40 g and 24 g silica columns, 100-90% dichloromethane in methanol, gradient elution) provided 35 mg of a yellow gummy solid. The solid was dissolved in a mixture of 2 drops of methanol and 1.0 mL of dichloromethane. Hexane was added until a precipitate formed which was filtered by vacuum filtration to give 14 mg (3%) of a yellow solid as a single diastereomer containing residual DMPU. $^1$HNMR (DMSO-d$_6$) δ 8.05 (s, 1H), 7.95 (s, 1H), 7.51 (d, J=1.7 Hz, 1H), 7.37 (dd, J=8.6, 7.3 Hz, 1H), 7.26-7.11 (m, 3H), 6.05 (t, J=3.6 Hz, 1H), 6.02-5.92 (m, 1H), 5.35 (dd, J=5.2, 1.8 Hz, 1H), 5.18 (dd, J=6.2, 1.6 Hz, 1H), 4.25-3.73 (m, 9H), 1.60-1.16 (m, 15H), 0.94-0.78 (m, 11H); $^{31}$P NMR (DMSO-d$_6$) δ$_P$ 3.54. LCMS m/z 556 (M+H)$^+$. HR-ESIMS m/z calcd for $C_{23}H_{34}N_5O_9P \cdot H$, 556.2167, found 556.2162. HPLC purity by Method B: 94% at 254 nm.

h. Synthesis of Compound Nos. 18-24

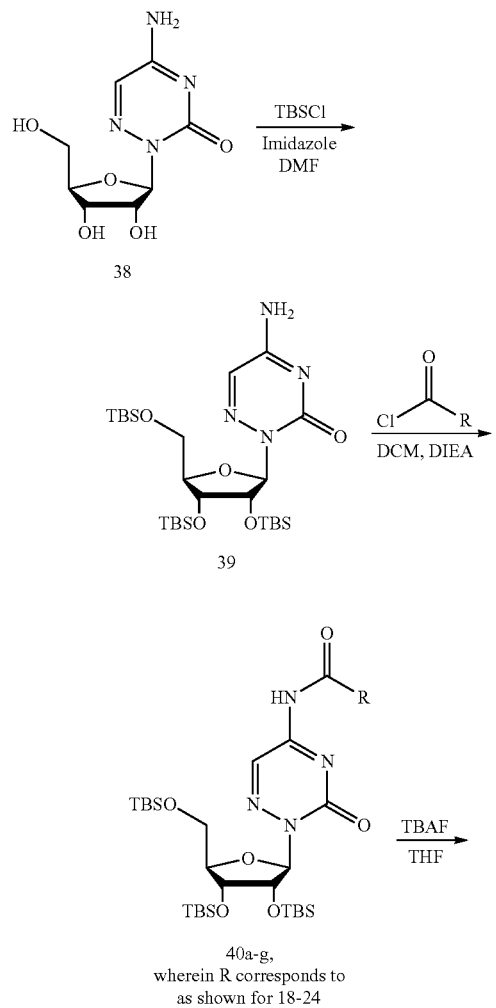

40a-g,
wherein R corresponds to
as shown for 18-24

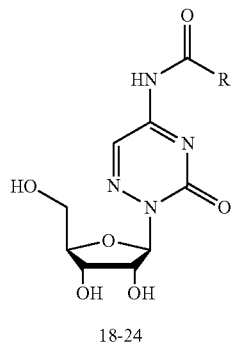

18-24 i. Preparation of 5-amino-2-((2r,3r,4r,5r)-3,4-bis ((tert-butyl-dimethylsilyl)oxy)-5-(((tert-butyldimethylsilyl)oxy)-methyl)tetrahydrofuran-2-yl)-1,2,4-triazin-3(2H)-one (39)

To a solution of 38 (Scheme-6) (225 mg, 0.92 mmol, 1.0 eq.) in 4.0 mL of anhydrous N,N'-dimethylformamide was added imidazole (376 mg, 5.53 mmol, 6.0 eq.), followed by tetrabutyldimethylchlorosilane (555 mg, 3.69 mmol, 4.0 eq.). The reaction mixture was stirred at 20° C. for 18 h. The reaction mixture was diluted with 100 mL of dichloromethane, washed with water (2×50 mL), saturated sodium bicarbonate (2×50 mL), saturated ammonium chloride (2×50 mL), followed by brine (50 mL). The organic layer was separated, dried over sodium sulfate, filtered, and then the filtrate was evaporated under reduced pressure to afford an oil. Purification by flash chromatography (40 g silica column, 100-0% hexane in ethyl acetate, gradient elution) provided 91 mg (17%) of 39 as a yellow solid. $^1$HNMR (DMSO-d$_6$) δ 8.04 (s, 1H), 7.89 (s, 1H), 7.53 (d, J=0.6 Hz, 1H), 6.03 (d, J=5.3 Hz, 1H), 4.49 (dd, J=5.4, 4.5 Hz, 1H), 4.27 (dd, J=4.6, 3.4 Hz, 1H), 3.89-3.81 (m, 1H), 3.71-3.58 (m, 2H), 0.92 (s, 9H), 0.88 (s, 9H), 0.84 (s, 9H), 0.11 (d, J=5.0 Hz, 6H), 0.05--0.00 (m, 9H), -0.05 (s, 3H). LCMS m/z 587 (M+H)$^+$.

ii. Synthesis of N-(2-((2r,3r,4s,5r)-3,4-dihydroxy-5-(hydroxymethyl)-tetrahydrofuran-2-yl)-3-oxo-2,3-dihydro-1,2,4-triazin-5-yl)-2-propylpentanamide (18)

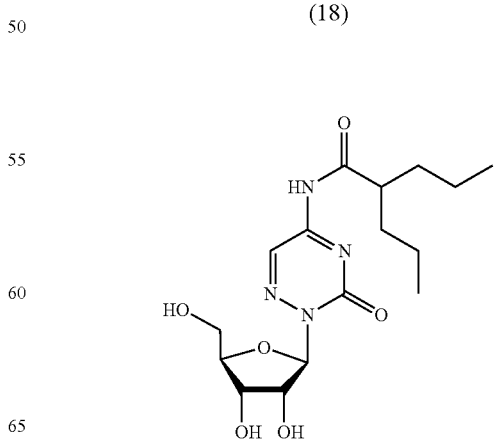

(1) Preparation of N-(2-((2r,3r,4r,5r)-3,4-bis((tert-butyl-dimethylsilyl)oxy)-5-(((tert-butyldimethylsilyl)oxy)-methyl)tetrahydrofuran-2-yl)-3-oxo-2,3-dihydro-1,2,4-triazin-5-yl)-2-propylpentanamide (40a)

To a solution of 39 (205 mg, 0.35 mmol, 1.0 eq) in 5.0 mL of anhydrous dichloromethane was added a solution of 2,2-di-n-propylacetyl chloride (62 mg, 0.38 mmol, 1.1 eq.) in 1.0 mL of anhydrous dichloromethane, followed by N,N'-diisopropylethylamine (0.067 mL, 0.38 mmol, 1.1 eq). The reaction mixture was irradiated with microwaves at 120° C. for 1 h and then evaporated under reduced pressure to afford an oil, which was purified by flash chromatography (40 g, silica column, 100-70% hexane in ethyl acetate, gradient elution) to provide 223 mg (89%) of 40a as a colorless solid. $^1$HNMR (CDCl$_3$) δ 8.94 (s, 1H), 8.19 (s, 1H), 6.24 (d, J=4.1 Hz, 1H), 4.51 (t, J=4.3 Hz, 1H), 4.33 (t, J=4.5 Hz, 1H), 4.04 (q, J=4.4 Hz, 1H), 3.81-3.59 (m, 2H), 2.44-2.32 (m, 1H), 1.72-1.60 (m, 2H), 1.55-1.45 (m, 2H), 1.42-1.28 (m, 4H), 0.98-0.82 (m, 33H), 0.13--0.05 (m, 18H). LCMS m/z 728 (M+H)$^+$.

(2) Preparation of Compound 18

To a cold (0° C.) solution of 40a (210 mg, 0.30 mmol, 1.0 eq.) in 10.0 mL of anhydrous tetrahydrofuran was added a 1M solution of tetrabutylammonium fluoride (0.931 mL, 0.93 mmol, 3.1 eq.) in tetrahydrofuran. The reaction mixture was stirred for 18 h as it warmed to 20° C. The reaction mixture was evaporated under reduced pressure to afford a residue, which was purified by flash chromatography (40 g silica column, 100-95% dichloromethane in methanol, gradient elution) to provide 60 mg (54%) of 18 as a white solid. $^1$HNMR (DMSO-d$_6$) δ 11.46 (s, 1H), 8.80 (d, J=0.5 Hz, 1H), 6.05 (d, J=3.6 Hz, 1H), 5.31 (d, J=5.3 Hz, 1H), 5.05 (d, J=6.0 Hz, 1H), 4.65 (dd, J=6.1, 5.5 Hz, 1H), 4.28 (td, J=5.2, 3.6 Hz, 1H), 4.08 (q, J=5.6 Hz, 1H), 3.86 (td, J=5.7, 4.2 Hz, 1H), 3.60-3.37 (m, 2H), 2.67 (tt, J=9.1, 5.0 Hz, 1H), 1.57 (dtd, J=13.0, 8.8, 7.1 Hz, 2H), 1.46-1.34 (m, 2H), 1.33-1.20 (m, 4H), 0.88 (t, J=7.3 Hz, 6H). LCMS m/z 371 (M+H)$^+$. HR-ESIMS m/z calcd for C$_{16}$H$_{26}$N$_4$O$_6$·H, 371.19251, found 371.19248. HPLC purity by Method B: 99% at 254 nm.

iii. Synthesis of N-(2-((2r,3r,4s,5r)-3,4-dihydroxy-5-(hydroxy-methyl)tetrahydrofuran-2-yl)-3-oxo-2,3-dihydro-1,2,4-triazin-5-yl)dodecanamide (19)

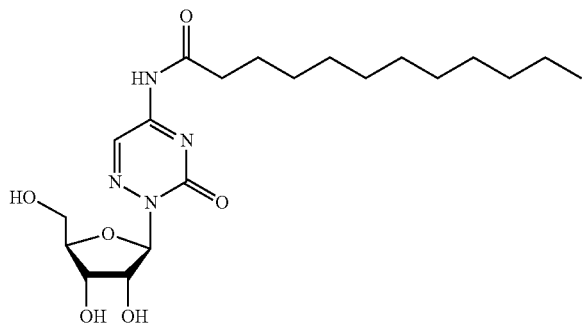

(1) Preparation of N-(2-((2r,3r,4r,5r)-3,4-bis((tert-butyl-dimethylsilyl)oxy)-5-(((tert-butyldimethylsilyl)oxy)-methyl)tetrahydrofuran-2-yl)-3-oxo-2,3-dihydro-1,2,4-triazin-5-yl)dodecanamide (40b)

Intermediate 40b was prepared from 39 (85 mg, 0.145 mmol, 1.0 eq.) and dodecyl chloride (32 mg, 0.145 mmol, 1.0 eq.) in 2.0 mL of anhydrous dichloromethane with N,N'-diisopropylethylamine (0.025 mL, 0.145 mmol, 1.0 eq.) as base according to the procedure described for the preparation of 40a to afford a residue. Purification by flash chromatography (40 g silica column, 100-79% hexane in ethyl acetate, gradient elution) provided 81 mg (73%) of a colorless tacky solid. $^1$HNMR (CDCl$_3$) δ 8.94 (s, 1H), 8.57 (s, 1H), 6.25 (d, J=4.4 Hz, 1H), 4.53 (t, J=4.5 Hz, 1H), 4.32 (t, J=4.4 Hz, 1H), 4.05 (q, J=4.4 Hz, 1H), 3.83-3.61 (m, 2H), 2.51 (t, J=7.4 Hz, 2H), 1.70 (q, J=7.3 Hz, 2H), 1.28 (d, J=3.5 Hz, 16H), 0.93 (s, 9H), 0.91-0.85 (m, 21H), 0.11 (d, J=2.6 Hz, 6H), 0.07-0.00 (m, 9H), –0.02 (s, 3H). LCMS m/z 769 (M+H)$^+$.

(2) Preparation of Compound 19

The final target 19 was prepared from 40b (73 mg, 0.095 mmol, 1.0 eq.) and 1M (in tetrahydrofuran) tetrabutylammonium fluoride (0.294 mL, 0.294 mmol., 3.1 eq.) in 5.0 mL of anhydrous tetrahydrofuran according to the procedure described for the preparation of 18 to afford an oil. Purification by flash chromatography (24 g silica column, 100-95% dichloromethane in methanol, gradient elution) provided 26 mg (64%) of a white solid. $^1$HNMR (DMSO-d$_6$) δ 11.38 (s, 1H), 8.74 (s, 1H), 6.04 (d, J=3.7 Hz, 1H), 5.32 (dd, J=5.4, 0.8 Hz, 1H), 5.06 (d, J=5.9 Hz, 1H), 4.67 (t, J=5.8 Hz, 1H), 4.27 (td, J=5.3, 3.7 Hz, 1H), 4.06 (q, J=5.6 Hz, 1H), 3.85 (td, J=5.7, 4.2 Hz, 1H), 3.55 (ddd, J=11.7, 5.6, 4.2 Hz, 1H), 3.42 (dt, J=11.9, 6.0 Hz, 1H), 2.47 (t, J=7.3 Hz, 2H), 1.57 (p, J=7.4 Hz, 2H), 1.27 (d, J=3.0 Hz, 16H), 0.95-0.82 (m, 3H). LCMS m/z 427 (M+H)$^+$. HR-ESIMS m/z calcd for C$_{20}$H$_{34}$N$_4$O$_6$·H, 427.25511, found 427.25519. HPLC purity by Method A: 99% at 254 nm.

iv. N-(2-((2R,3R,4S,5R)-3,4-dihydroxy-5-(hydroxymethyl)tetrahydro-furan-2-yl)-3-oxo-2,3-dihydro-1,2,4-triazin-5-yl)butyramide (20)

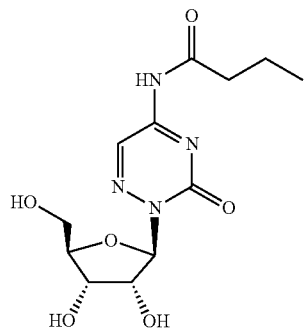 [SMILES: CCCC(=O)Nc1cnn([C@@H]2O[C@H](CO)[C@@H](O)[C@H]2O)c(=O)n1]

(1)N-(2-((2R,3R,4R,5R)-3,4-bis((tert-butyldimethylsilyl)oxy)-5-(((tert-butyldimethylsilyl)oxy)methyl)tetrahydrofuran-2-yl)-3-oxo-2,3-dihydro-1,2,4-triazin-5-yl)butyramide (40c)

Intermediate 40c was prepared from 39 (200 mg, 0.341 mmoles, 1.0 eq) and butanoyl chloride (32 39.9, 0.375 mmoles, 1.1 eq) in 3.0 mL of anhydrous dichloromethane with N,N'-diisopropylethylamine (0.065 mL, 0.375 mmoles, 1.0 eq) as base according to the procedure described for the preparation of 40a to afford a residue. Purification by flash chromatography (40 g silica column, 100-0% hexane in ethyl acetate, gradient elution) provided 152 mg (68%) of a white foamy solid; 1H NMR (400 MHz, cdcl3) δ 8.93 (s, 1H), 8.48 (s, 1H), 6.24 (d, J=4.5 Hz, 1H), 4.52 (t, J=4.5 Hz, 1H), 4.31 (t, J=4.4 Hz, 1H), 4.04 (q, J=4.4 Hz, 1H), 3.80-3.60 (m, 2H), 2.48 (t, J=7.3 Hz, 2H), 1.75 (h, J=7.4 Hz, 2H), 1.01 (t, J=7.4 Hz, 3H), 0.95-0.77 (m, 28H), 0.10 (d, J=2.6 Hz, 18H); LCMS m/z 657 (M+H)+.

(2) Preparation of 20

The final target 20 was prepared from 40c (145 mg, 0.221 mmoles, 1.0 eq) and tetraethylammonium fluoride hydrate (221 mg, 1.32 mmoles, 6 eq) in 7.0 mL of anhydrous tetrahydrofuran for 3 hrs at 60° C. to afford an oil. Purification by flash chromatography (24 g silica column, 100-90% dichloromethane in methanol, gradient elution) provided 41 mg (59%) of a white crystalline solid. 1H NMR (400 MHz, dmso) δ 11.39 (s, 1H), 8.74 (s, 1H), 6.04 (d, J=3.7 Hz, 1H), 5.32 (d, J=5.5 Hz, 1H), 5.07 (d, J=6.0 Hz, 1H), 4.67 (t, J=5.8 Hz, 1H), 4.27 (td, J=5.2, 3.7 Hz, 1H), 4.06 (q, J=5.6 Hz, 1H), 3.85 (td, J=5.6, 4.1 Hz, 1H), 3.60-3.38 (m, 2H), 2.46 (t, J=7.3 Hz, 2H), 1.60 (h, J=7.4 Hz, 2H), 0.92 (t, J=7.4 Hz, 3H); HRMS: calc for $C_{12}H_{18}N_4O_6 \cdot H$, 315.12991, found, 315.1296; HPLC 98.6% at 254 nm.

v. N-(2-((2R,3R,4S,5R)-3,4-dihydroxy-5-(hydroxymethyl)tetrahydro-furan-2-yl)-3-oxo-2,3-dihydro-1,2,4-triazin-5-yl)cyclopropane-carboxamide (21)

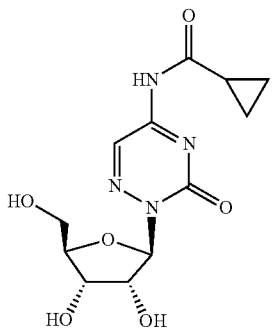 [SMILES: O=C(Nc1cnn([C@@H]2O[C@H](CO)[C@@H](O)[C@H]2O)c(=O)n1)C1CC1]

(1) N-(2-((2R,3R,4R,5R)-3,4-bis((tert-butyldimethylsilyl)oxy)-5-(((tert-butyldimethylsilyl)oxy)methyl)tetrahydrofuran-2-yl)-3-oxo-2,3-dihydro-1,2,4-triazin-5-yl)cyclopropane-carboxamide (40d)

Intermediate 40d was prepared from 39 (200 mg, 0.341 mmoles, 1.0 eq) and cyclopropanecarbonyl chloride (39 mg, 0.375 mmoles, 1.1 eq) in 3.0 mL of anhydrous dichloromethane with N, N'-diisopropylethylamine (0.065 mL, 0.375 mmoles, 1.1 eq) as base according to the procedure described for the preparation of 40a to afford a residue. Purification by flash chromatography (40 g silica column, 100-0% hexane in ethyl acetate, gradient elution) provided 142 mg (64%) of a white foamy solid; LCMS m/z 655 (M+H)+.

(2) Preparation of 21

The final target 21 was prepared from 40d (131 mg, 0.20 mmoles, 1.0 eq) and tetraethylammonium fluoride hydrate (207 mg, 1.24 mmoles, 6.2 eq) in 7.0 mL of anhydrous tetrahydrofuran for 3 hrs at 65° C. to afford an oil. Purification by flash chromatography (24 g silica column, 100-90% dichloromethane in methanol, gradient elution) provided 39 mg (62%) of a white solid. ¹H NMR (400 MHz, dmso) δ 11.76 (s, 1H), 8.75 (s, 1H), 6.04 (d, J=3.6 Hz, 1H), 5.31 (d, J=5.4 Hz, 1H), 5.06 (d, J=6.0 Hz, 1H), 4.67 (t, J=5.8 Hz, 1H), 4.27 (td, J=5.2, 3.6 Hz, 1H), 4.08 (dq, J=18.3, 5.4 Hz, 1H), 3.85 (td, J=5.6, 4.1 Hz, 1H), 3.59-3.37 (m, 2H), 2.16-1.95 (m, 1H), 1.08-0.82 (m, 4H); LCMS m/z 313 (M+H)+; HRMS: calc for $C_{12}H_{16}N_4O_6 \cdot H$, 313.11426, found, 313.11397; HPLC 100% at 254 nm.

vi. Synthesis of N-(2-((2R,3R,4S,5R)-3,4-dihydroxy-5-(hydroxymethyl)-tetrahydrofuran-2-yl)-3-oxo-2,3-dihydro-1,2,4-triazin-5-yl)-cyclobutanecarboxamide (22)

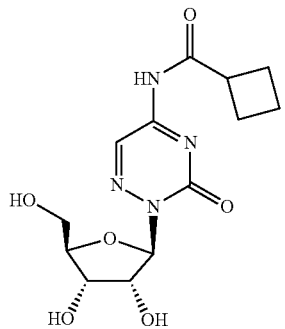 [SMILES: O=C(Nc1cnn([C@@H]2O[C@H](CO)[C@@H](O)[C@H]2O)c(=O)n1)C1CCC1]

(1) N-(2-((2R,3R,4R,5R)-3,4-bis((tert-butyldimethylsilyl)oxy)-5-(((tert-butyldimethylsilyl)oxy)methyl)tetrahydrofuran-2-yl)-3-oxo-2,3-dihydro-1,2,4-triazin-5-yl)cyclobutane-carboxamide (40e)

Intermediate 40e was prepared from 39 (200 mg, 0.341 mmoles, 1.0 eq) and cyclobutanecarbonyl chloride (44 mg, 0.375 mmoles, 1.1 eq) in 3.0 mL of anhydrous dichloromethane with N, N'-diisopropylethylamine (0.065 mL, 0.375 mmoles, 1.1 eq) as base according to the procedure described for the preparation of 40a to afford a residue. Purification by flash chromatography (40 g silica column, 100-0% hexane in ethyl acetate, gradient elution) provided 176 mg (77%) of an off-white foamy solid; ¹H NMR (400 MHz, cdcl3) δ 8.96 (s, 1H), 8.54 (s, 1H), 6.24 (d, J=4.5 Hz, 1H), 4.53 (t, J=4.5 Hz, 1H), 4.31 (t, J=4.4 Hz, 1H), 4.04 (q, J=4.4 Hz, 1H), 3.71 (qd, J=11.2, 4.5 Hz, 2H), 3.43-3.28 (m, 1H), 2.47-2.19 (m, 4H), 2.16-1.84 (m, 2H), 1.05-0.75 (m, 28H), 0.10 (d, J=2.6 Hz, 18H); LCMS m/z 669 (M+H)+.

(2) Preparation of 22

The final target 22 was prepared from 40e (155 mg, 0.23 mmoles, 1.0 eq) and tetraethylammonium fluoride hydrate (232 mg, 1.39 mmoles, 6 eq) in 7.0 mL of anhydrous tetrahydrofuran for 3 hrs at 65° C. to afford a residue. Purification by flash chromatography (24 g silica column, 100-90% dichloromethane in methanol, gradient elution) provided 31 mg (41%) of a white solid. ¹H NMR (400 MHz, dmso) δ 11.27 (s, 1H), 8.77 (s, 1H), 6.04 (d, J=3.7 Hz, 1H), 5.32 (d, J=5.3 Hz, 1H), 5.06 (d, J=6.0 Hz, 1H), 4.68 (t, J=5.8 Hz, 1H), 4.27 (td, J=5.2, 3.6 Hz, 1H), 4.06 (q, J=5.5 Hz, 1H), 3.85 (td, J=5.6, 4.1 Hz, 1H), 3.60-3.37 (m, 3H), 2.32-2.07 (m, 4H), 1.95 (dp, J=11.8, 8.6 Hz, 1H), 1.87-1.74 (m, 1H); LCMS m/z 327 (M+H)+; HRMS: calc for $C_{13}H_{18}N_4O_6$·H, 327.12991, found, 327.1294; HPLC 92.8% at 254 nm.

vii. Synthesis of ethyl (2-((2R,3R,4S,5R)-3,4-dihydroxy-5-(hydroxy-methyl)tetrahydrofuran-2-yl)-3-oxo-2,3-dihydro-1,2,4-triazin-5-yl)carbamate (23)

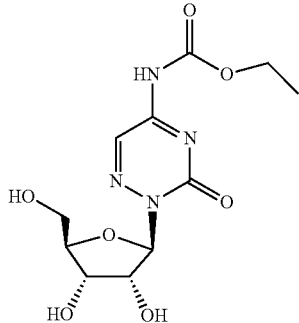 [SMILES: CCOC(=O)Nc1cnn([C@@H]2O[C@H](CO)[C@@H](O)[C@H]2O)c(=O)n1]

(1) ethyl (2-((2R,3R,4R,5R)-3,4-bis((tert-butyldimethylsilyl)oxy)-5-(((tert-butyldimethylsilyl)oxy)methyl)tetrahydrofuran-2-yl)-3-oxo-2,3-dihydro-1,2,4-triazin-5-yl)carbamate (40f)

Intermediate 40f was prepared from 39 (200 mg, 0.341 mmoles, 1.0 eq) and ethyl chloroformate (41 mg, 0.375 mmoles, 1.1 eq) in 3.0 mL of anhydrous dichloromethane with N, N'-diisopropylethylamine (0.059 mL, 0.341 mmoles, 1 eq) as base according to the procedure described for the preparation of 40a to afford a residue. Purification by flash chromatography (40 g silica column, 100-0% hexane in ethyl acetate, gradient elution) provided 117 mg (52%) of white solid; $^1$H NMR (400 MHz, cdcl3) δ 8.79 (s, 1H), 7.59 (s, 1H), 6.24 (d, J=4.6 Hz, 1H), 4.53 (t, J=4.6 Hz, 1H), 4.37-4.25 (m, 3H), 4.04 (q, J=4.4 Hz, 1H), 3.71 (qd, J=11.2, 4.5 Hz, 2H), 1.36 (t, J=7.1 Hz, 3H), 1.02-0.77 (m, 27H), 0.10 (d, J=2.4 Hz, 18H); LCMS m/z 659 (M+H)+.

(2) Preparation of 23

The final target 23 was prepared from 40f (104 mg, 0.16 mmoles, 1.0 eq) and tetraethylammonium fluoride hydrate (121 mg, 0.73 mmoles, 4.6 eq) in 5.0 mL of anhydrous tetrahydrofuran for 3 hrs at 65° C. to afford a residue. Purification by flash chromatography (24 g silica column, 100-90% dichloromethane in methanol, gradient elution) provided 31 mg (62%) of a white crystalline solid. $^1$H NMR (400 MHz, dmso) δ 11.31 (s, 1H), 8.58 (s, 1H), 6.03 (d, J=3.7 Hz, 1H), 5.31 (d, J=5.4 Hz, 1H), 5.05 (d, J=6.0 Hz, 1H), 4.68 (t, J=5.8 Hz, 1H), 4.34-4.15 (m, 3H), 4.05 (q, J=5.5 Hz, 1H), 3.85 (td, J=5.7, 4.2 Hz, 1H), 3.60-3.37 (m, 2H), 1.27 (t, J=7.1 Hz, 3H); LCMS m/z 339 (M+Na)+; HRMS: calc for $C_{11}H_{16}N_4O_7$·H, 317.10981, found, 317.10918; HPLC 96.6% at 254 nm.

viii. Synthesis of pentyl (2-((2R,3R,4S,5R)-3,4-dihydroxy-5-(hydroxy-methyl)tetrahydrofuran-2-yl)-3-oxo-2,3-dihydro-1,2,4-triazin-5-yl)carbamate (24)

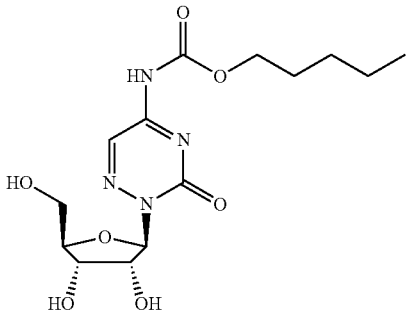 [SMILES: CCCCCOC(=O)Nc1cnn([C@@H]2O[C@H](CO)[C@@H](O)[C@H]2O)c(=O)n1]

(1) pentyl (2-((2R,3R,4R,5R)-3,4-bis((tert-butyldimethylsilyl)oxy)-5-(((tert-butyldimethylsilyl)oxy)methyl)tetrahydrofuran-2-yl)-3-oxo-2,3-dihydro-1,2,4-triazin-5-yl)carbamate (40 g)

Intermediate 40 g was prepared from 39 (200 mg, 0.341 mmoles, 1.0 eq) and pentyl chloridocarbonate (56 mg, 0.375 mmoles, 1.1 eq) in 3.0 mL of anhydrous dichloromethane with N, N'-diisopropylethylamine (0.065 mL, 0.375 mmoles, 1 eq) as base according to the procedure described for the preparation of 40a to afford a residue. Purification by flash chromatography (40 g silica column, 100-0% hexane in ethyl acetate, gradient elution) provided 129 mg (54%) of white crystalline solid; $^1$H NMR (400 MHz, cdcl3) δ 8.79 (s, 1H), 7.57 (s, 1H), 6.24 (d, J=4.5 Hz, 1H), 4.53 (t, J=4.6 Hz, 1H), 4.30 (t, J=4.3 Hz, 1H), 4.24 (t, J=6.7 Hz, 2H), 4.04 (q, J=4.5 Hz, 1H), 3.80-3.58 (m, 2H), 1.77-1.66 (m, 2H), 1.37 (h, J=3.9 Hz, 4H), 1.00-0.79 (m, 27H), 0.10 (d, J=2.3 Hz, 18H); LCMS m/z 701 (M+H)+.

(2) Preparation of 24

The final target 24 was prepared from 40 g (115 mg, 0.164 mmoles, 1.0 eq) and 1M (in tetrahydrofuran) tetrabutylammonium fluoride (0.509 mL, 0.509 mmoles, 3.1 eq) in 7.0 mL of anhydrous tetrahydrofuran according to the procedure described for the preparation of 18 to afford residue. Purification by flash chromatography (24 g silica column, 100-95% dichloromethane in methanol, gradient elution) provided 39 mg (66%) of a white solid. $^1$H NMR (400 MHz, dmso) δ 11.28 (brs, 1H), 8.57 (s, 1H), 6.03 (d, J=3.7 Hz, 1H), 5.31 (d, J=5.4 Hz, 1H), 5.05 (d, J=6.0 Hz, 1H), 4.67 (t, J=5.8 Hz, 1H), 4.27 (td, J=5.2, 3.7 Hz, 1H), 4.17 (t, J=6.7 Hz, 2H), 4.05 (q, J=5.6 Hz, 1H), 3.85 (td, J=5.6, 4.1 Hz, 1H), 3.59-3.38 (m, 2H), 1.65 (dd, J=9.5, 4.5 Hz, 2H), 1.41-1.27 (m, 4H), 0.97-0.82 (m, 3H); HRMS: calc for $C_{14}H_{22}N_4O_7$·H, 359.15613, found, 359.15647; HPLC 99.4% at 254 nm.

119 i. Synthesis of ((2r,3s,4r,5r)-5-(5-amino-3-oxo-1,2,4-triazin-2(3H)-yl)-3,4-dihydroxytetrahydrofuran-2-yl)methyl L-isoleucinate (25)

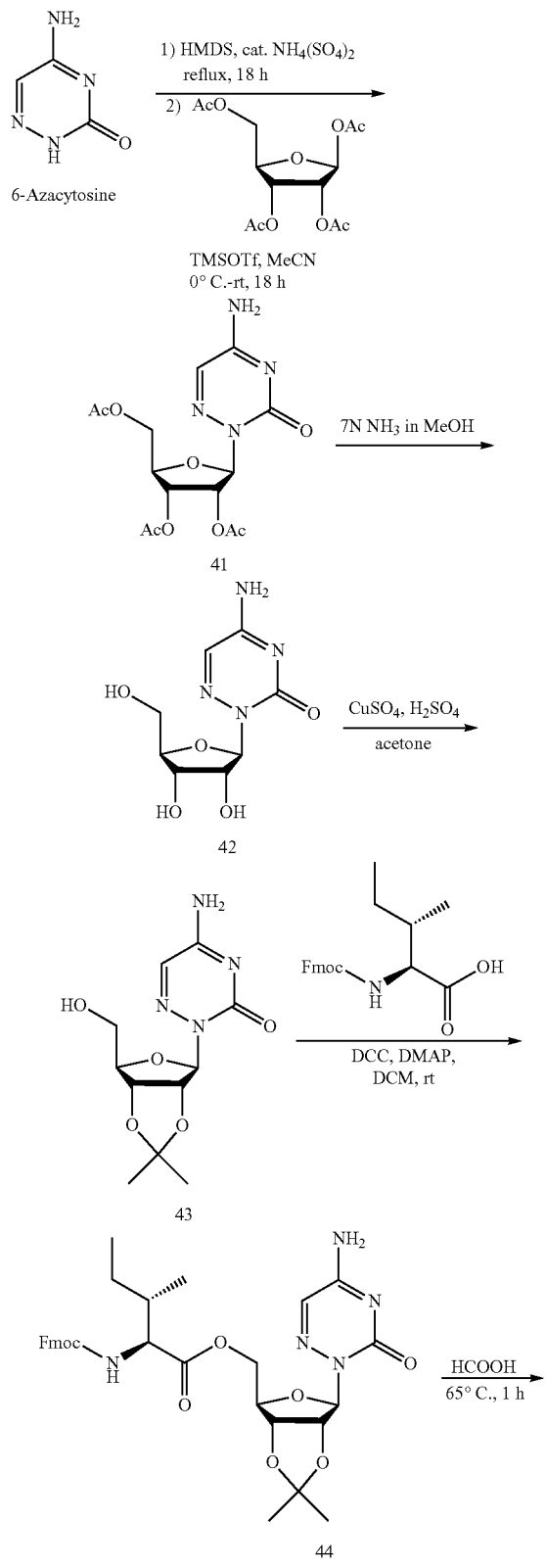

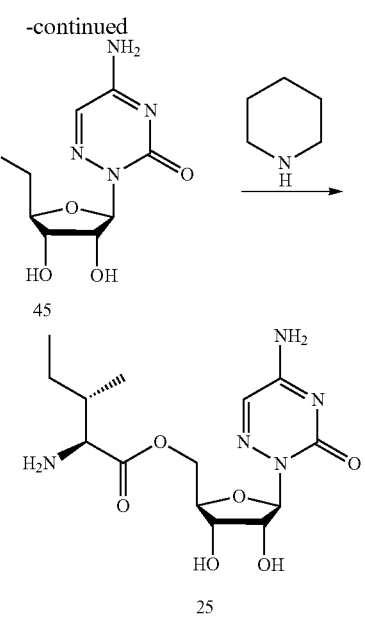

i. Preparation of (2r,3r,4r,5r)-2-(acetoxymethyl)-5-(5-amino-3-oxo-1,2,4-triazin-2(3H)-yl)tetrahydrofuran-3,4-diyl diacetate (41)

6-Azacytosine (1.5 g, 13.38 mmol, 1.0 eq.) was charged in a dry flask and HMDS (100 mL) was added under argon atmosphere. After adding catalytic amount of ammonium sulfate (300 mg, 2.63 mmol, 0.2 eq.), the mixture was refluxed for 6 h under argon. The mixture turned clear and the HMDS was then evaporated carefully on the rotavap under vacuum. The system was vented to argon which reduced introduction of any moisture and resulted in a brown solid mass. The resulted silylated 6-azacytosine and commercial [(3R,4R)-3,4,5-triacetoxytetrahydrofuran-2-yl] methyl acetate (5.1 g, 16.06 mmol, 1.2 eq.) were dissolved in anhydrous acetonitrile (100 mL) under argon and cooled to 0° C. Tin(IV) chloride (1.05 g, 4.7 mL, 40.15 mmol) was carefully added and cooled mixture and reaction mixture was further stirred overnight at room temperature. The mixture was carefully quenched into saturated aqueous $NaHCO_3$ (500 mL) and saturated aqueous $Na_2CO_3$ (200 mL) at 0° C. The mixture was extracted with dichloromethane (4×250 mL) and organic extracts were combined. The combined organic layer was washed with water (200 mL) and brine (100 mL). The organic layer was dried over sodium sulfate and concentrated under vacuum. The crude product was purified by column chromatography (0-30% methanol in dichloromethane) to afford desired isomer 41 (1.2 g, 24.2% yield) as a brown solid. $^1$HNMR (DMSO-$d_6$) δ 8.17 (s, 1H), 8.02 (s, 1H), 7.54 (d, J=1.3 Hz, 1H), 6.14 (dd, J=3.7, 1.3 Hz, 1H), 5.50 (ddd, J=5.1, 3.6, 1.3 Hz, 1H), 5.32 (td, J=5.9, 1.4 Hz, 1H), 4.30 (ddd, J=12.0, 3.6, 1.4 Hz, 1H), 4.23 (td, J=5.9, 4.5 Hz, 1H), 4.02 (ddd, J=11.9, 5.2, 1.4 Hz, 1H), 2.11-1.91 (m, 9H).

ii. Preparation of 5-amino-2-((2r,3r,4s,5r)-3,4-dihydroxy-5-(hydroxymethyl)tetrahydrofuran-2-yl)-1,2,4-triazin-3(2H)-one (6-azacytidine) (42)

Intermediate 41 (1.15 g, 3.11 mmol, 1.0 eq.) was taken in 7N ammonia solution in methanol (15 mL, 105 mmol, 33 eq.) and heated at 80° C. in a steel pressure vessel for 18 h. The TLC showed all starting material being consumed. The mixture was concentrated to yield the crude residue. Recrystallization of the residue from ethanol afforded 42 (510 mg, 2.08 mmol, 67% yield) as a light orange solid. $^1$H NMR (DMSO-d$_6$) δ 7.97 (s, 1H), 7.86 (s, 1H), 7.48 (s, 1H), 5.95 (d, J=4.0 Hz, 1H), 5.15 (d, J=5.3 Hz, 1H), 4.94 (d, J=5.8 Hz, 1H), 4.64 (t, J=5.8 Hz, 1H), 4.18 (q, J=4.8 Hz, 1H), 3.95 (q, J=5.3 Hz, 1H), 3.74 (td, J=5.6, 4.3 Hz, 1H), 3.48 (ddd, J=11.9, 5.5, 4.3 Hz, 1H), 3.35 (dt, J=11.4, 5.9 Hz, 1H).

iii. Preparation of 5-amino-2-((3ar,4r,6r,6ar)-6-(hydroxymethyl)-2,2-dimethyltetrahydrofuro[3,4-d][1,3]dioxol-4-yl)-1,2,4-triazin-3(2H)-one (43)

To a solution of 42 (150 mg, 0.61 mmol, 1.0 eq.) and copper sulfate (500 mg, 3.13 mmol, 5.0 eq.) in 125 mL of anhydrous acetone was added 0.13 mL of concentrated sulfuric acid, and the mixture was stirred under argon at room temperature for 3 days. The mixture was filtered and the filtrate was neutralized slowly to pH 7 by addition of 1.8 mL cold 7N ammonia in methanol. Solvent was removed by evaporation under vacuum. Crude residue was purified on silica gel (0-30% methanol in dichloromethane) to afford 43 (65 mg, 37% yield) as a white solid. $^1$H NMR (DMSO-d$_6$) δ 8.07 (s, 1H), 7.93 (s, 1H), 7.47 (d, J=0.5 Hz, 1H), 6.09 (d, J=1.6 Hz, 1H), 4.97 (dd, J=6.2, 1.7 Hz, 1H), 4.81 (t, J=5.8 Hz, 1H), 4.74-4.65 (m, 1H), 3.98 (td, J=6.7, 2.9 Hz, 1H), 3.39 (ddd, J=6.5, 5.9, 2.8 Hz, 2H), 1.51-1.39 (m, 3H), 1.27 (d, J=0.7 Hz, 3H).

iv. Preparation of ((3ar,4r,6r,6ar)-6-(5-amino-3-oxo-1,2,4-triazin-2(3H)-yl)-2,2-dimethyltetrahydrofuro[3,4-d][1,3]dioxol-4-yl)methyl-(((9H-fluoren-9-yl)methoxy)carbonyl)-L-isoleucinate (44)

Intermediate 43 (90 mg, 0.32 mmol, 1.0 eq.) was dissolved in anhydrous dichloromethane (5 mL) and added (2S,3S)-2-(9H-fluoren-9-ylmethoxycarbonylamino)-3-methyl-pentanoic acid 32b (168 mg, 0.47 mmol, 1.5 eq.) followed by N-(3-dimethylaminopropyl)-N-ethylcarbodiimide hydrochloride (103 mg, 0.54 mmol, 1.7 eq.) at room temperature. The reaction mixture was stirred at room temperature for 18 h. The mixture was concentrated, redissolved in ethyl acetate (50 mL) and washed with saturated aqueous sodium bicarbonate (10 mL) and brine (10 mL). The combined aqueous layer was again extracted with ethyl acetate (2×25 mL). The combined organic layer was dried over sodium sulfate and concentrated under vacuum. The crude product was purified by column chromatography (0-100% ethyl acetate in dichloromethane) to afford 44 (70 mg, 35.7% yield) as an off-white solid. $^1$H NMR (DMSO-d$_6$) δ 8.10 (s, 1H), 7.95 (s, 1H), 7.87 (d, J=7.5 Hz, 2H), 7.78-7.66 (m, 3H), 7.47 (s, 1H), 7.40 (t, J=7.5 Hz, 2H), 7.34-7.26 (m, 2H), 6.11 (s, 1H), 5.02 (d, J=6.1 Hz, 1H), 4.76 (dd, J=6.1, 2.5 Hz, 1H), 4.29-4.09 (m, 6H), 4.06-3.92 (m, 1H), 1.76 (s, 1H), 1.44 (s, 3H), 1.25 (s, 3H), 1.16 (td, J=7.1, 0.8 Hz, 1H), 0.78 (t, J=7.7 Hz, 6H).

v. Preparation of ((2r,3s,4r,5r)-5-(5-amino-3-oxo-1,2,4-triazin-2(3H)-yl)-3,4-dihydroxytetrahydrofuran-2-yl)methyl (((9H-fluoren-9-yl)methoxy)carbonyl)-L-isoleucinate (45)

Intermediate 45 was synthesized from 44 (60 mg, 0.1 mmol) and formic acid (2 mL, 50% solution v/v in water) using the same procedure as for 34a to afford. 45 (24 mg, 42% yield) as a white solid. $^1$H NMR (DMSO-d$_6$) δ 8.00 (s, 1H), 7.94-7.82 (m, 3H), 7.72 (t, J=6.6 Hz, 3H), 7.47 (s, 1H), 7.39 (d, J=7.5 Hz, 2H), 7.31 (dt, J=8.8, 4.5 Hz, 2H), 6.00 (d, J=3.4 Hz, 1H), 4.36-4.11 (m, 6H), 4.07-3.89 (m, 4H), 1.79 (s, 1H), 1.36 (d, J=11.8 Hz, 1H), 1.20 (d, J=12.9 Hz, 2H), 0.89-0.73 (m, 6H).

vi. Preparation of ((2r,3s,4r,5r)-5-(5-amino-3-oxo-1,2,4-triazin-2(3H)-yl)-3,4-dihydroxytetrahydrofuran-2-yl)methyl L-isoleucinate (25)

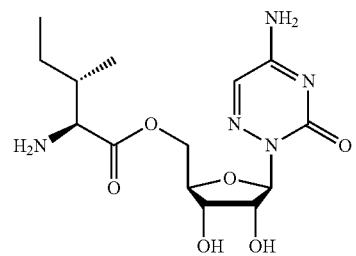

Final target 25 was prepared from 45 (16 mg, 0.03 mmol) and piperidine (1 mL of 3% v/v solution in DMF) using a similar procedure as for 9, to afford 25 (7.2 mg, 72% yield) as hygroscopic solid. $^1$HNMR (DMSO-d6) δ 8.00 (s, 1H), 7.89 (s, 1H), 7.46 (s, 1H), 5.99 (d, J=3.4 Hz, 1H), 5.30 (d, J=5.1 Hz, 1H), 5.12 (d, J=6.0 Hz, 1H), 4.26-4.14 (m, 2H), 4.09-3.81 (m, 3H), 3.12 (d, J=5.4 Hz, 1H), 1.56 (ddt, J=9.6, 6.9, 5.0 Hz, 1H), 1.35 (ddt, J=14.9, 7.5, 3.8 Hz, 1H), 1.07 (ddt, J=14.2, 8.8, 7.3 Hz, 1H), 0.79 (dd, J=8.4, 7.0 Hz, 6H). $^{11}$C NMR (DMSO-d6) δ 175.60, 159.11, 153.53, 128.09, 90.68, 81.09, 79.74, 79.61, 79.41, 79.08, 73.07, 71.02, 64.44, 59.12, 40.59, 40.39, 40.18, 39.97, 39.76, 39.55, 39.34, 24.58, 16.10, 11.85. HRMS m/z calcd. for [M+H]$^+$ $C_{14}H_{24}N_5O_6$ 358.1721, found 358.1719. HPLC purity by Method A: 92% at 254 nm 2. Characterization of Antiviral Agents A list of compounds evaluated for antiviral activity is shown in Table 1 below.

TABLE 1

| No. | Structure |
| --- | --- |
| 1 | 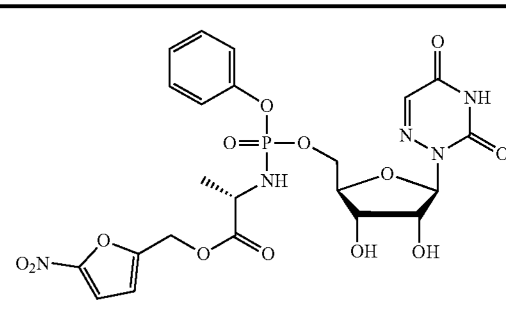 |

TABLE 1-continued

| No. | Structure |
|---|---|
| 2 | 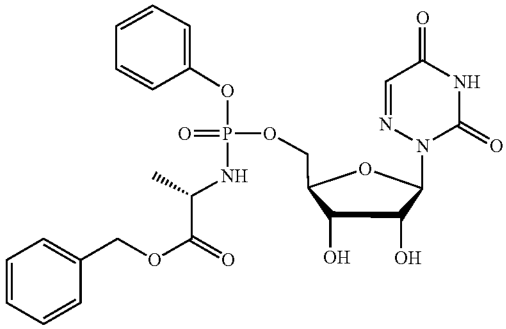 |
| 3 | 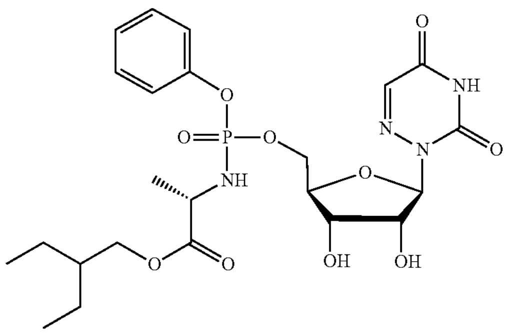 |
| 4 | 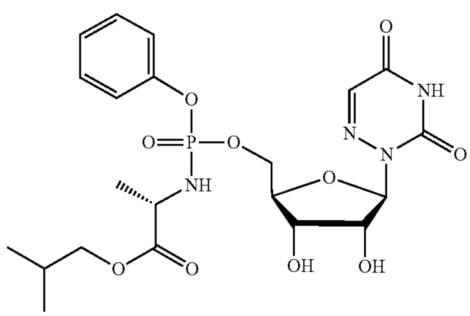 |
| 5 | 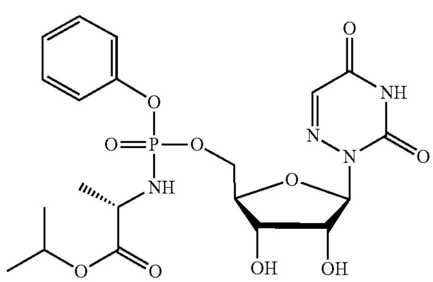 |
| 6 | 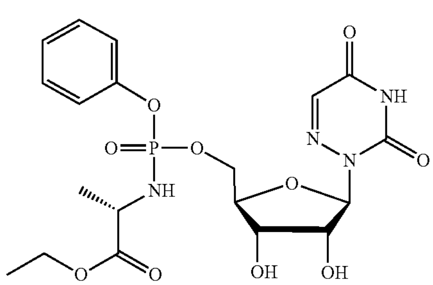 |
| 7 | |
| 8 | |
| 9 | |
| 10 | |
| 11 | |

TABLE 1-continued

| No. | Structure |
|-----|-----------|
| 12 | 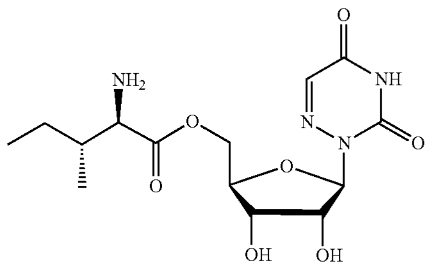 |
| 13 | 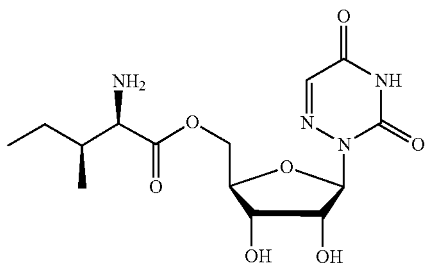 |
| 14 | 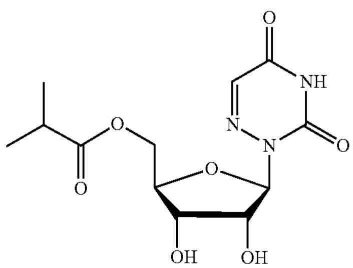 |
| 15 | 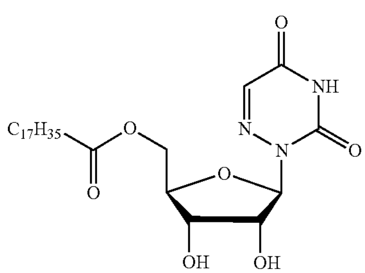 |
| 16 | 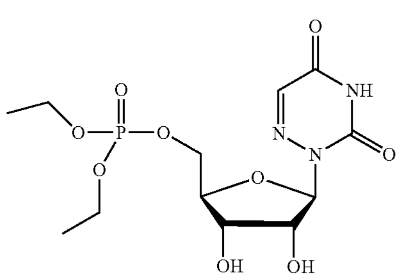 |
| 17 | |
| 18 | |
| 19 | |
| 20 | |

TABLE 1-continued

| No. | Structure |
|---|---|
| 21 | 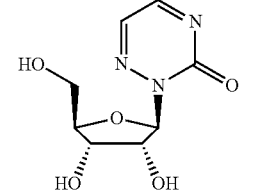 |
| 22 | 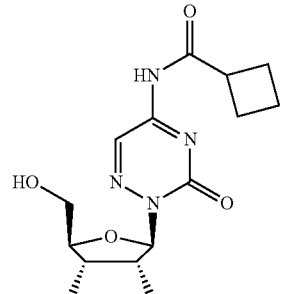 |
| 23 | 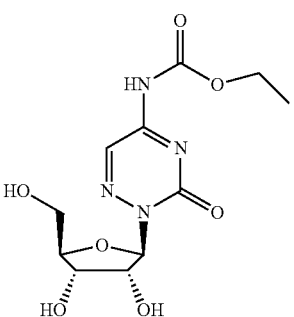 [SMILES: CCOC(=O)Nc1cnn([C@@H]2O[C@H](CO)[C@@H](O)[C@H]2O)c(=O)n1] |
| 24 | 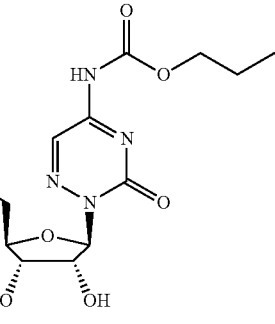 |
| 25 | 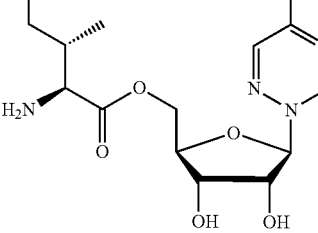 |

The antiviral activity against Alpharviruses evaluated in HEK293 cells (4 hours pre-incubation with compound before infected with virus) is shown in Table 2 below. VTR=Virus titer reduction in log at 10 μM concentration. NT: not tested, ND: not determined

TABLE 2

| No. | WNV (HEK293 cells) | | | DENV (HEK293 cells) | | ZIKA (HEK 293 cells) | |
|---|---|---|---|---|---|---|---|
|  | EC$_{90}$ (μM) | CC$_{50}$ (μM) | VTR | EC$_{90}$ (μM) | VTR | EC$_{90}$ (μM) | VTR |
| 1 | 0.6 | 40 | 3.8 | 1.9 | 2.4 | 3.2 | 2.2 |
| 2 | 1.3 | >40 | 3.0 | 6.9 | 1.3 | 16 | ND |
| 3 | 2.9 | >40 | 3.2 | 2.5 | 3.5 | 3.3 | 2.4 |
| 4 | 1.2 | 40 | 3.1 | 2.0 | 2.2 | 4.8 | 2.0 |
| 5 | >30 | ND | ND | >30 | ND | >30 | ND |
| 6 | 10 | >40 | ND | >15 | ND | 12 | ND |
| 7 | 4.3 | 40 | 2.6 | 5 | 3.2 | 7.6 | 1.3 |
| 8 | 2.9 | >40 | 2.8 | 3.9 | 2.3 | 6 | 1.6 |
| 9 | 0.22 | 29 | 3.5 | 1.3 | 3.2 | 1.4 | 2 |
| 10 | 0.2 | 29 | 3.9 | 0.3 | 3.4 | 0.5 | 3.1 |
| 11 | >30 | ND | ND | >30 | ND | >30 | ND |
| 12 | NT | 6.2 | NT | 0.5 | 3.9 | NT | NT |
| 13 | NT | 6.7 | NT | 0.5 | 4 | NT | NT |
| 14 | NT | >40 | NT | 5 | 2.1 | NT | NT |
| 15 | 0.33 | 0.97 | 4.5 | 0.16 | 3.6 | 0.4 | 3 |
| 16 | >10 | >40 | ND | >30 | ND | >10 | ND |
| 17 | NT | NT | NT | >30 | ND | NT | NT |
| 18 | 0.40 | 30.8 | 2.8 | 0.20 | 4.0 | 0.10 | 2.7 |
| 19 | 0.7 | >40 | 4 | 0.60 | 2.1 | 1.1 | 2.6 |
| 20 | NT | 22.9 | NT | 1.2 | 3 | 0.2 | 2.8 |
| 21 | 0.4 | 18.9 | 4.5 | 0.34 | 3.4 | 0.2 | 4 |
| 22 | NT | 6.46 | NT | 1 | 3.2 | 0.4 | 2.6 |
| 23 | NT | 22.4 | NT | 1.3 | 3.3 | 0.3 | 3 |
| 24 | NT | 20.4 | NT | 1.2 | 3.3 | 0.3 | 3.1 |
| 25 | NT | >40 | NT | 5.1 | 2 | NT | NT |

The antiviral activity against Alphaviruses evaluated in NHDF cells (4 hours pre-incubation with compound) is shown in Table 3 below. VTR=Virus titer reduction in log at 10 μM concentration. NT: not tested, ND: not determined.

TABLE 3

| No. | CHIKV (NHDF cells) | | | VEEV (NHDF cells) | |
|---|---|---|---|---|---|
|  | EC$_{90}$ (μM) | CC$_{50}$ (μM) | VTR | EC$_{90}$ (μM) | VTR |
| 1 | 0.95 | >40 | 4.3 | >10 | 0.85 |
| 2 | 0.4 | >40 | 0 | >10 | 0 |
| 3 | >10 | >40 | 0 | >10 | 0 |
| 4 | >10 | >40 | 0 | 8.9 | 1.18 |
| 5 | >10 | >40 | 0.15 | >10 | 0 |
| 6 | >10 | >40 | 0 | >10 | 0 |
| 7 | >10 | >40 | 0 | >10 | 0 |
| 8 | >10 | >40 | 0 | >10 | 0.21 |
| 9 | 1 | >40 | 1.34 | 3.04 | 3.1 |
| 10 | >10 | >40 | 0.39 | 0.62 | 3.51 |
| 11 | >10 | >40 | 0.05 | NT | NT |
| 12 | 0.89 | >40 | 4.55 | NT | NT |
| 13 | 0.51 | >40 | 4.3 | NT | NT |
| 14 | NT | NT | NT | NT | NT |
| 15 | 0.31 | 7.96 | 2.6 | >10 | 0 |
| 16 | NT | NT | NT | 10.1 | 1.05 |
| 17 | NT | NT | NT | 5 | 1 |
| 18 | 3.2 | >40 | 1.42 | >10 | 0.13 |
| 19 | NT | NT | NT | NT | NT |
| 20 | 9 | ND | 1.5 | NT | NT |
| 21 | 4.9 | ND | 1.7 | NT | NT |
| 22 | 8 | ND | 0.89 | NT | NT |
| 23 | >10 | ND | 0 | NT | NT |
| 24 | >10 | ND | 0 | NT | NT |
| 25 | 0.85 | >40 | 2.58 | 1.5 | 2.17 |

The antiviral activity against Influenza viruses (H1N1 and H3N2 strains) evaluated in MDCK cells (4-6 hours pre-incubation with compound) shown in Table 5 below.

VTR=Virus titer reduction in log at 20 μM concentration.
NT: not tested, ND: not determined.

TABLE 4

| | H1N1 strain (MDCK cells) | | | H3N2 strain (MDCK cells) | |
|---|---|---|---|---|---|
| | EC$_{90}$ (μM) | CC$_{50}$ (μM) | VTR | EC$_{90}$ (μM) | VTR |
| 1 | ND | >100 | 1.6 | ND | 0.6 |
| 2 | ND | >100 | 2.3 | ND | 0.9 |
| 3 | NT | NT | NT | NT | NT |
| 4 | ND | >100 | 3.4 | ND | 1.3 |
| 5 | ND | >100 | 0.2 | ND | −0.1 |
| 6 | ND | >100 | 1.6 | ND | 0.2 |
| 7 | ND | >100 | 3.4 | ND | 1.6 |
| 8 | ND | >100 | 3.4 | ND | 1.6 |
| 9 | 0.77 | 19.6 | 3.4 | 2.41 | 3.4 |
| 10 | 3.68 | 19.3 | 3.4 | 3.33 | 3.4 |
| 11 | 0.14 | >20 | 3.4 | 0.78 | 3.4 |
| 12 | NT | NT | NT | NT | NT |
| 13 | ND | ND | 3.6 | ND | 2.8 |
| 14 | 3.6 | >20 | 3.3 | 16.44 | 3.3 |
| 15 | 0.75 | >20 | 3.3 | 3.29 | 3.0 |
| 16 | >100 | >100 | ND | NT | NT |
| 17 | NT | NT | NT | NT | NT |
| 18 | 0.66 | 19.6 | 3.3 | 2.78 | 3.4 |
| 19 | 3.16 | >20 | 3.3 | 12.1 | 3.3 |
| 20 | 2.8 | >20 | 2.9 | 3.5 | 2.7 |
| 21 | 2.8 | >20 | 3.6 | 3.9 | 3 |
| 22 | 0.68 | 19 | 2.9 | 3.9 | 3 |
| 23 | 3.78 | >20 | 3.6 | 6.3 | 2 |
| 24 | NT | NT | 2.9 | NT | 1.6 |
| 25 | NT | NT | NT | NT | NT |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

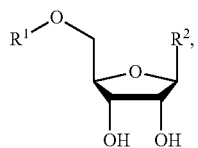

wherein $R^1$ is selected from —C(O)$R^{10}$, —C(O)CH($R^{11}$)NH$_2$, and —P(O)(OAr$^1$)NHCH($R^{12}$)CO$_2R^{13}$;
wherein $R^{10}$, when present, is selected from C1-C20 alkyl and C2-C20 alkenyl;
wherein $R^{11}$, when present, is a side chain of an amino acid selected from arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan;
wherein $R^{12}$, when present, is selected from C1-C6 alkyl and C3-C6 cycloalkyl;
wherein $R^{13}$, when present, is selected from C1-C8 alkyl, C3-C8 cycloalkyl, Ar$^2$, and —CH$_2$Ar$^2$;
wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
wherein each of $R^{14a}$ and $R^{14b}$, when present, is independently C1-C8 alkyl; and
wherein Ar$^1$, when present, is selected from C6-C14 aryl and C2-C10 heteroaryl, and is substituted with 0, 1, 2, or 3 groups independently selected from halog'en, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and
wherein $R^2$ is a structure represented by a formula selected from:

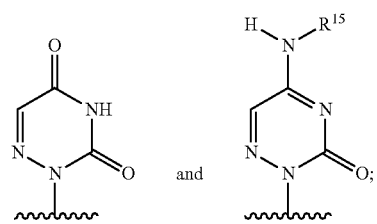

and
wherein $R^{15}$, when present, is selected from hydrogen, —C(O)(C1-C20 alkyl), —C(O)(C3-C6 cycloalkyl), and —C(O)(C2-C20 alkenyl),
provided that when $R^2$ is

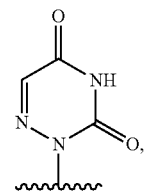 [SMILES: *n1ncc(=O)[nH]c1=O]

then $R^1$ is —C(O)CH($R^{11}$)NH$_2$ or —P(O)(OAr$^1$)NHCH($R^{12}$)CO$^2R^{13}$,
or a pharmaceutically acceptable salt thereof.

2. The compound of claim 1, wherein $R^1$ is —P(O)(OAr$^1$)NHCH($R^{12}$)CO$_2R^{13}$.

3. The compound of claim 1, wherein $R^1$ is —C(O)CH($R^{11}$)NH$_2$.

4. The compound of claim 1, wherein $R^2$ is a structure represented by a formula:

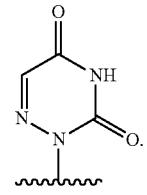 [SMILES: *n1ncc(=O)[nH]c1=O]

5. The compound of claim 4, wherein the compound has a structure represented by a formula selected from:
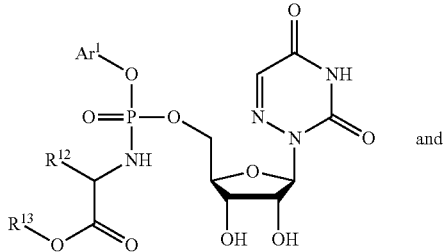
and
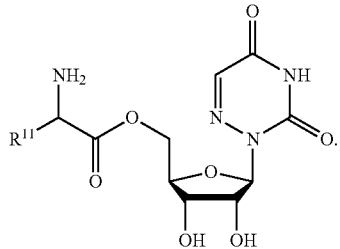
6. The compound of claim 4, wherein the compound is selected from:
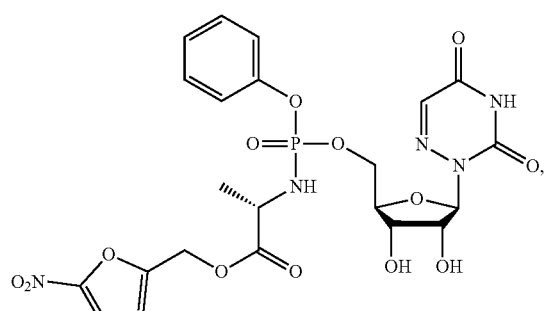
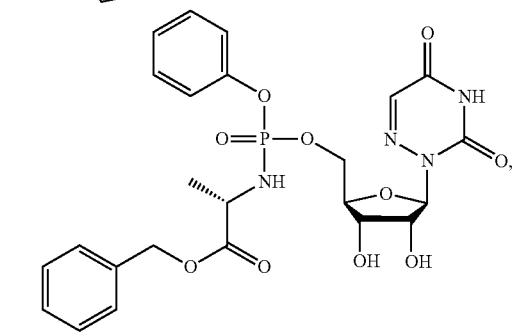
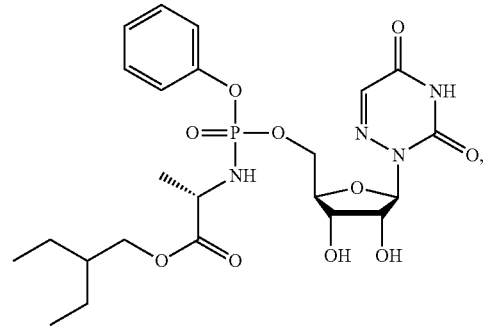
-continued
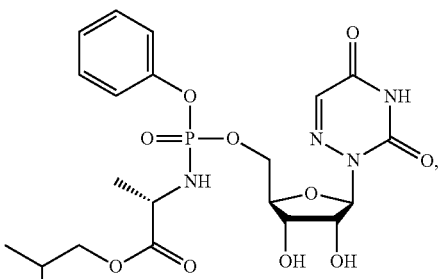
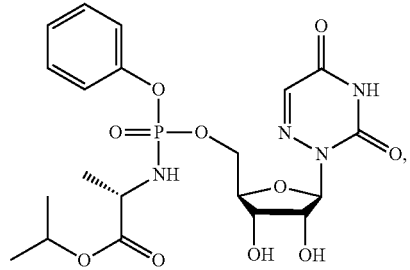
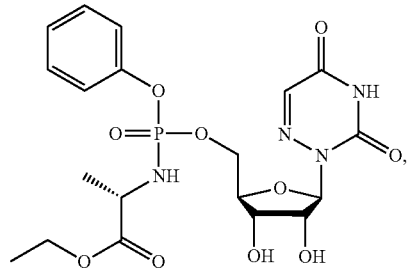
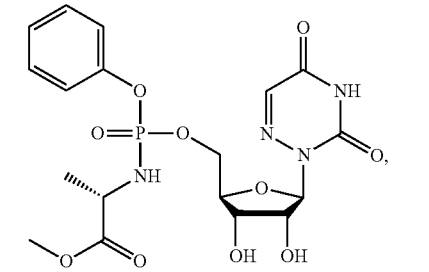
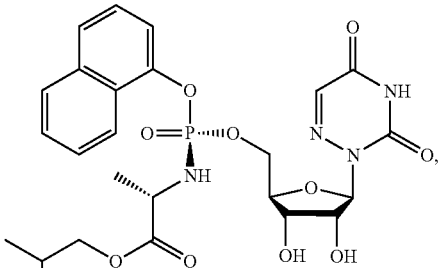
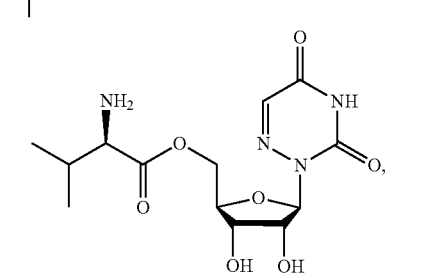

-continued
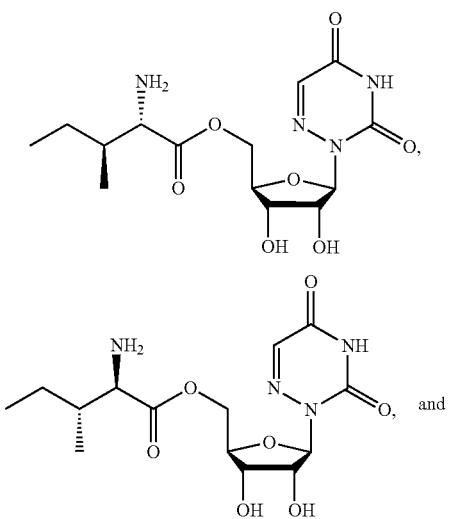
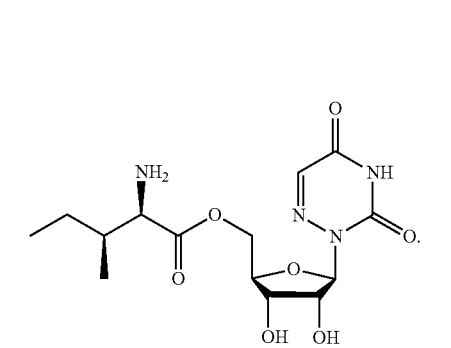
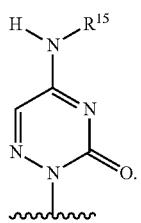
7. The compound of claim 1, wherein $R^2$ is a structure represented by a formula:
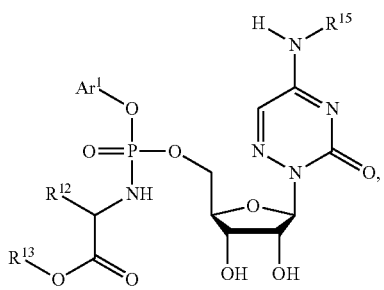
8. The compound of claim 7, wherein the compound has a structure represented by a formula selected from:
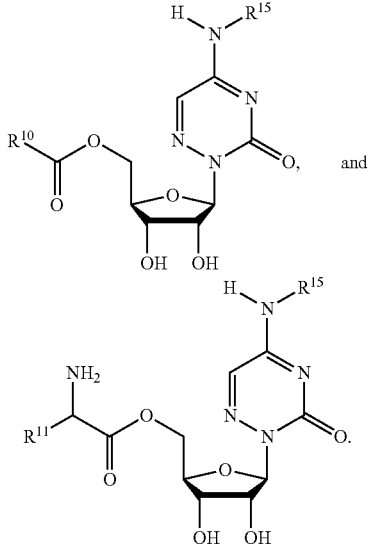
-continued
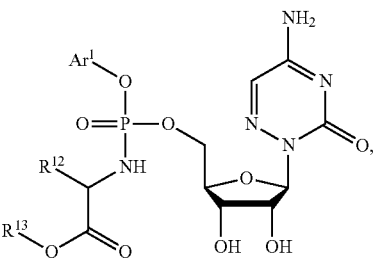
9. The compound of claim 7, wherein the compound has a structure represented by a formula selected from:
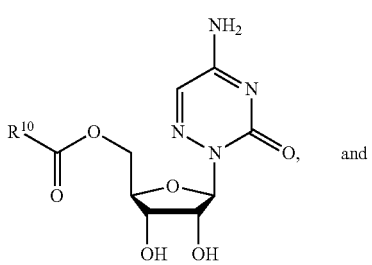
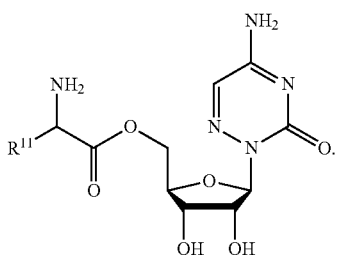

10. The compound of claim 7, wherein the compound is selected from:
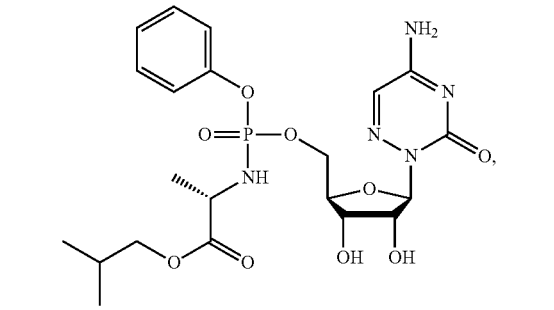
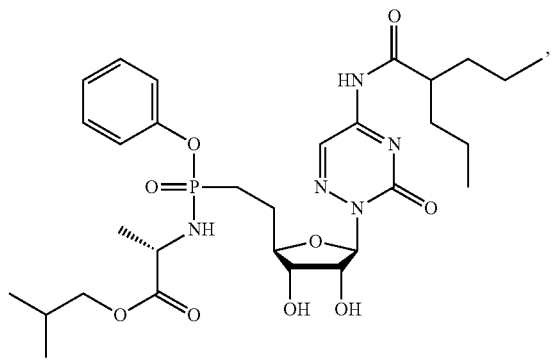
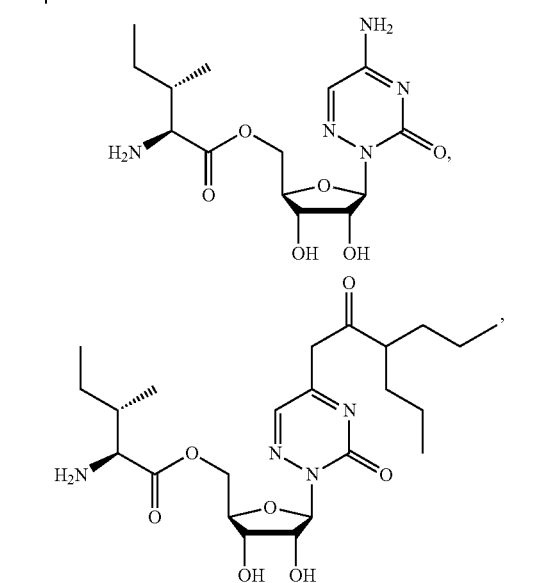
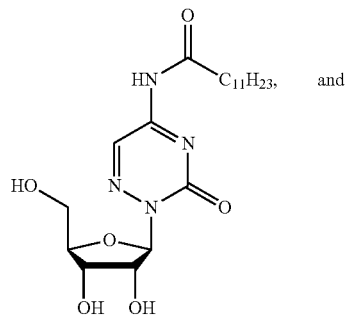
and
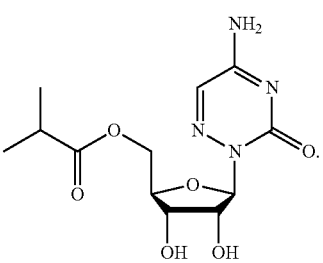
11. The compound of claim 1, wherein $R^{11}$ is selected from:
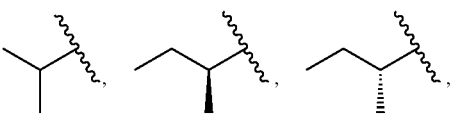
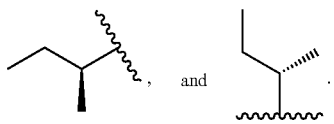
and
12. A compound having a structure represented by a formula:
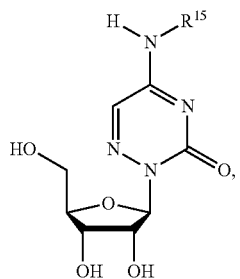
wherein $R^{15}$, when present, is selected from hydrogen, —C(O)(C1-C20 alkyl), —C(O)(C3-C6 cycloalkyl), and —C(O)(C2-C20 alkenyl).

13. A pharmaceutical composition comprising a therapeutically effective amount of compound having a structure represented by a formula:

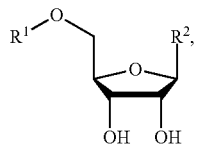

wherein $R^1$ is selected from hydrogen, —C(O)$R^{10}$, —C(O)CH($R^{11}$)NH$_2$, —P(O)(OAr$^1$)NHCH($R^{12}$)CO$_2R^{13}$, and —P(O)(O$R^{14a}$)(O$R^{14b}$);

wherein $R^{10}$, when present, is selected from C1-C20 alkyl and C2-C20 alkenyl;

wherein $R^{11}$, when present, is a side chain of an amino acid selected from arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan;

wherein $R^{12}$, when present, is selected from C1-C6 alkyl and C3-C6 cycloalkyl;

wherein $R^{13}$, when present, is selected from C1-C8 alkyl, C3-C8 cycloalkyl, Ar$^2$, and —CH$_2$Ar$^2$;

wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{14a}$ and $R^{14b}$, when present, is independently C1-C8 alkyl; and wherein Ar$^1$, when present, is selected from C6-C14 aryl and C2-C10 heteroaryl, and is substituted with 0, 1, 2, or 3 groups independently selected from halog'en, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

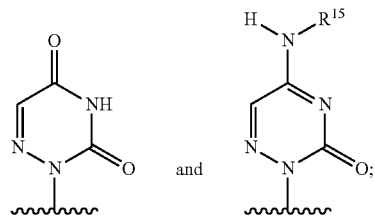

and wherein $R^{15}$, when present, is selected from hydrogen, —C(O)(C1-C20 alkyl), —C(O)(C3-C6 cycloalkyl), and —C(O)(C2-C20 alkenyl), provided that when $R^2$ is

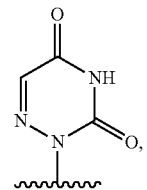

then $R^1$ is —C(O)CH($R^{11}$)NH$_2$, —P(O)(OAr$^1$)NHCH($R^{12}$)CO$_2R^{13}$, or —P(O)(O$R^{14a}$)(O$R^{14b}$), and provided that when IV is hydrogen, then $R^{15}$ is —C(O)(C1-C20 alkyl), —C(O)(C3-C6 cycloalkyl), or —C(O)(C2-C20 alkenyl), or a pharmaceutically acceptable salt thereof, and a pharmaceutically acceptable carrier.

14. A method for treating a viral infection in a subject having the viral infection, the method comprising administering to the subject a compound having a structure represented by a formula:

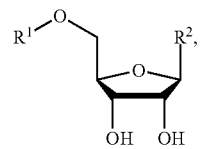

wherein $R^1$ is selected from hydrogen, —C(O)$R^{10}$, —C(O)CH($R^{11}$)NH$_2$, —P(O)(OAr$^1$)NHCH($R^{12}$)CO$_2R^{13}$, and —P(O)(O$R^{14a}$)(O$R^{14b}$);

wherein $R^{10}$, when present, is selected from C1-C20 alkyl and C2-C20 alkenyl;

wherein $^R$H, when present, is a residue of an amino acid selected from arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan;

wherein $R^{12}$, when present, is selected from C1-C6 alkyl and C3-C6 cycloalkyl;

wherein $R^{13}$, when present, is selected from C1-C8 alkyl, C3-C8 cycloalkyl, Ar$^2$, and —CH$_2$Ar$^2$;

wherein Ar$^2$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{14a}$ and $R^{14b}$, when present, is independently C1-C8 alkyl; and wherein Ar$^1$, when present, is selected from C6-C14 aryl and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^2$ is a structure represented by a formula selected from:

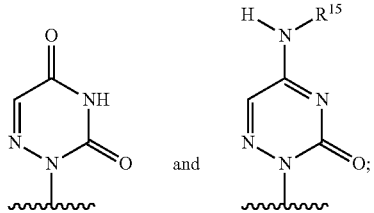

and wherein $R^{15}$, when present, is selected from hydrogen, —C(O)(C1-C20 alkyl), —C(O)(C3-C6 cycloalkyl), and —C(O)(C2-C20 alkenyl), provided that when $R^1$ is hydrogen, then $R^2$ is

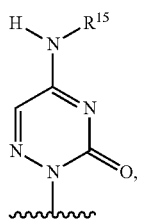

and $R^{15}$ is —C(O)(C1-C20 alkyl), —C(O)(C3-C6 cycloalkyl), or —C(O)(C2-C20 alkenyl), or a pharmaceutically acceptable salt thereof.

15. The method of claim 14, wherein the viral infection is due to an Alphavirus or a Flavivirus.

16. The method of claim 14, wherein the viral infection is due to a Coronavirus.

17. The method of claim 16, wherein the Coronavirus is selected from Middle East Respiratory Syndromes coronavirus (MERS-CoV), Severe Acute Respiratory Syndrome coronavirus (SARS-CoV), and SARS-CoV-2.

18. The method of claim 14, wherein the viral infection is selected from human immunodeficiency virus (HIV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, influenza, respiratory syncytial virus, viral pneumonia, yellow fever virus, tick-borne encephalitis virus, Chikungunya virus (CHIKV), Ross River virus, Venezuelan equine encephalitis (VEEV), Eastern equine encephalitis (EEEV), Western equine encephalitis (WEEV), dengue (DENY), influenza, West Nile virus (WNV), zika (ZIKV), Middle East Respiratory Syndromes (MERS), Severe Acute Respiratory Syndrome coronavirus (SARS), and coronavirus disease 2019 (COVID-19).

* * * * *